United States Patent
Macknik et al.

(10) Patent No.: US 11,013,411 B1
(45) Date of Patent: May 25, 2021

(54) CHROMATIC BIOLUMINESCENCE AS A CELLULAR LEVEL READOUT SYSTEM OF NEURAL ACTIVITY

(71) Applicants: THE RESEARCH FOUNDATION FOR THE STATE UNIVERSITY OF NEW YORK, Albany, NY (US); CORNELL UNIVERSITY, Ithaca, NY (US)

(72) Inventors: Stephen Macknik, Albany, NY (US); Susana Martinez-Conde, Albany, NY (US); Nozomi Nishimura, Ithaca, NY (US); Christopher Schaffer, Ithaca, NY (US); Mitch Pender, Freeville, NY (US)

(73) Assignees: THE RESEARCH FOUNDATION FOR THE STATE UNIVERSITY OF NEW YORK, Albany, NY (US); CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/251,499

(22) PCT Filed: Jun. 12, 2019

(86) PCT No.: PCT/US2019/036668
§ 371 (c)(1),
(2) Date: Dec. 11, 2020

(87) PCT Pub. No.: WO2019/241319
PCT Pub. Date: Dec. 19, 2019

Related U.S. Application Data

(60) Provisional application No. 62/684,737, filed on Jun. 13, 2018, provisional application No. 62/684,740, filed on Jun. 14, 2018.

(51) Int. Cl.
*A61B 5/00* (2006.01)
*C12N 15/65* (2006.01)

(52) U.S. Cl.
CPC .......... *A61B 5/0036* (2018.08); *A61B 5/0042* (2013.01); *A61B 5/0071* (2013.01);
(Continued)

(58) Field of Classification Search
CPC ... A61B 5/0036; A61B 5/7246; A61B 5/4884; A61B 5/0071
See application file for complete search history.

(56) References Cited

U.S. PATENT DOCUMENTS 7,038,106 B1    5/2006  Kaiser et al.
8,263,821 B2 *  9/2012  Brulet ................ A01K 67/0275
                                                  800/3

(Continued)

FOREIGN PATENT DOCUMENTS

KR    20050053783 A    6/2005
WO       0192300 A2   12/2001

(Continued)

OTHER PUBLICATIONS

International Search Report and Written Opinion of the International Searching Authority for International Application No. PCT/US2019/036668 dated Oct. 4, 2019.

(Continued)

*Primary Examiner* — Joseph M Santos Rodriguez
(74) *Attorney, Agent, or Firm* — Heslin Rothenberg Farley & Mesiti P.C.

(57) ABSTRACT

Provided is a method of detecting neural activity, including inducing neurons of a subject to express two or more polypeptides each comprising an amino acid sequence represented by one of SEQ ID NOs:13-24, wherein inducing (Continued)

comprises stimulating interneuronally different relative levels of expression of the two or more polypeptides; applying coelenterazine to the subject; applying a first stimulation of neural activity to the subject; detecting a first spatiotemporal and spectral pattern of electromagnetic radiation emitted by neurons of the subject in response to the first stimulation; recording the first spatiotemporal and spectral pattern of electromagnetic radiation in a computer memory; applying a second stimulation of neural activity to the subject; detecting a second spatiotemporal and spectral pattern of electromagnetic radiation emitted by neurons of the subject in response to the second stimulation; comparing the second spatiotemporal and spectral pattern of electromagnetic radiation to the first spatiotemporal and spectral pattern of electromagnetic radiation, wherein differences between the second spatiotemporal and spectral pattern of electromagnetic radiation and the first spatiotemporal and spectral pattern of electromagnetic radiation indicate differences in neural activity caused by the first stimulation and the second stimulation.

23 Claims, 19 Drawing Sheets

Specification includes a Sequence Listing.

(52) U.S. Cl.
CPC .......... *A61B 5/4848* (2013.01); *A61B 5/4884* (2013.01); *A61B 5/7246* (2013.01); *C12N 15/65* (2013.01)

(56) References Cited

U.S. PATENT DOCUMENTS

| | | | |
|---|---|---|---|
| 8,583,565 B2 * | 11/2013 | Shoureshi | G06N 3/0436 706/2 |
| 9,908,918 B2 * | 3/2018 | Lin | G01N 21/6428 |
| 2005/0273867 A1 | 12/2005 | Brulet et al. | |
| 2007/0274923 A1 | 11/2007 | Brulet et al. | |
| 2011/0118806 A1 | 5/2011 | Pascual-Leone et al. | |
| 2011/0208675 A1 | 8/2011 | Shoureshi et al. | |
| 2015/0261294 A1 | 9/2015 | Urbach | |
| 2016/0103487 A1 | 4/2016 | Crawford et al. | |
| 2016/0270723 A1 | 9/2016 | Deisseroth et al. | |
| 2017/0032520 A1 | 2/2017 | Nitzken et al. | |

FOREIGN PATENT DOCUMENTS

| | | |
|---|---|---|
| WO | 2017072342 A1 | 5/2017 |
| WO | 2019241318 A1 | 12/2019 |

OTHER PUBLICATIONS

International Search Report and Written Opinion of the International Searching Authority for International Application No. PCT/US2019/036666 dated Oct. 18, 2019.

Abdelfattah, A.S., et al., "A Bright and Fast Red Fluorescent Protein Voltage Indicator That Reports Neuronal Activity in Organotypic Brain Slices", The Journal of Neuroscience, vol. 36, No. 8, pp. 2458-2472 (2016).

Bakayan, A., et al., "Red Fluorescent Protein-Aequorin Fusions as Improved Bioluminescent Ca2+ Reporters in Single Cells and Mice", PLOS ONE, vol. 6, Issue 5, e19520, pp. 1-13.

Baubet, V., et al., "Chimeric green fluorescent protein-aequorin as bioluminescent Ca2+ reporters at the single-cell level", PNAS, vol. 97, No. 13, pp. 7260-7265 (2000).

Chen, T.-W., et al., "Ultra-sensitive fluorescent proteins for imaging neuronal activity", Nature, vol. 499, No. 7458, pp. 295-300 (2013).

Curie, T., et al., "Red-Shifted Aequorin-Based Bioluminescent Reporters for in Vivo Imaging of Ca2+ Signaling", Molecular Imaging, vol. 6, No. 1, pp. 30-42 (2007).

NCBI, GenBank Accession No. ABN09646.1, 'GFP-aequorin fusion protein [synthetic construct]', Feb. 6, 2007.

Han, Z., et al., "Mechanistic Studies of the Genetically Encoded Fluorescent Protein Voltage Probe ArcLight", PLOS ONE, vol. 9, No. 11, e113873, pp. 1-21.

Kaplitt, M.G., et al., "Safety and tolerability of gene therapy with an adeno-associated virus (AAV) borne GAD gene for Parkinson's disease: an open label, phase I trial", Lancet, vol. 369, pp. 2097-2105 (2007).

Kremkow, Jens, et al., "Principles underlying sensory map topography in primary visual cortex", Nature, vol. 533, pp. 52-57 (2016).

Manjarres, I.M., et al., "Red and green aequorins for simultaneous monitoring of Ca2+ signals from two different Drganelles", Pfugers Arch—Eur J. Physiol, vol. 455, pp. 961-970 (2008).

Mittmann, W., et al., "Two-photon calcium imaging of evoked activity from L5 somatosensory neurons in vivo", Nature Neuroscience, vol. 14, p. 8, pp. 1089-1093 (2011).

Naumann, E.A., et al., "Monitoring neural activity with bioluminescence during natural behavior", Nature Neuroscience, vol. 13, No. 4, pp. 513-520 (2010).

Pender, M.A., et al., "Multicolor Genetically-Encoded Calcium-Sensitive Bioluminescent Reporters of Neural Activity for Brain-Machine Interfaces", Optics in the Life Sciences (2017).

Pender, M.A., et al., "438.15 / WW13—Multicolor genetically-encoded calcium-sensitive bioluminescent reporters of neural activity for brain-machine interfaces", Poster Presentation, Nov. 14, 2016 http://www.abstractsonline/com/pp8/#!/4071/presentation/9341.

Platisa, J., et al., "Directed Evolution of Key Residues in Fluorescent Protein Inverses the Polarity of Voltage Sensitivity in the Genetically Encoded Indicator ArcLight", ACS Chem. Neurosci., vol. 8, pp. 513-523 (2017).

Rodriguez-Garcia, A., et al., "GAP, an aequorin-based fluorescent indicator for imaging Ca2+ in organelles", PNAS, vol. 111, No. 7, pp. 2584-2589 (2014).

Rogers, K.L., et al., "Non-Invasive In Vivo Imaging of Calcium Signaling in Mice", PLOS ONE, Issue 10, e971, pp. 1-15 (2007).

Stosiek, C., et al., "In vivo two-photon calcium imaging of neuronal networks", PNAS, vol. 100, No. 12, pp. 7319-7324 (2003).

Webb, S.E., et al., "Retrospective on the Development of Aequorin and Aequorin-Based Imaging to Visualize Changes in Intracellular Free [Ca2+]", Molecular Reproduction & Development, vol. 82, pp. 563-586 (2015).

Pender, M.A., et al., "Multicolor Genetically-Encoded Calcium-Sensitive Bioluminescent Reporters of Neural Activity for Brain Machine Interfaces", Presentation, 2016 Annual Meeting of Biomedical Engineering Society, Oct. 5-8, 2016.

* cited by examiner

CHROMATIC BIOLUMINESCENCE AS A CELLULAR LEVEL READOUT SYSTEM OF NEURAL ACTIVITY

CROSS REFERENCE TO RELATED APPLICATIONS

This application is a national stage filing under 35 U.S.C. § 371 of International Application No. PCT/US2019/036668, filed on Jun. 12, 2019, published as WO 2019/241319 on Dec. 19, 2019, and claims priority to U.S. provisional patent application No. 62/684,737, filed Jun. 13, 2018 and U.S. provisional patent application No. 62/684,740, filed Jun. 14, 2018. The entire contents of the said applications are incorporated by reference in their entireties.

GOVERNMENT RIGHTS STATEMENT

This invention was made with Government support under grant number 1706761 and 1453339 awarded by the National Science Foundation and grant number EY028391 awarded by the National Institutes of Health. The Government has certain rights in the invention.

SEQUENCE LISTING

The instant application contains a Sequence Listing, created on Jun. 1, 2019; the file, in ASCII format, is designated H1482103.txt and is 85.4 KB in size. The file is hereby incorporated by reference in its entirety into the instant application.

FIELD OF THE INVENTION

The subject matter disclosed herein relates to bioluminescent compounds. More particularly, this disclosure relates to calcium-sensitive bioluminescent indicators for reporting neural activity.

BACKGROUND OF THE INVENTION

Certain compounds are capable of emitting luminescence in response to changes of various intracellular ion concentrations. For example, some proteins, in combination with particular compounds within a cell, can emit electromagnetic radiation when complexed with intracellular calcium ions. Because depolarization of a neuron concordant with generation of an action potential entails an elevation in intracellular calcium, such compounds can function as indicators of neural activity, emitting fluorescence from neurons firing an action potential. Potential use of such compounds could include, for example, visualization of activity within neurons of a brain or nerve in vivo or visualizing neural activity of slice preparations or other ex vivo applications.

Brain-machine interfaces (BMIs) allow direct communication to occur between the brain and an external device. BMIs have the potential to restore sensory or motor function to patients with spinal cord injuries or amputations. Preferably, advantageous features of a BMI system would include (1) minimal invasiveness, (2) long lifetime, (3) provision of high information content, (4) robustness, and (5) portability. Conventional BMI systems are deficient in these features. A particular advantageous feature of a BMI system would be if it could differentiate activity of particular neurons within an observed field of neurons, such as when neurons responsive to one input but not another are anatomically co-mingled with neurons of the converse responsiveness, or that do not respond to either of said stimulus, respond to both, or otherwise respond differently to one or more stimuli than do other neurons located in proximity thereto. Conventional BMI systems do not provide such ability to distinguish between activity of neighboring neurons.

A species of jellyfish, Aequorea victoria, produces a protein known as aequorin which is a Ca2+ dependent bioluminescent protein. In jellyfish, aequorin exists as a complex with fluorescent protein (e.g., GFP). In the presence of calcium, aequorin is able to act as a catalytic enzyme in a luciferase reaction. Aequorin oxidizes coelenterazine (CTZ), a molecular cofactor found naturally in jellyfish. The energy gained from the oxidation reaction is passed to the neighboring fluorescent protein which (in the case of GFP) releases a green photon in a process known as chemiluminescence resonance energy transfer (CRET). As a result, neural activity can be reported by aequorin as demonstrated in zebrafish and nerves in the legs of mice. Aequorin-fluorescent protein constructs act as calcium indicators because they have good temporal resolution and are bright with low or no background noise. However, although a single color bioluminescent indicator in the brain can report bulk activity, it cannot distinguish the activity between multiple, intermingled neurons because of the temporal overlap between signals generated from different neurons.

The present disclosure is directed to overcoming these and other deficiencies in the art. As disclosed further herein, use of bioluminescent proteins can provide significant improvement over conventional BMI systems.

SUMMARY OF THE INVENTION

In one aspect, provided is a method of detecting neural activity, including inducing neurons of a subject to express at least one of two or more polypeptides each comprising an amino acid sequence represented by SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:26, SEQ ID NO: 28, or a sequence having at least 90% sequence homology with any one of the foregoing, wherein inducing comprises stimulating interneuronally different relative levels of expression of the two or more polypeptides; applying coelenterazine to the subject; applying a first stimulation of neural activity to the subject; detecting a first spatiotemporal and spectral pattern of electromagnetic radiation emitted by neurons of the subject in response to the first stimulation; recording the first spatiotemporal and spectral pattern of electromagnetic radiation in a computer memory; applying a second stimulation of neural activity to the subject; detecting a second spatiotemporal and spectral pattern of electromagnetic radiation emitted by neurons of the subject in response to the second stimulation; analyzing, using one or more microprocessors, the second spatiotemporal and spectral pattern of electromagnetic radiation to the first spatiotemporal and spectral pattern of electromagnetic radiation, wherein the one or more microprocessors are configured to determine differences and similarities between the second spatiotemporal and spectral pattern of electromagnetic radiation and the first spatiotemporal and spectral pattern of electromagnetic radiation, differences indicate differences in neural activity caused by the first stimulation and the second stimulation, and similarities indicate similarities in neural activity caused by the first stimulation and the second stimulation.

In an embodiment, the two or more polypeptides each include a sequence having at least 90%, at least 95%, or 100% sequence homology with SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:26, or SEQ ID NO:28.

In another embodiment, inducing includes transfecting neurons with at least one of two or more polynucleotides wherein each of the two or more polynucleotides encodes for one of the polypeptides. In an example, a polynucleotide includes a viral vector. In another example, the polynucleotides include a plasmid.

In another embodiment, the first stimulation, the second stimulation, or both, are sensory stimulation. In an example, the first stimulation, the second stimulation, or both, are visual stimulation, olfactory stimulation, auditory stimulation, gustatory stimulation, tactile stimulation, proprioceptive stimulation, pain stimulation, or electrical stimulation. In another embodiment, the first stimulation, the second stimulation, or both, are pharmacological stimulation. In another embodiment, the first stimulation, the second stimulation, or both, are electrical neural stimulation. In another embodiment, the subject is a rat, a mouse, a human, or a non-human subject.

Also provided is a method of detecting neural activity, including inducing neurons of a subject to express at least one of two or more polypeptides each comprising a fluorescent protein connected to an aequorin by a linker, wherein the amino acid sequence of each of the fluorescent proteins is independently represented by amino acids 1 through 239 of SEQ ID NO:13, amino acids 1 through 239 of SEQ ID NO:13, amino acids 1 through 239 of SEQ ID NO:14, amino acids 1 through 237 of SEQ ID NO:15, amino acids 1 through 237 of SEQ ID NO:16, amino acids 1-239 of SEQ ID NO:26, or amino acids 1-476 of SEQ ID NO:28, the amino acid sequence of each of the linkers is independently represented by amino acids 240 through 256 of SEQ ID NO:13, amino acids 240-300 of SEQ ID NO:26, or amino acids 477-493 of SEQ ID NO:28, and the amino acid sequences of each of the aequorins is independently represented by amino acids 257 through 448 of SEQ ID NO:13, amino acids 257 through 450 of SEQ ID NO:17, amino acids 257 through 450 of SEQ ID NO:21, amino acids 381-488 of SEQ ID NO:26, or amino acids 494-685 of SEQ ID NO 28; and applying coelenterazine to the subject; applying a first stimulation of neural activity to the subject; detecting a first spatiotemporal and spectral pattern of electromagnetic radiation emitted by neurons of the subject in response to the first stimulation; recording the first spatiotemporal and spectral pattern of electromagnetic radiation in a computer memory; applying a second stimulation of neural activity to the subject; detecting a second spatiotemporal and spectral pattern of electromagnetic radiation emitted by neurons of the subject in response to the second stimulation; analyzing, using one or more microprocessors, the second spatiotemporal and spectral pattern of electromagnetic radiation to the first spatiotemporal and spectral pattern of electromagnetic radiation, wherein the one or more microprocessors are configured to determine differences and similarities between the second spatiotemporal and spectral pattern of electromagnetic radiation and the first spatiotemporal and spectral pattern of electromagnetic radiation, differences indicate differences in neural activity caused by the first stimulation and the second stimulation, and similarities indicate similarities in neural activity caused by the first stimulation and the second stimulation.

In an embodiment, inducing comprises transfecting neurons with at least one of two or more polynucleotides wherein each of the two or more polynucleotides encodes for one of the polypeptides. In an example, a polynucleotide includes a viral vector. In another example, the polynucleotides include a plasmid. In another embodiment, the first stimulation, the second stimulation, or both, are sensory stimulation. In an example, the first stimulation, the second stimulation, or both, are visual stimulation, olfactory stimulation, auditory stimulation, gustatory stimulation, tactile stimulation, proprioceptive stimulation, pain stimulation, or electrical stimulation. In another embodiment, the first stimulation, the second stimulation, or both, are pharmacological stimulation. In yet another embodiment, the first stimulation, the second stimulation, or both, are electrical neural stimulation. In another embodiment, the subject is a rat, a mouse, a human, or a non-human subject.

In another embodiment, the method further includes recording the second spatiotemporal and spectral pattern of electromagnetic radiation in a computer memory, wherein analyzing includes comparing the first spatiotemporal and spectral pattern of electromagnetic radiation stored in the computer memory to the second spatiotemporal and spectral pattern of electromagnetic radiation stored in the computer memory.

BRIEF DESCRIPTION OF THE DRAWINGS

These and other features, aspects, and advantages of the present disclosure will become better understood when the following detailed description is read with reference to the accompanying drawings, wherein.

DETAILED DESCRIPTION OF THE INVENTION

Figure 1:
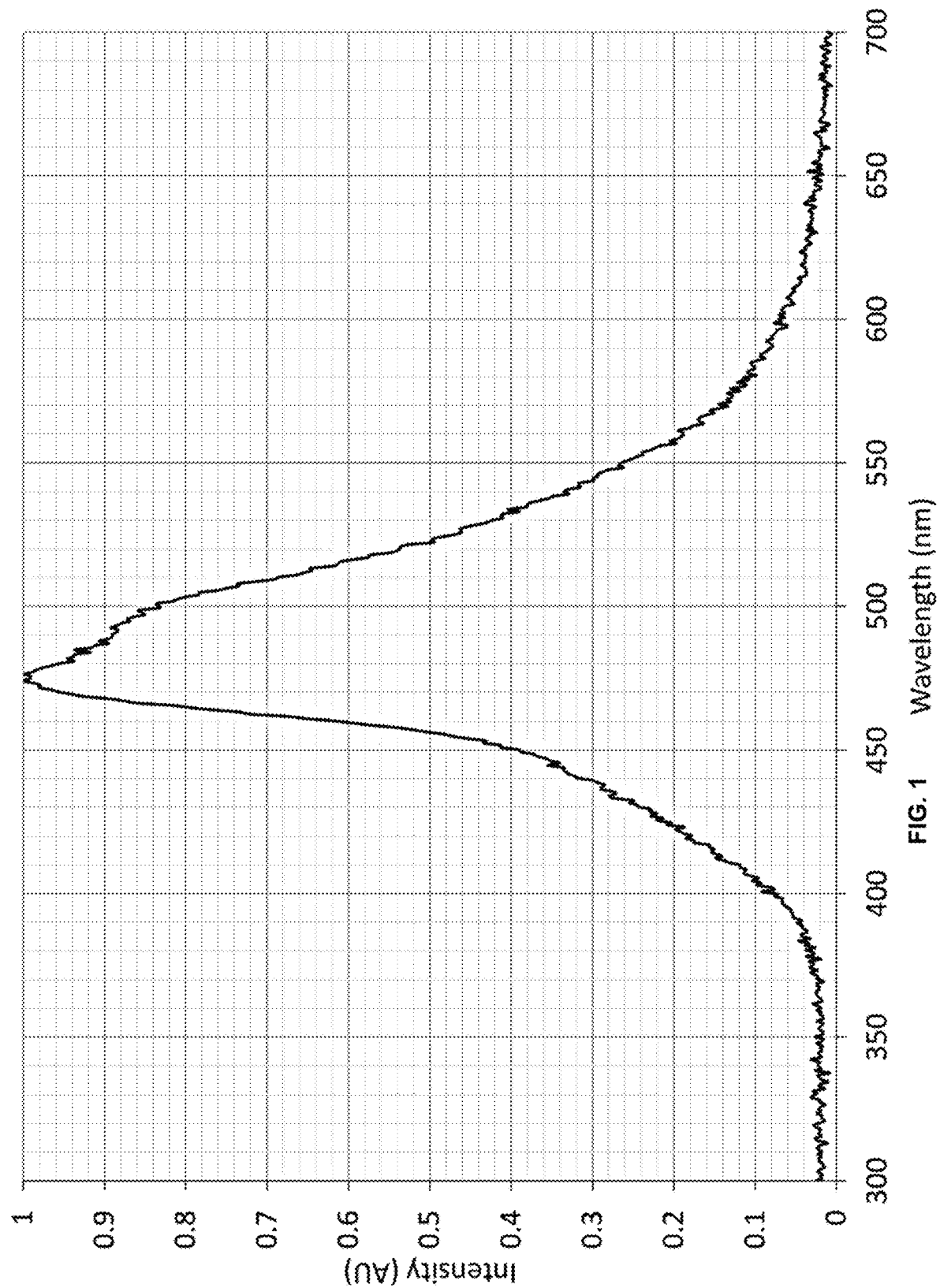
FIG. 1 shows bioluminescent spectra sampled in response to saturating calcium (200 mM) at room temperature with 100 ms integration time on Ocean Optics QE65000 after overnight incubation in Coelenterazine-H for SEQ ID NO:13.

This disclosure relates to compositions, methods, systems, and kits for inducing cells such as neurons to emit detectable electromagnetic radiation, including having wavelengths of visible light, when activated and experiencing elevated calcium levels intracellularly. Compositions disclosed herein could likewise be used for identifying elevations of calcium levels intracellularly in other cells such as myocytes such as cardiomyocytes, or other cell types. Such compositions could also be used for measuring changes in extracellular calcium levels, or in solutions without whole cells.

Bioluminescence imaging (BLI) is a form of optical imaging that utilizes the detectable electromagnetic radiation, such as visible light, produced during luciferase-mediated oxidation of substrates to track processes at a molecular level. Molecular imaging with bioluminescence is advantageous because it is both non-invasive and has high signal-to-noise ratios because mammalian tissue has low intrinsic bioluminescence. As disclosed herein, neurons may be manipulated to express bioluminescent proteins that bioluminesce in response to elevated intracellular calcium levels. Furthermore, different species of bioluminescent molecules disclosed herein emit differing wavelengths of electromagnetic radiation. Thus, a neuron expressing one bioluminescent molecule would emit one wavelength of electromagnetic radiation in response to elevated calcium levels, while another neuron expressing a different bioluminescent molecule, or the same bioluminescent molecule in combination with one or more different bioluminescent molecule, would emit electromagnetic radiation of a different frequency upon elevation of intracellular calcium.

Surprisingly, as further disclosed herein, inducing expression of different combinations and/or different levels of bioluminescent, calcium-responsive molecules in different neurons gives rise to an exponential increase in the different emission spectra exhibited from cell to cell in response to calcium influx. That is, when inducing the expression of different levels of a bioluminescent molecule and/or different bioluminescent molecules in different combinations from one cell to the next, and or with differing levels of relative expression between bioluminescent molecules expressed per cell, each cell emits at a net frequency reflective of the particular bioluminescent molecule(s) it expresses and at a given level of expression. With, for example, six different bioluminescent markers applied to a field of neurons, at least 3,000 or more distinct emission spectra can be observed from different cells in response to calcium elevations owing to stochastically-determined differences in which bioluminescent molecules become expressed and at what relative levels to one another per cell. The wide variety of differentiable spectra obtained was particularly surprising in view of the failure of other, conventional technologies (e.g., BRAINBOW technology) to generate such diversity when cells are induced to express different marker compounds and/or at different levels. The success of the combinatorial approach undertaken as disclosed herein in generating a wide diversity of emission spectra per cell represents a significant advance over conventional technology that would not have been predicted on the basis of previous attempts with different markers.

Thus, multiple bioluminescent molecules may be applied simultaneously across a field of neurons such that neurons express different bioluminescent molecules at relative levels that differs stochastically from neuron to neuron. For example, two, three, four, five, six, or more bioluminescent markers with emission spectra that differ from each other may be applied across a field of neurons, and different neurons express different levels of each of the one, two, three, four, five, six, or more bioluminescent markers compared to other neurons in the field or with which each neuron is spatially comingled. As a result, each neuron would emit in the presence of elevated intracellular calcium at an emission frequency that is a reflection of the combined emission spectrum of each of the one, two, three, four, five, six, or more bioluminescent markers it is expressing at the level at which it is expressing each thereof. With different neurons stochastically expressing different relative levels of the two, three, four, five, or more bioluminescent marks compared to the other neurons within the field, each neuron would fluoresce at a different frequency than the other neurons upon elevations of intracellular calcium. Thus, activity of one neuron as opposed to another could be distinguished not just by the location of the neuron emitting bioluminescence but also by the frequency of bioluminescence it is emitting.

As disclosed herein, where cells such as neurons are described as exhibiting different levels of expression of two or more bioluminescent markers such a bioluminescent polypeptides, an example is where a neuron may express none of either of two markers, or some of only one marker, or some of only another marker, or some of any two or more of the two or more markers (such as of up to six or more). Thus, in some examples, a field of neurons may be induced to express from one to six or more bioluminescent proteins. Some neurons of the field may express only one of the six. For example, six different neurons may each express only one of the six markers, and each a different marker than the other of those six. Other neurons may express two or more makers, in any combination. This non-limiting example may include a plurality of neurons wherein each of the plurality of neurons expresses one or more bioluminescent markers having differing amino acid sequences from each other, and a level of expression of a first of the one or more polypeptides relative to a level of expression of a second of the one or more polypeptides in a first neuron (for example, a neuron that expresses some of one marker and none of any other) differs from a level of expression of the first of the one or more polypeptides relative to a level of expression of the second of the one or more polypeptides in a second neuron (which may express some of each of two or more markers, or some of one marker not expressed by the first neuron and some of a marker not expressed in the first neuron). Other neurons of the field may each express more than none of any combination of at least two of the bioluminescent markers, which may also include a first neuron and a second that express different relative levels of two or more bioluminescent markers than each other, or than any neuron that expresses some of only one but not of any other bioluminescent marker.

Expression of bioluminescent compounds may be accomplished by any known method. For example, cells can be transfected with nucleotide sequences (DNA, RNA, etc.) that encode for bioluminescent proteins as disclosed herein. As used herein, transfecting, transfected, or transfection includes any process for introducing nucleic acids or proteins into cells, including transduction through viral vector-mediated gene transfer. For example, adeno-associated viral (AAV) vectors may be used to transfect neurons, with different vectors driving expression of genetic material encoding different bioluminescent proteins. AAV vectors derived from a particular serotype or from mixed serotypes may be adopted and used depending on the particular application. If a population of neurons is contacted with a solution or solutions containing different viral vectors such as these, each containing material to drive the expression of different bioluminescent proteins, different cells can be transfected with stochastically different levels of payload from different vectors and thus express relative levels of bioluminescent proteins that differ inter-neuronally. In other examples, different viral vectors may be used, such as lentiviruses, retroviruses, HSV-viral vectors, or other viral vectors known to be effective at driving protein expression in neurons. In some examples, combinations of viral vectors may be used, rather than only one type of vector used to drive expression of all bioluminescent proteins.

Other transfection methods may also be used to drive expression, such as lipofection, electroporation, microinjection, gene gun, continuous infusion, and sonication, impalefection, hydrostatic pressure transfection, with genetic material that drives expression of the bioluminescent protein. In other examples, bioluminescent proteins themselves may be introduced into cells rather than genetic material driving their production by cells. All such examples are considered methods of promoting expression of a bioluminescent composition or compositions in cells, and may be used in combination with one another. In other examples, an extracellular bioluminescent compound or compounds may be used such as by addition of a bioluminescent polypeptide or polypeptides directly to a solution, for indicating elevated calcium levels therein.

A bioluminescent composition in accordance with the present disclosure may be a polypeptide including a fluorescent protein connected to an aequorin by a linker. For example, the fluorescent protein may be N-terminal to the linker and the aequorin may be C-terminal to the linker. In other examples, the aequorin may be N-terminal and the fluorescent protein may be C-terminal. In some examples, there may not be additional amino acids between a fluorescent protein and a linker, or between a linker and an aequorin, or neither between a fluorescent protein and a linker nor between a linker and an aequorin. Polynucleotides encoding for such polypeptides are also disclosed herein. As would be appreciated, because of the degeneracy of the genetic code, many different polynucleotide sequences could drive expression of a given bioluminescent polypeptide disclosed herein, and all such sequences for all such bioluminescent polypeptides are explicitly included in the present disclosure. Such a polynucleotide may exist in a form convenient for storage or expression within a cell such as a plasmid. Such a plasmid may contain an origin of replication, transcriptional start sites, and/or other structural features that promote replication thereof in a host cell and/or production of and/or translation from a transcript to promote expression of a bioluminescent polypeptide.

Examples of fluorescent proteins include mCerulean (represented by amino acids 1-239 of SEQ ID NO:13), eCFP (represented by amino acids 1-239 of SEQ ID NO:14), mTagBFP2 (represented by amino acids 1-237 of SEQ ID NO:15), mTFP1 (represented by amino acids 1-237 of SEQ ID NO:16), eGFP (represented by amino acids 1-239 of SEQ ID NO:26), and tdTomato (represented by amino acids 1-476 of SEQ ID NO:28). Examples of linkers are represented by amino acids 240-256 of SEQ ID NO:13, amino acids 240-300 of SEQ ID NO:26, and amino acids 477-493 of SEQ ID NO:28. Other examples may include a linker as a portion of an amino acid sequence linking a fluorescent protein to an aequorin wherein the linker has an amino acid sequence that differs from the foregoing examples. In some nonlimiting examples, the linker may be from between 10 and 100 amino acids in length. Examples of aequorins include aequorin from *Aequorea victoria* (represented by amino acids 257-448 of SEQ ID NO:13), obelin from *Obelia longissima* (represented by amino acids 257-450 of SEQ ID NO:17), and aequorin from *Aequorea macrodactyla* (represented by amino acids 257-450 of SEQ ID NO:21), referred to herein as AMac. All combinations of any one of the foregoing fluorescent proteins with any one of the foregoing aequorins connected by a linker are included in the present disclosure. A non-limiting list of examples of such combinations includes polypeptides with amino acid sequences represented by SEQ ID NOs:13-24, 26, and 28. All polynucleotides that encode for any bioluminescent protein disclosed herein is also explicitly included in the present disclosure. A non-limiting list of examples includes polynucleotides with sequences represented by SEQ ID NOs:1-12 (which encode for the bioluminescent proteins with amino acid sequences corresponding to SEQ ID NOs:13-24, respectively), and SEQ ID NOs:25 and 27 (which encode for the bioluminescent proteins with amino acid sequences corresponding to SEQ ID NOs:26 and 28, respectively.

In some examples, a bioluminescent polypeptide may include a phosphoprotein that differs by one or more amino acids from mCerulean (as represented by amino acids 1-239 of SEQ ID NO:13), eCFP (as represented by amino acids 1-239 of SEQ ID NO:14), mTagBFP2 (as represented by amino acids 1-237 of SEQ ID NO:15), mTFP1 (represented by amino acids 1-237 of SEQ ID NO:16), eGFP (represented by amino acids 1-239 of SEQ ID NO:26), or tdTomato (represented by amino acids 1-476 of SEQ ID NO:28). For example, a phosphoprotein segment of a bioluminescent protein may differ by up to 10% in amino acid sequence, or by up to 5% in amino acid sequence, or by between 10% and 5% or between 5% and 0% from the foregoing specific examples. A linker segment of a bioluminescent phosphoprotein may also differ by 10%, 5%, between 10% and 5%, or between 5% and 0% from amino acids 240-256 of SEQ ID NO:13, amino acids 240-300 of SEQ ID NO:26, and amino acids 477-493 of SEQ ID NO:28. Furthermore, an aequorin segment of a bioluminescent phosphoprotein may differ in amino acid content by 10%, 5%, between 10% and 5%, or between 5% and 0% from amino acids 257-448 of SEQ ID NO:13, amino acids 257-450 of SEQ ID NO:17, or amino acids 257-450 of SEQ ID NO:21. A bioluminescent protein may differ by 10%, 5%, between 10% and 5%, or between 5% and 0%, from any one of SEQ ID NOs:13-24, 26, or 28. All polynucleotide sequences that may encode for any of the foregoing segments of bioluminescent proteins or bioluminescent proteins are explicitly disclosed herein. For example, a nucleotide sequence may differ by 10%, 5%, between 0% and 5%, or between 5% and 0% in nucleotide sequence from SEQ ID NOs.1-12, 25, or 27.

Any fluorescent protein may be linked to any aequorin by any linker disclosed herein. Some neurons may be induced to express a bioluminescent marker of activity with one fluorescent protein linked to a given aequorin by a linker, whereas another neuron may be induced to express a bioluminescent marker of activity with the same fluorescent protein and linker but a different aequorin, or the same linker and aequorin but a different fluorescent protein, or the same fluorescent protein and aequorin but a different linker. In other cases two neurons may be induced to express bioluminescent markers of activity with the same fluorescent protein as each other but a different linker and different aequorin, or the same linker as each other but a different fluorescent protein and a different aequorin, or the same aequorin as each other but a different fluorescent protein and a different linker. All possible combinations of al fluorescent proteins, linkers, and aequorins disclosed herein are explicitly contemplated and included in the present disclosure. In this manner, neurons may be independently induced to express bioluminescent markers of activity that have no, only one, only two, or three of a fluorescent protein, linker, and/or aequorin in common with each other.

Neurons may be contacted with a coelenterazine molecule together with a bioluminescent protein or upon induced expression thereof. For example, coelenterazine or 2-deoxycoelenterazine may be applied to neurons transfected with a polynucleotide sequence that drives expression of a bioluminescent protein disclosed herein. In the presence of calcium, such as when intracellular calcium levels are elevated in conjunction with a depolarization event, aequorin may oxidize a coelenterazine molecule or analog thereof (e.g., 2-deoxycoelenterazine), whereupon the energy gained from the oxidation reaction is passed to the fluorescent protein segment of the bioluminescent protein inducing photon release thereby by CRET. Depending on the combination of aequorin and fluorescent protein segments used, and different combinations of expression of various bioluminescent proteins comprising such various segments, different neurons may emit different wavelengths of fluorescence when exposed to elevated calcium levels. Bioluminescent polypeptides or polynucleotides encoding therefor or viral vectors for driving the expression thereof as disclosed herein may be used in neurons taken from a subject of any intended species for ex vivo use or applied in vivo to a nervous system of a subject of any given species of interest. For example, with appropriate promoter sequences and transcriptional features for a given target species, they could be adopted for use in invertebrates or vertebrates. For example, they could be used in insects, fish, amphibians, reptiles, birds, or mammals. For example, they could be used in rodent, ungulate, canine, feline, leporine, porcine, primate, or other species. For example, they could be used in mice, rats, humans, or non-human primates. As disclosed herein, bioluminescent proteins or vectors for driving their expression may be injected or otherwise applied to a nervous system of such species then bioluminescence of the treated area observed in response to stimulatory input known or believed to recruit activity of neurons in such region, or hypothesized or suspected of doing so.

For detecting and measuring bioluminescence emitted by neurons expressing a bioluminescent protein as disclosed herein, various known optical imaging devices and techniques may be used. Charge coupled device (CCD) cameras, for example, are imaging modalities that spatially encode incident photons and their intensity into an image. Integrating photon counts on a CCD camera, however, may decrease temporal resolution. To increase temporal resolution to spatially localize neurons, photodetectors (for example, photon counting multiplier tubes (PMTs), photodiodes, or CCD/CMOS detector technologies) may be used. In an example, PMTs convert photonic signals into a current which decreases spatial resolution since it diffusely collects scattered photons. However, by color-coding cells such as neurons with different bioluminescent compositions and/or different combinations of compositions to permit interneuronal differentiation of the frequency of electromagnetic radiation emitted in response to elevated intracellular calcium, different color indicators and sampling with spectrally separated PMTs, a unique spectrum of colors that provide spatial resolution is obtained as disclosed herein. With a high sampling rate, PMTs are able to collect photons from hundreds of neurons that may be firing. Recording equipment may be sensitive to a wide range of frequency of electromagnetic radiation, within the visual spectrum, or outside thereof, depending on emission spectra of bioluminescent proteins used for signaling neural activity.

Such recording device or system may be connected to a computer for recording and analyzing bioluminescence emitted from a given population or field of neurons being measured. Recordings may be recorded on standard computer media systems and/or analyzed by software for depicting and analyzing activity of neurons within a recording field in response to different types of stimuli (e.g., sensory stimuli, pharmacological stimuli, electrical stimuli, etc.). Visualization and/or recording may also be performed during other events believed, known, or predicted to recruit or involve activation of populations of neurons in different brain regions, such as cortical brain regions. Such examples could include detecting bioluminescence in cortical motor areas during ideation or execution of movement of particular body areas or parts, visual cortical areas during experience or ideation of visual experience, during seizure or ictal events, during specific cognitive tasks, during affective states, including pathological affective states such as anxiety, depression, or mania, during sleep, or other states.

Use of bioluminescent proteins as disclosed herein may result in patterns of activity across a field of neurons. Within a given field, an area may be visualized and bioluminescent emission recorded. During a recording session, multiple parameters may be recorded, such as in relation to specific pixels or discrete loci or a recording device within a recorded field. For example, a given pixel or pixels or locus or loci of a recording device within a visualized field may correspond to a single neuron, or several pixels or loci within a visualized field may correspond to a neuron, or a pixel or pixels or loci or loci within a visualized field may correspond to a cluster of neurons or a boundary zone between neurons, etc., or any combination of the foregoing, during a session when intracellular calcium rise induces bioluminescence that may be visualized and recorded. Information specific to each pixel or loci within the field may be individually recorded, e.g. by a computer to which a camera or other visualizing device is connected and to which such device transmits electronic signals determined by activity at given pixels or loci.

Over the course of a recording session, each pixel, at different time points, may receive no stimulation, owing to lack of bioluminescence emitted by the neuron, neurons, or area from which it is recording, or may receive some stimulation. Stimulation it does receive may be coded for (1) specific time points during a recording session during which it does receive or is receiving stimulation, (2) wavelength of bioluminescent emission it is receiving at said time points, and (3) intensity of bioluminescent emission of given spectra it is receiving at various time points. Such parameters of input per pixel or loci may be recorded in a session log, such as in a computer readable medium (e.g., flash memory, hard drive, etc.). A session log may contain parameters of pixels or loci of a recording field during a session. A session log may therefore contain a spatial map of activity in that spatial information, represented by a location of a pixel or loci, relative to other pixels or loci, within the field that receives bioluminescent stimulation may be recorded. A session log may also include a temporal map of activity in that temporal information, represented by when pixels or loci did and did not detect bioluminescent stimulation, for pixels or loci may also be recorded. A session log may also include a spectral map of activity in that bioluminescent spectral information, represented by wavelength, intensity, or both, or bioluminescent emission detected at pixels or loci at different time points during a session. A session log may thus include a spatiotemporal and spectral pattern of activity in a field across a session.

A spatiotemporal and spectral pattern of bioluminescent emission may thus include a data set indicating what frequencies of bioluminescence were emitted from positions (e.g., specific neurons or neural populations) at a given location or locations within a recording field at time points during a visualization or recording session. Time points may be identified in relation to an onset or offset of a particular stimulation, mental state, cognitive event or process, etc. Stimulation could be sensory (visual, auditory, olfactory, gustatory, tactile, or proprioceptive), chemical or pharmacological (e.g., following administration of chemical compounds to a subject or a subject's organs such as directly to neural tissue), or electrical stimulation such as directly to the nervous system. Electrical stimulation could also be applied to a subject's skin. In some examples, a human subject could self-report a mental state or cognitive process experienced during a recording session, or elicited in response to linguistic or other commands or other input given during a recording session.

During a recording session, before, during, and after a first stimulus application or state, emission spectra from a recording field, including when and where emissions are emitted and at what frequencies (i.e., spatiotemporal and spectral pattern), may be detected by a camera and a record of such spatiotemporal and spectral signatures recorded in a computer recording medium such as a computer memory, creating a session log containing a spatiotemporal and spectral pattern across a session, as disclosed. Upon exposure to a second stimulation or event (at a different time point from the first stimulation or event), a second spatiotemporal and spectral pattern may be detected. This pattern (e.g., spatiotemporal and spectral pattern) may also be recorded in a computer recording medium such as a computer memory, yielding another session log. Over a stimulus-recording session, or across multiple sessions, numerous such spatiotemporal and spectral patterns emitted in response to various stimulations may be recorded as spatiotemporal and spectral patters of session logs. As a pattern is detected, or after it is recorded, it may be compared with spatial, temporal, and/or spectral information contained in a recorded session log, detected and recorded during presentation of another stimulus or evocation of another state at a different time. The stimuli or state may differ with regard to the type, intensity, duration, or in other attributes. For example, they may be of different sensory modalities, or different types within a sensory modality, when sensory stimuli are used as stimulation events.

When spatiotemporal and spectral patterns of emission from session logs are compared, differences therebetween may indicate differences in the population of neurons that respond to the two stimuli that evoked the spatiotemporal and spectral patterns at issue. For example, different regions of a recording field may emit electromagnetic radiation at different times relative to application of a given stimulus, or the same regions but at different times relative to onset or offset of a given stimulus or stimulation session, or different emission spectra may be detected at a given place and time within a field, or all three of these variables may differ from one spatiotemporal and spectral pattern to another. Such differences may indicate differences in neural responsiveness to the stimuli presented. Conversely, where such variables do not differ from each other from one stimulus session to another, similarities in neural responsiveness to the stimuli may be indicated.

Detected patterns of neural activity recorded, for example, during applications of different stimuli or stimuli at different times or of different strength or magnitude, or combinations of variations of any of the foregoing, may be stored in a computer readable memory such as a hard drive, mobile storage medium, flash memory, or the like, or in combinations of more than one of the foregoing. Patterns recorded during one recording session may be recorded in the same computer-readable medium as that recorded during a second session, or in a different medium. One or more microprocessors within a computer or computer system may be configured to analyze natural activity patterns observed during different recording sessions and detect differences, similarities, or both therebetween. Similarities (i.e., indicia of activity from different observation sessions whose spatial and emission characteristics overlap with each other) may signify neurons that respond similarly to each other during the two sessions. Conversely, differences (i.e., indicia of activity from different observation sessions whose spatial or emission characteristics do not overlap with each other) may signify neurons that do not respond similarly to each other during the two sessions.

The one or more processors may be configured to process instructions for comparing data representing the spatiotemporal and spectral patterns of activity detected during observation sessions when neural activity is observed. In some examples, such data may have been stored in a computer-readable medium after each session and the spatiotemporal and spectral patterns of activity stored thereon analyzed by the one or more microprocessors. In other examples, incoming data representing spatiotemporal and spectral patterns of activity observed during a session may be compared to previously stored data representing spatiotemporal and spectral patterns of activity recorded during a previous session, for real-time comparisons. In either case, a computer system including computer-readable medium and one or more microprocessors would be necessary in order to interpret, analyze, and compare the volume of data generated during an observation session and discern between digitized representations of specific emission signatures emitted at specific loci in a recorded field of cells. Digital representation of minute differences of emission signatures and spatial location thereof, at specific time points during a session, require processing via one or more microprocessors, as does comparisons of observed activity between observation sessions.

In some examples, neural activity in response to a modality or example of a given sensory stimulation might be detected and recorded, followed by a second session intended to replicate the neural responsiveness induced by such sensory stimulation. For example, a particular visual stimulation might be applied and a spatiotemporal and spectral pattern of activity within visual cortex detected and recorded. Subsequently, activity of neurons within the visual system may be artificially stimulated such as electrically and the spatiotemporal and spectral response of the same field detected and compared to the spatiotemporal and spectral pattern recorded following application of the visual stimulation. Where the two spatiotemporal and spectral patterns differ from each other, differences in neuronal responsiveness to the stimuli may be indicated whereas similarities may indicate that the second stimulation recapitulated aspects of the visual stimulation.

In an example, bioluminescence of visual cortex following induced expression therein of bioluminescent polypeptides as disclosed herein may be visualized and recorded. During stimulation of the visual system such as by reception of light upon a retina, a spatiotemporal and spectral pattern of activity within a field of visual cortex may be detected and recorded. Different types or patterns of visual stimulation as reception of light on different parts of the retina or differently oriented patterns of light on a retina or different types of movement of light stimulation across a retina may be administered across a recording session and captured as a spatiotemporal and spectral pattern of bioluminescent emission in a session log. In a subsequent session, other stimulation of the visual system may be administered. Bioluminescence emitted by the visual cortex may be visualized and recorded during this subsequent session. During such subsequent session, stimulation of pixels or loci within a recording filed at or across time points during the subsequent session, such as in relation to onset or offset of different stimulations of the visual system, by emission of bioluminescence at various frequencies and/or intensities, may result in generation of a spatiotemporal and spectral pattern of activity of the subsequent session. Such spatiotemporal and spectral pattern may be recorded in a session log of the subsequent session. During creation of such session log or after, the two session logs, one of the first session and one of the subsequent session, may be compared by a software system configured to process information from pixels or loci within the recording field during a recording session as recorded in a session log as a spatiotemporal and spectral pattern. Differences and similarities in which neurons or populations of neurons are active and at which relative time points, as exemplified by the spatiotemporal and spectral pattern evoked during a session, may indicate whether different or similar neural populations exhibited evoked activity in response to different stimulations of the visual system, respectively. In this example, the visual system is given as one possible, non-limiting embodiment. As described above, however, similar spatiotemporal and spectral patters may be generated and recorded as a session log in response to any of a variety of stimuli or evoked state according to a particular application of the present disclosure.

EXAMPLES

The following examples are intended to illustrate particular embodiments of the present disclosure, but are by no means intended to limit the scope thereof.

FIG. 1 shows bioluminescent spectra of a polypeptide with an amino acid sequence corresponding to SEQ ID NO:13 sampled in response to saturating calcium (200 mM) at room temperature with 100 ms integration time on Ocean Optics QE65000 after overnight incubation in Coelenterazine-H.

Figure 2A:
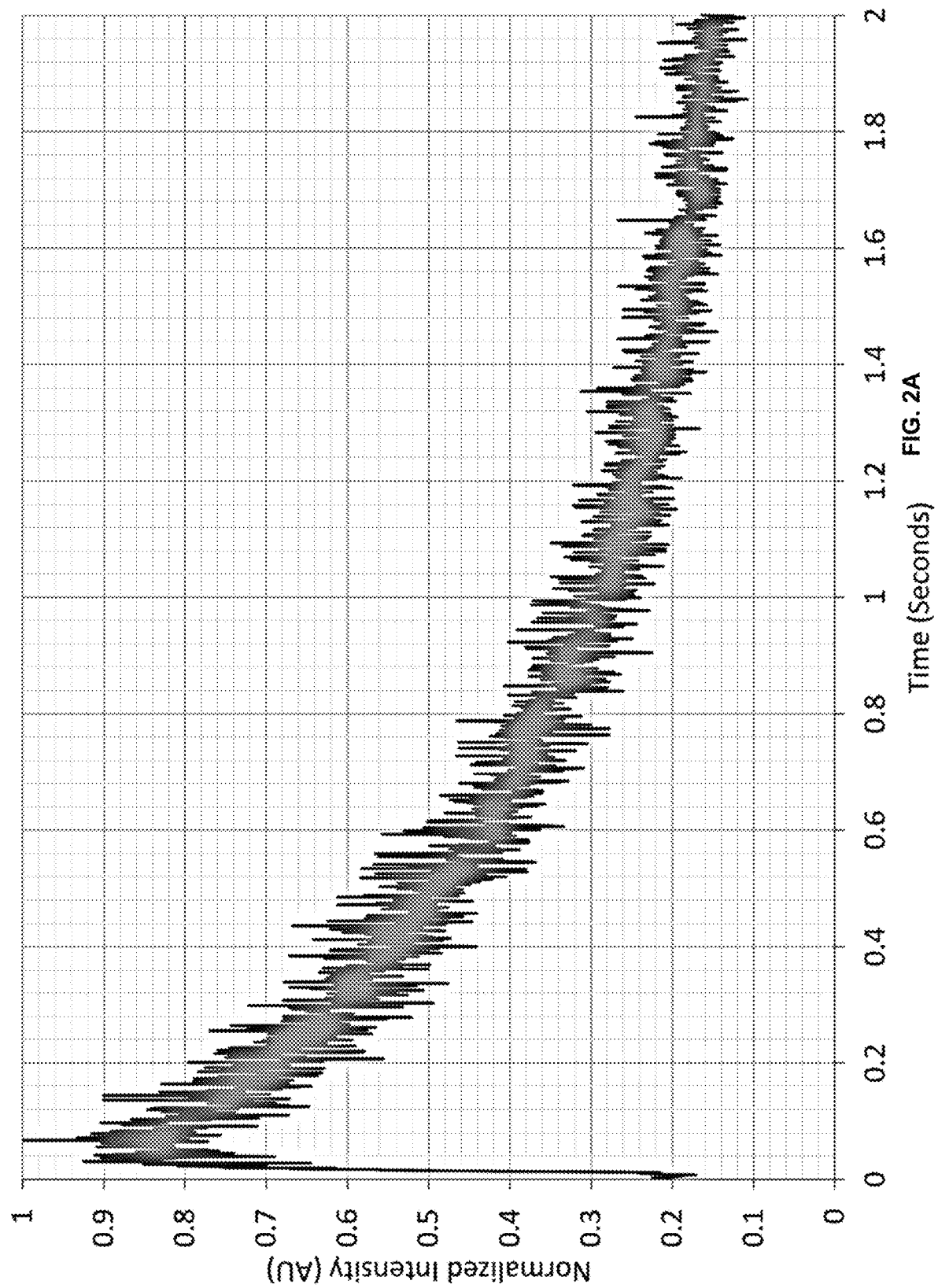
FIG. 2A and FIG. 2B show a rise/decay plot in response to saturating calcium for SEQ ID NO:13.
Figure 2B:
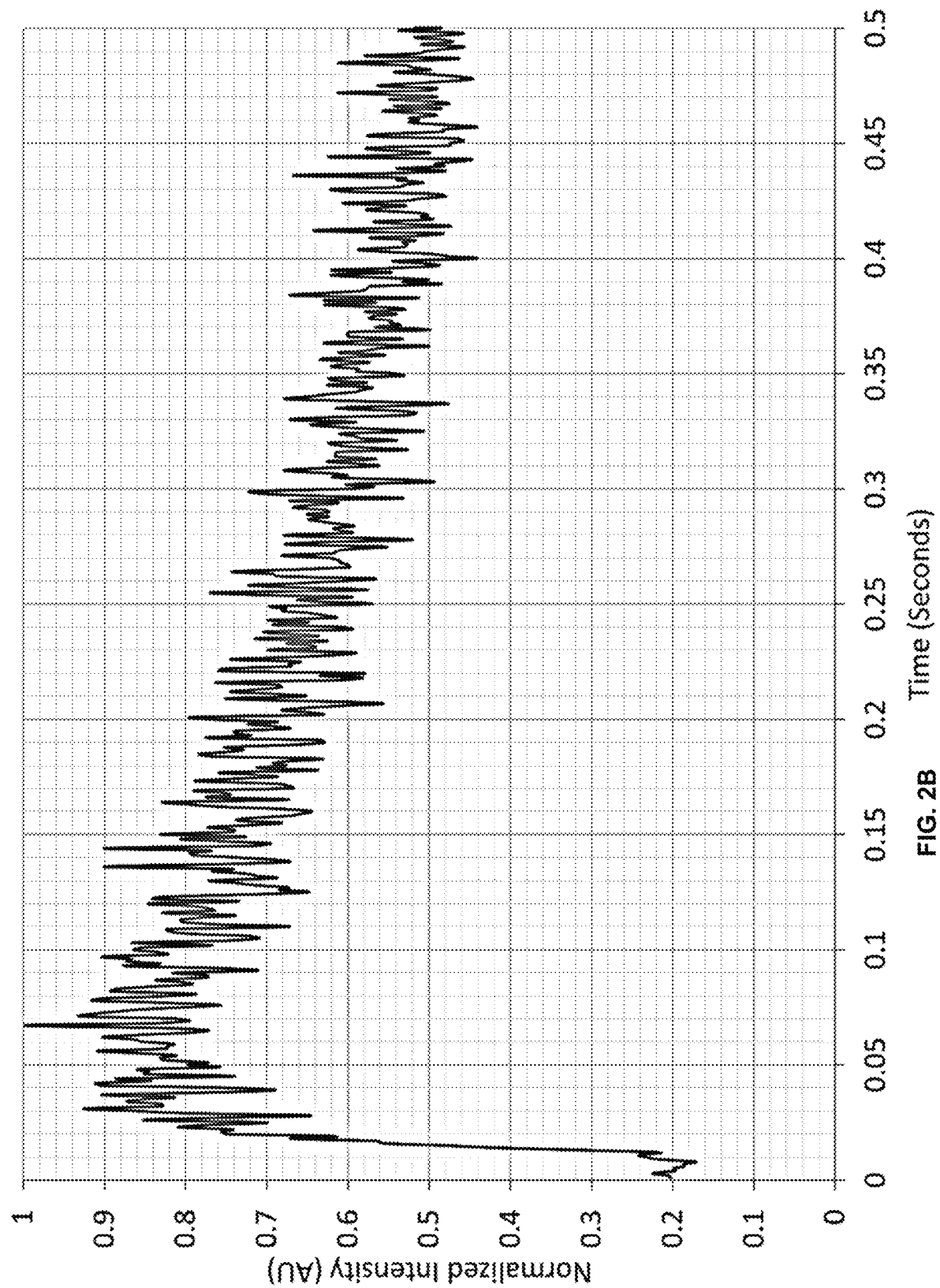

FIG. 2A and FIG. 2B show kinetic rise/decay data collected on SFM-400 stopped flow mixer in response to saturating calcium. A polypeptide with an amino acid sequence corresponding to SEQ ID NO:13 was incubated overnight in CTZ-H, buffer exchanged to zero calcium buffer (to remove excess coelenterazine), and rapidly mixed with calcium to elucidate kinetic response (FIG. 2B is an axis zoom of FIG. 2A over the first 0.5 sec).

Figure 3:
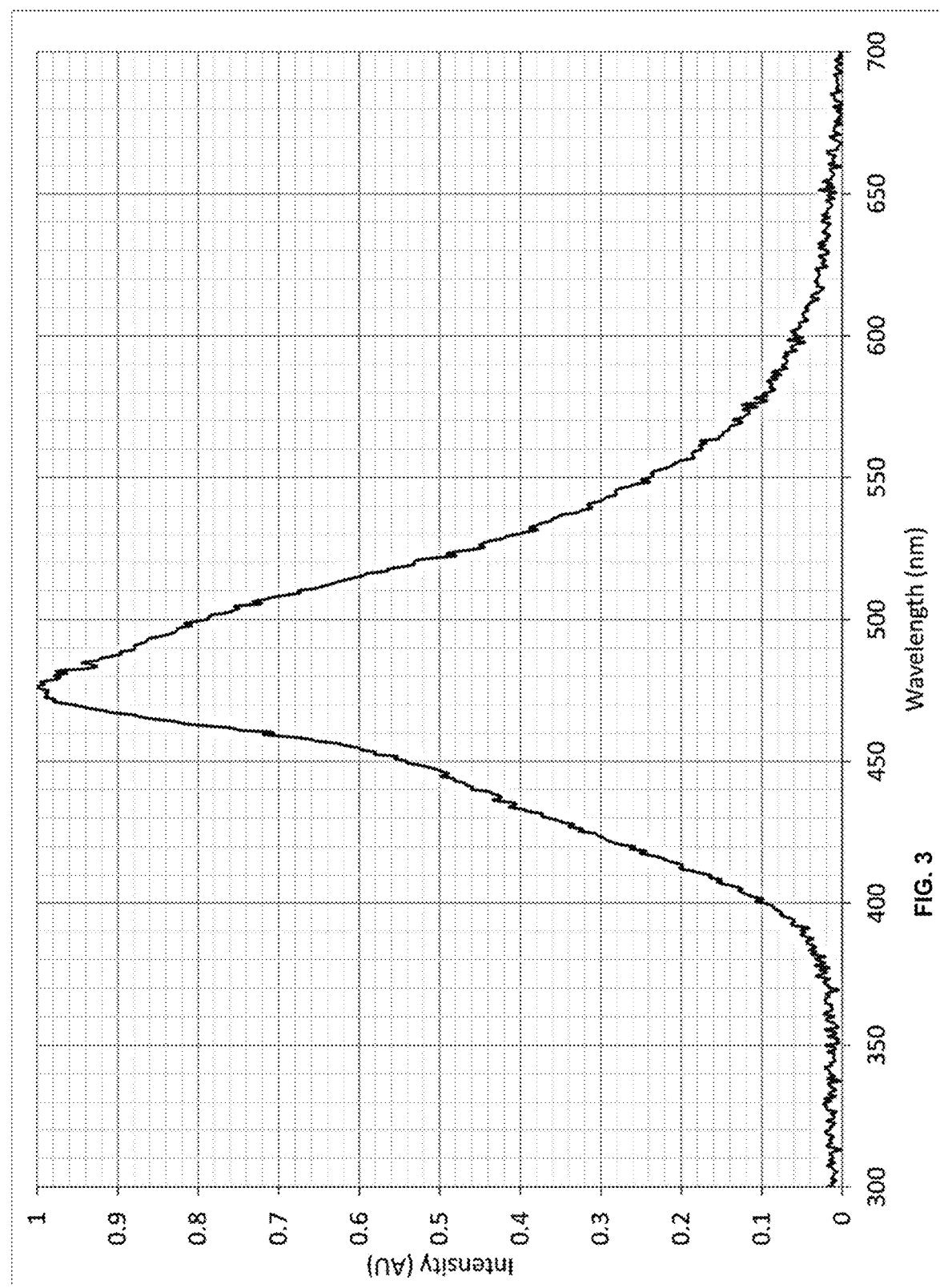
FIG. 3 shows bioluminescent spectra sampled in response to saturating calcium (200 mM) at room temperature with 100 ms integration time on Ocean Optics QE65000 after overnight incubation in Coelenterazine-H for a polypeptide with a sequence corresponding to SEQ ID NO:14.

FIG. 3 shows bioluminescent spectra sampled in response to saturating calcium (200 mM) at room temperature with 100 ms integration time on Ocean Optics QE65000 after overnight incubation in Coelenterazine-H for a polypeptide with a sequence corresponding to SEQ ID NO:14.

Figure 4:
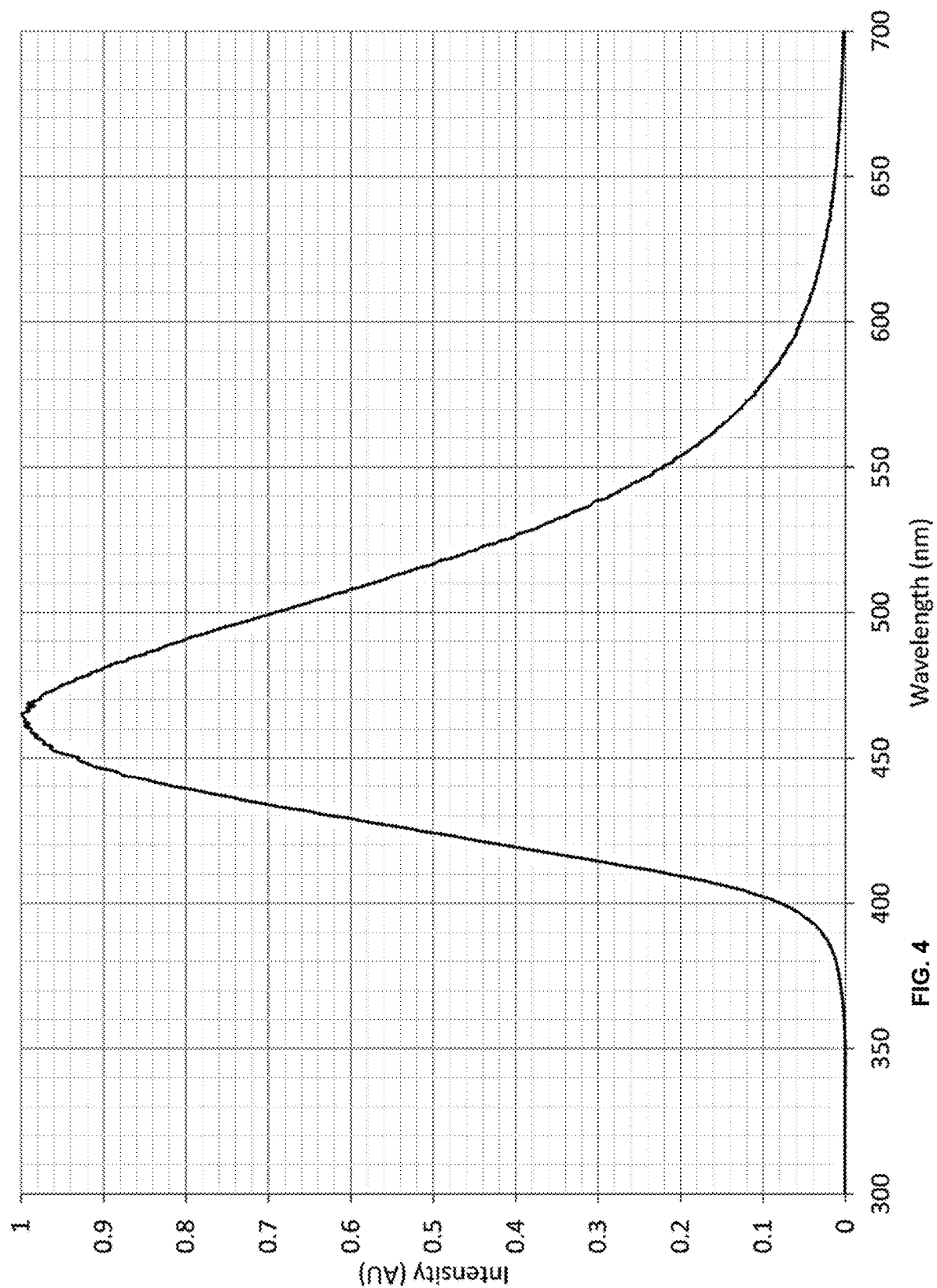
FIG. 4 shows bioluminescent spectra sampled in response to saturating calcium (200 mM) at room temperature with 100 ms integration time on Ocean Optics QE65000 after overnight incubation in Coelenterazine-H for a polypeptide with an amino acid sequence corresponding to SEQ ID NO:15.

FIG. 4 shows bioluminescent spectra sampled in response to saturating calcium (200 mM) at room temperature with 100 ms integration time on Ocean Optics QE65000 after overnight incubation in Coelenterazine-H for a polypeptide with an amino acid sequence corresponding to SEQ ID NO:15.

Figure 5:
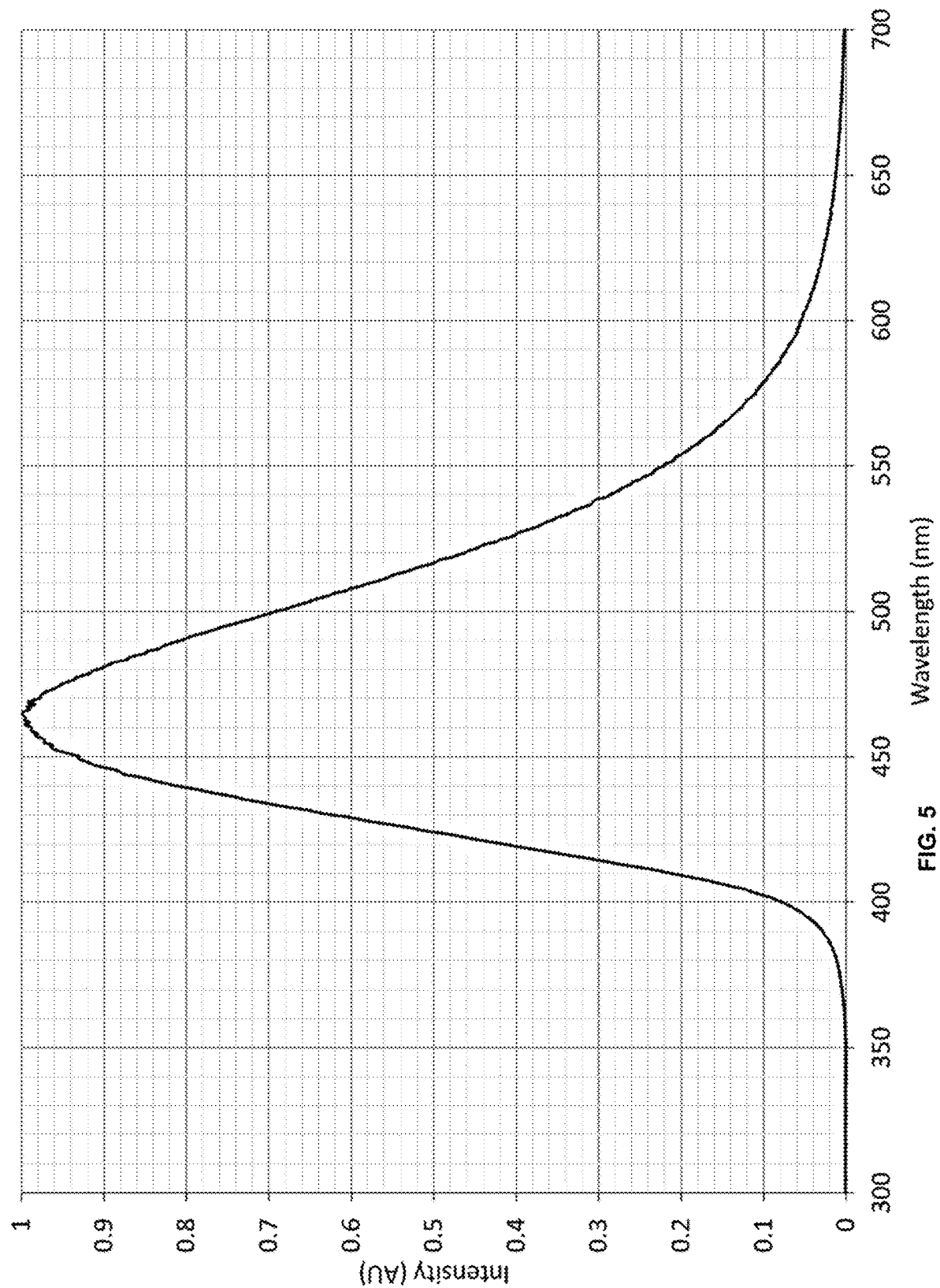
FIG. 5 shows bioluminescent spectra sampled in response to saturating calcium (200 mM) at room temperature with 100 ms integration time on Ocean Optics QE65000 after overnight incubation in Coelenterazine-H for a polypeptide with an amino acid sequence corresponding to SEQ ID NO:16.

FIG. 5 shows bioluminescent spectra sampled in response to saturating calcium (200 mM) at room temperature with 100 ms integration time on Ocean Optics QE65000 after overnight incubation in Coelenterazine-H for a polypeptide with an amino acid sequence corresponding to SEQ ID NO:16.

Figure 6A:
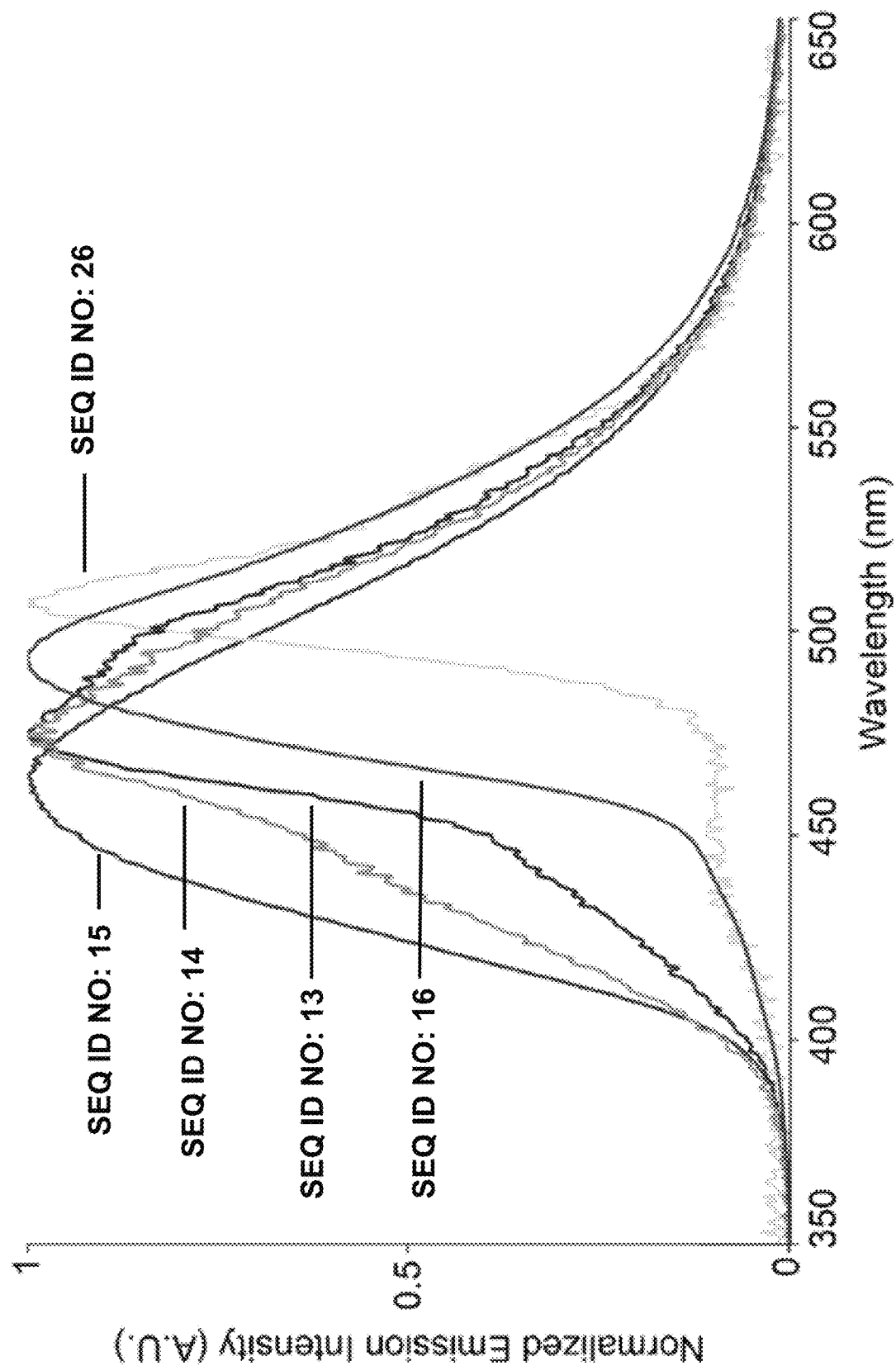
FIG. 6A shows a composite of bioluminescent spectra for polypeptides with amino acid sequences corresponding to SEQ ID NOs:13-16 and 26.

FIG. 6A shows a composite of bioluminescent spectra for polypeptides with amino acid sequences corresponding to SEQ ID NOs:13-16 and 26, illustrating differentiation of emission spectra amongst these examples. Cells expressing one or combinations of these bioluminescent proteins can be distinguished by their differences in emission spectra in response to calcium elevations. Spectra were sampled in response to saturating Ca2+ (200 mM) at room temperature with 100 ms integration (Ocean Optics QE65000) after overnight incubation with Coelenterazine-H. As shown in FIG. 6A, bioluminescent proteins as disclosed herein (e.g., those represented by SEQ ID NOs:13-16) showed notable blue-shifting relative to other bioluminescent proteins, such as with a sequence indicated by SEQ ID NO:26. Such blue-shifting was surprising, and not fully explained by Förster or other stable methods in Förster resonance energy transfer pairs. Without being limited to a particular function, one suggested explanation for such unexpected bleu-shifting that different variations in amino acid sequence amongst fusion pairs influences biophysical properties to blue-shift emission spectra.

Figure 6B:
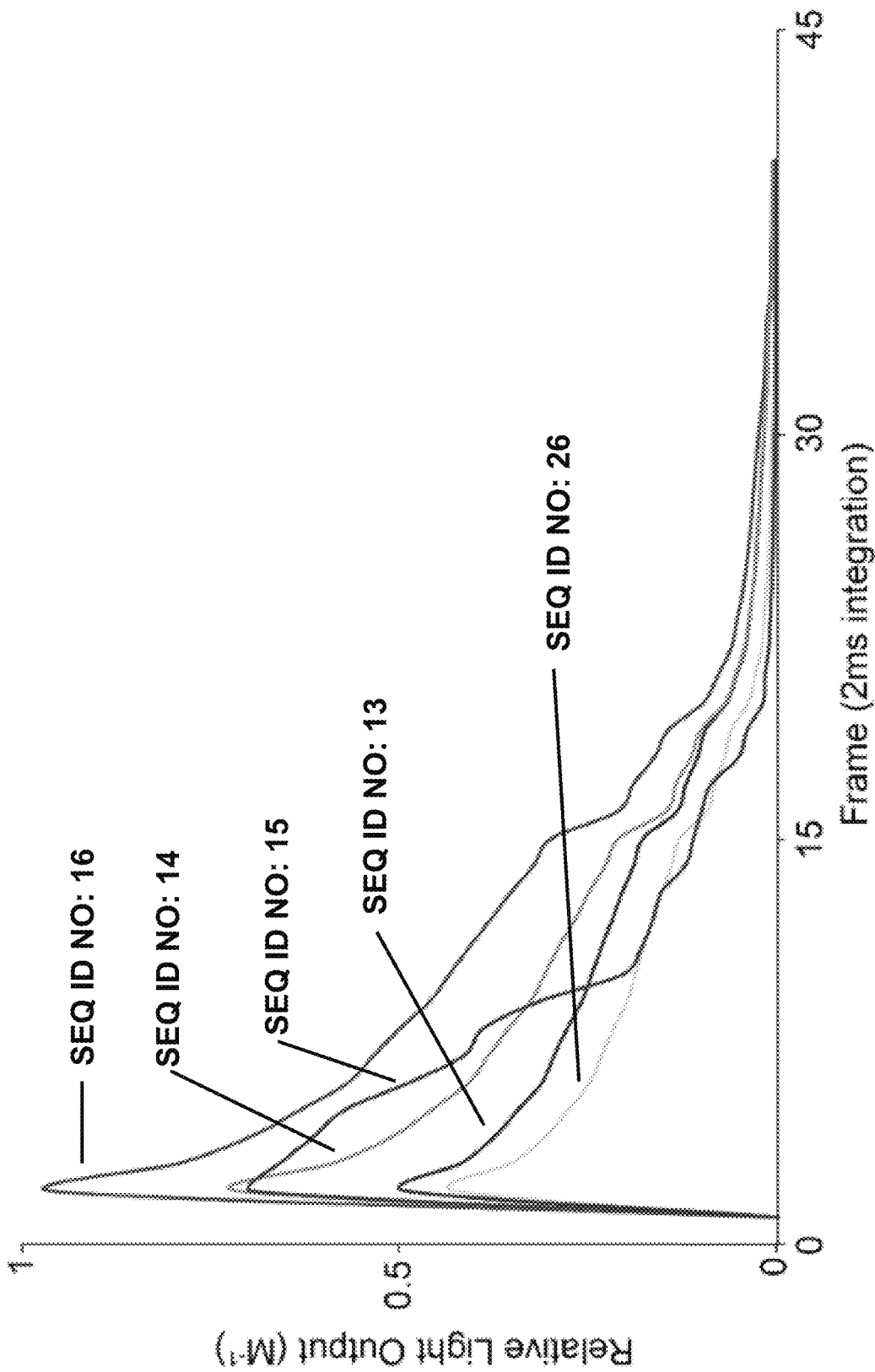
FIG. 6B shows relative light output normalized to protein concentration for SEQ ID NOs:13-16 and 26, expressed as a percentage output of SEQ ID NO:26.

FIG. 6B Shows relative light output normalized to protein concentration for SEQ ID NOs.13-16 and 26. Light output is calculated as mean gray value per frame collected with Basler AG CMOS camera; average of three trials. Total light collected over entire time course is stated as a (%) relative to SEQ ID NO:26. As disclosed herein, bioluminescent proteins having amino acid sequences represented by, for example, SEQ ID NOs:13-16 showed greater light emission relative to that of SEQ ID NO:26, indicated by their relatively higher areas-under-curve as indicated in FIG. 6B.

Viral Vector Injection for Indicator Expression

Individual strains of adeno-associated virus (AAV) viral vectors were packaged with a polynucleotide encoding a single color bioluminescent protein construct. In a sterile surgical preparation, the mouse is fixed onto a stereotax. A drill bit is used to create a burr hole in the skull to expose the surface of the brain. AAV vectors packed with individual polynucleotides encoding a single color bioluminescent protein construct are either individually or mixed with other colors and injected with a glass pipette into the rodent barrel cortex which is 3.5 mm lateral to bregma and 1.5 mm posterior to bregma. A bolus (100 nL to 1000 nL) is injected about 400 μm in depth. The mouse is sutured and following chronic protocols, administered drugs to facilitate healing and prevent inflammation.

In Vivo Imaging and Bioluminescence Measurement

After approximately three weeks during which time neurons are transduced to express bioluminescent proteins, an acute imaging experiment was performed. In an acute surgical preparation, a craniotomy about ~3 mm in diameter was performed, centered over the barrel cortex. Coelenterazine, the cofactor required for bioluminescence, is injected with a glass pipette into the barrel cortex, in the same region that the virus was previously injected into. Coelenterazine is also applied topically and gel foam is placed over the surface of the brain to prevent the surface from drying out. In a dark room, coelenterazine is allowed approximately one hour to reconstitute. The mouse is then brought into the imaging facility and an electric stimulator is attached to the whisker pad. Using a non-imaging modality, augmented from optics typically used in 2-photon excitation fluorescence microscopy (2-PEF), light emitted from the rodent brain in response to stimulus is spectrally separated and detected on photomultiplier tubes (PMTs).

Tissue Processing and Histology

In order to prepare the tissue for histology, the mouse is perfused via a transcardial perfusion. At the conclusion of an imaging experiment, brain tissue is removed and immersed in fixative. The fixed brain is sliced into 70 um slices and mounted onto slides for 1-photon imaging.

Results

Figure 7A:
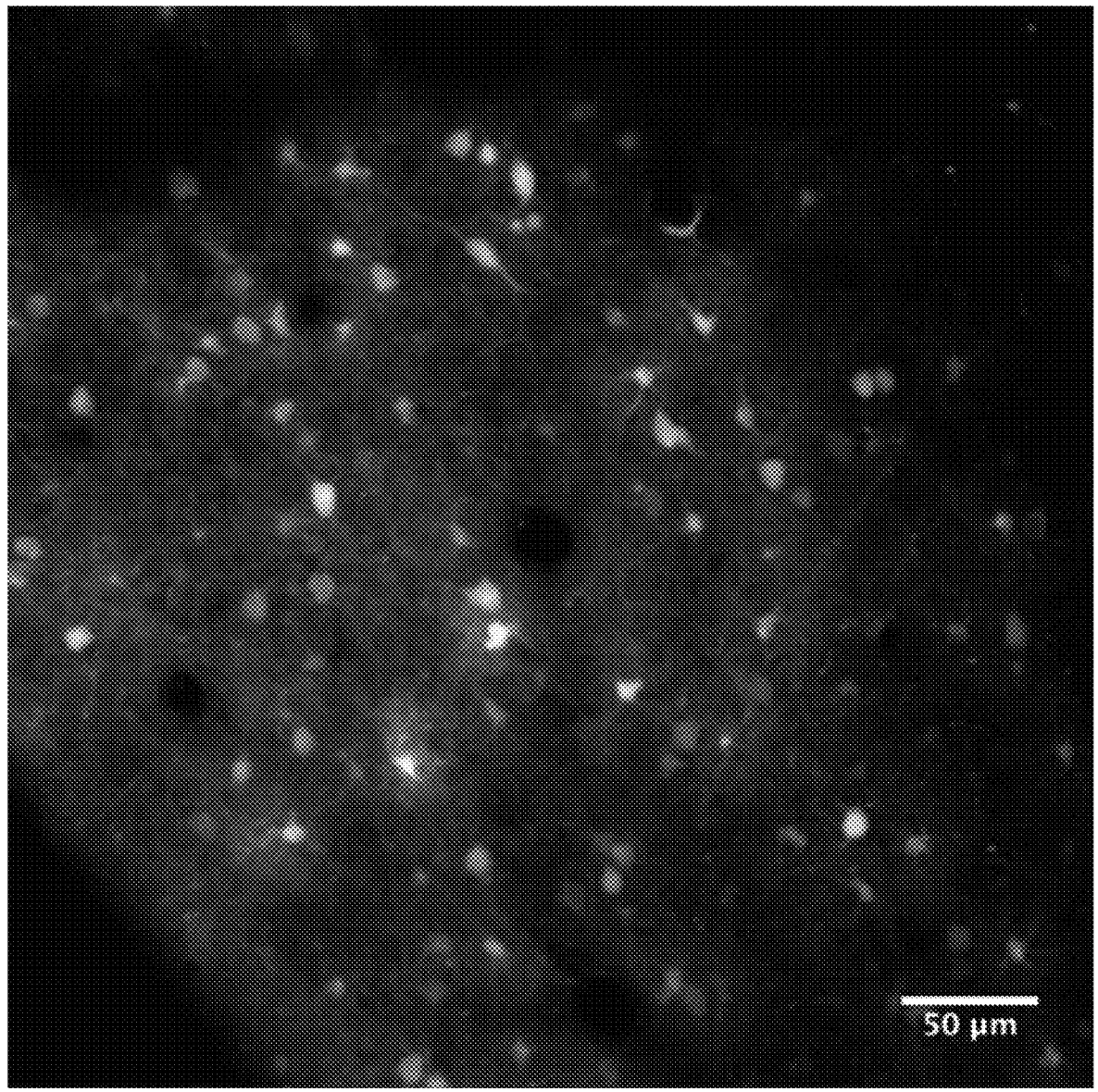
FIG. 7A shows a two-photon excited fluorescence (2-PEF) microscopy image of neurons expressing different bioluminescent protein constructs as disclosed herein and FIG. 7B is a 3-dimensional plot showing RGB intensity of neurons shown in FIG. 7A.
Figure 7B:
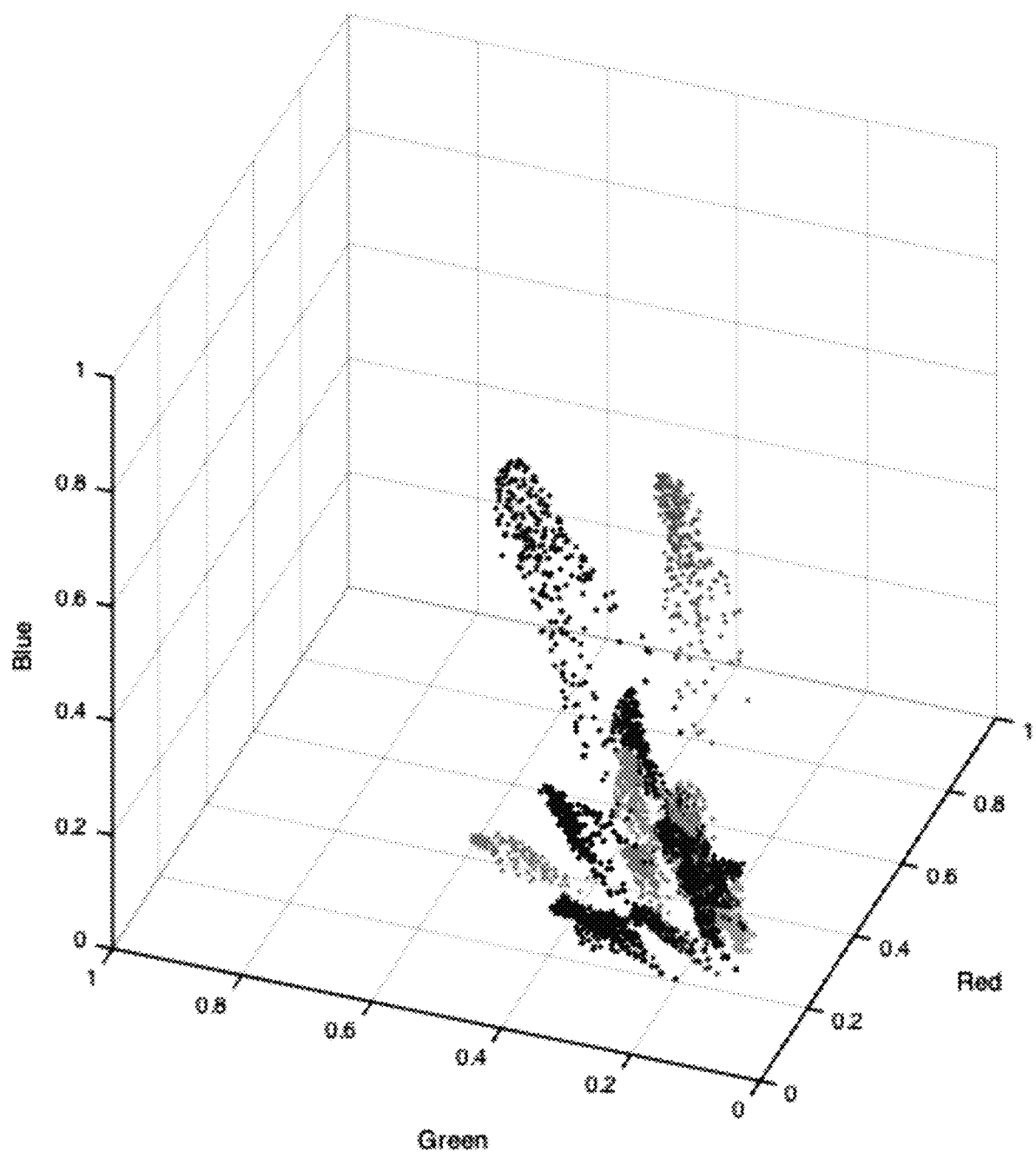

Mixing and co-injecting multiple AAV vectors, each encoding a single color, produced stochastic and varied transduction profile in cortical neurons Both individual and mixes of AAV vectors packaged with different bioluminescent proteins that bioluminesce at different frequencies in response to elevated calcium levels were injected into mouse models to test for expression amounts and patterns. For mixtures of colors, each vector contained $2\times10^{11}$ GC/mL. Injecting a mixture of colors resulted in individual cells with distinct spectral patterns. Shown in FIG. 7A is a two-photon excited fluorescence (2-PEF) microscopy image of mouse cortex showing fluorescence of transfected cells in response to fluorescent stimulation (as opposed to activity-induced calcium increase), demonstrating that different cells emitted different frequencies of florescence due following transfection due to stochastically differential expression in different neurons of bioluminescent proteins. FIG. 7B shows a 3D plot of RGB intensity of neurons shown in FIG. 7A demonstrating their differential emission levels.

Figure 8A:
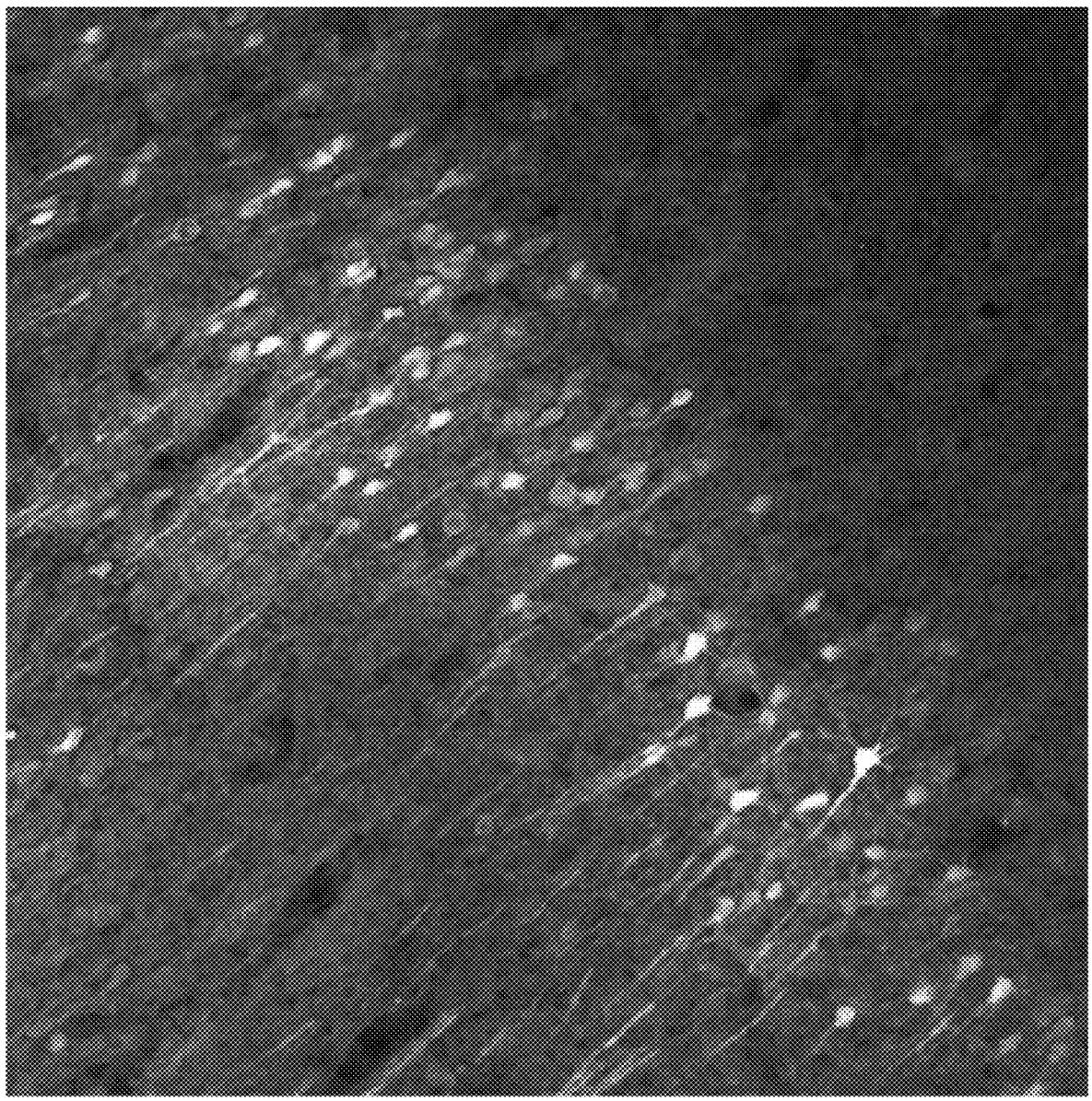
FIG. 8A shows histological data of mouse barrel cortex following transduction of neurons expressing multiple different bioluminescent proteins and FIG. 8B shows RGB intensity levels of 15 neurons from FIG. 8A.
Figure 8B:
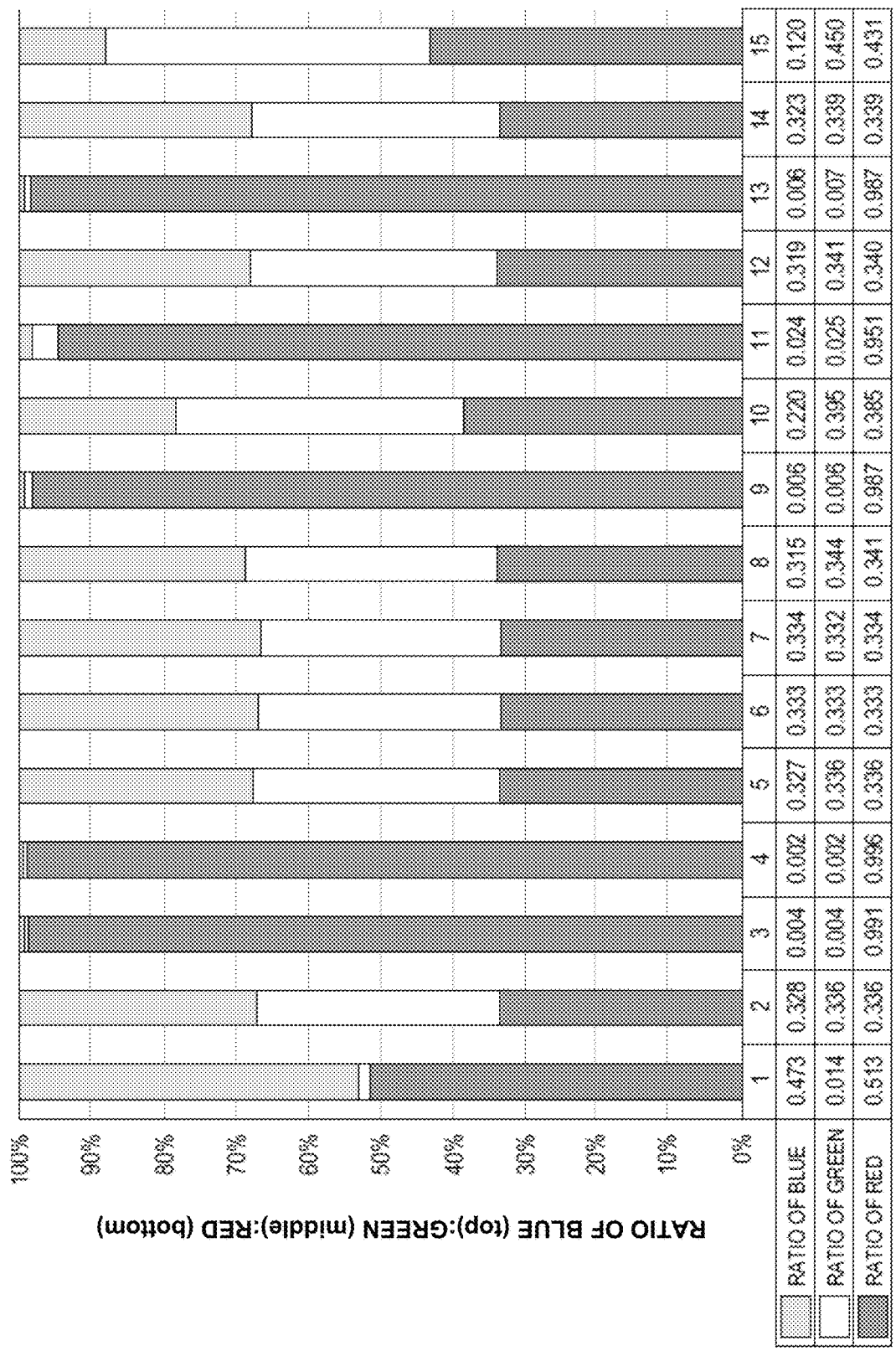

In the example in FIG. 8A, a mouse was co-injected with four different AAV vectors with different bioluminescent proteins and the neurons were allowed 3 weeks to transduce. An acute craniotomy was performed and stimulus triggered bioluminescent data was acquired. The mouse was then perfused and histology was performed to reveal the expression pattern. Neurons were identified as regions with higher intensities. The image shows that neurons are uniquely and stochastically labeled. The ratio of the fluorescence from different color indicators in each cell is displayed in FIG. 8B. The ratios of three different emission channels measured within neurons varied between cells, with several cells showing distinct patterns in color.

Neural activity-dependent bioluminescence in a seizure model.

Applying pentylenetetrazole (PTZ) topically induces a seizure in the mouse cortex that can be recorded optically, demonstrating for the first time that the mouse brain can fluoresce from stimulated neural activity. PTZ causes chemically induced seizures. During seizure activity, the bioluminescent protein constructs released photons that were collected by the PMTs in the presence of coelenterazine. For the first time, it was shown that the rodent brain could emit in vivo detectable bioluminescence from neural activity.

Figure 9:
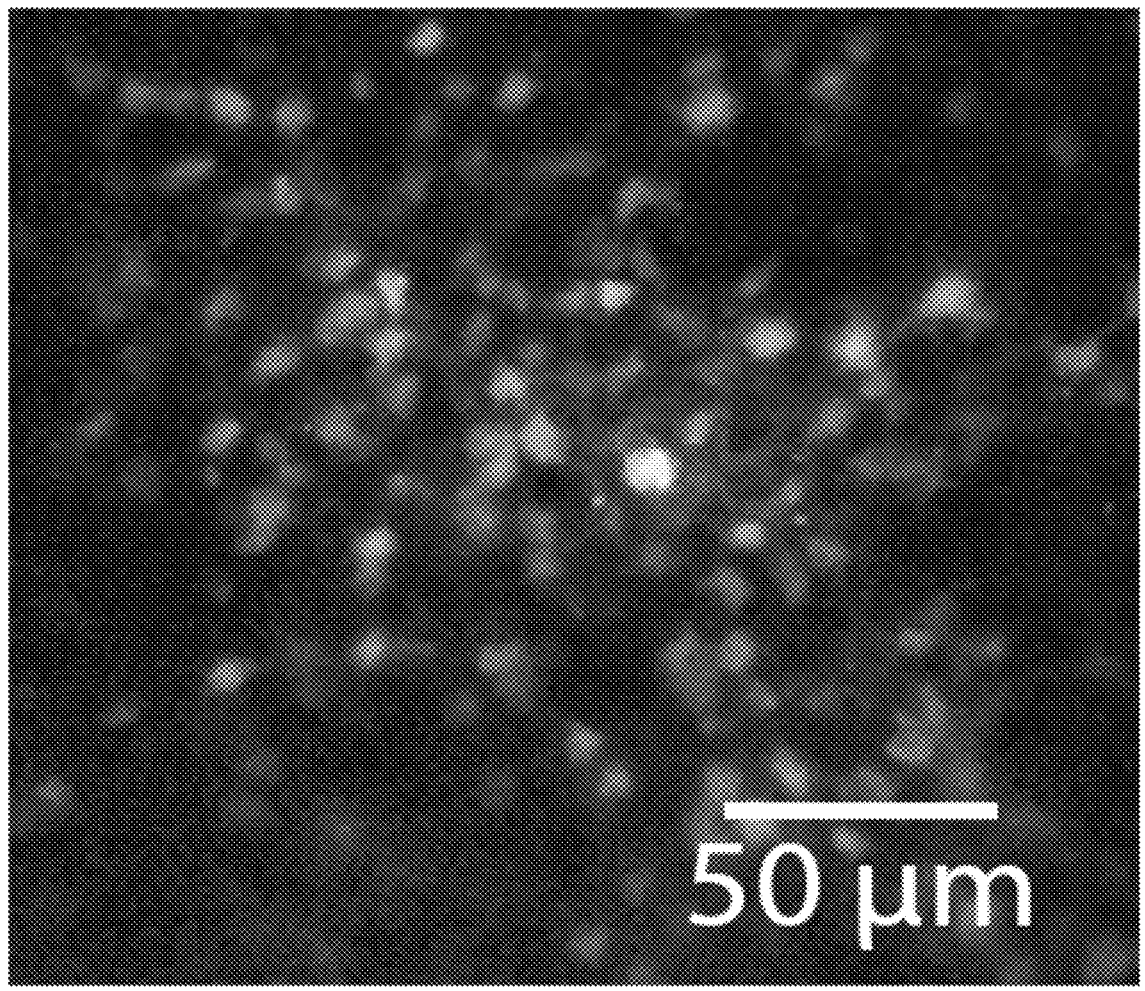
FIG. 9 shows a 2-PEF microscopy image of neurons in the mouse cortex expressing different color bioluminescent proteins.
Figure 10:
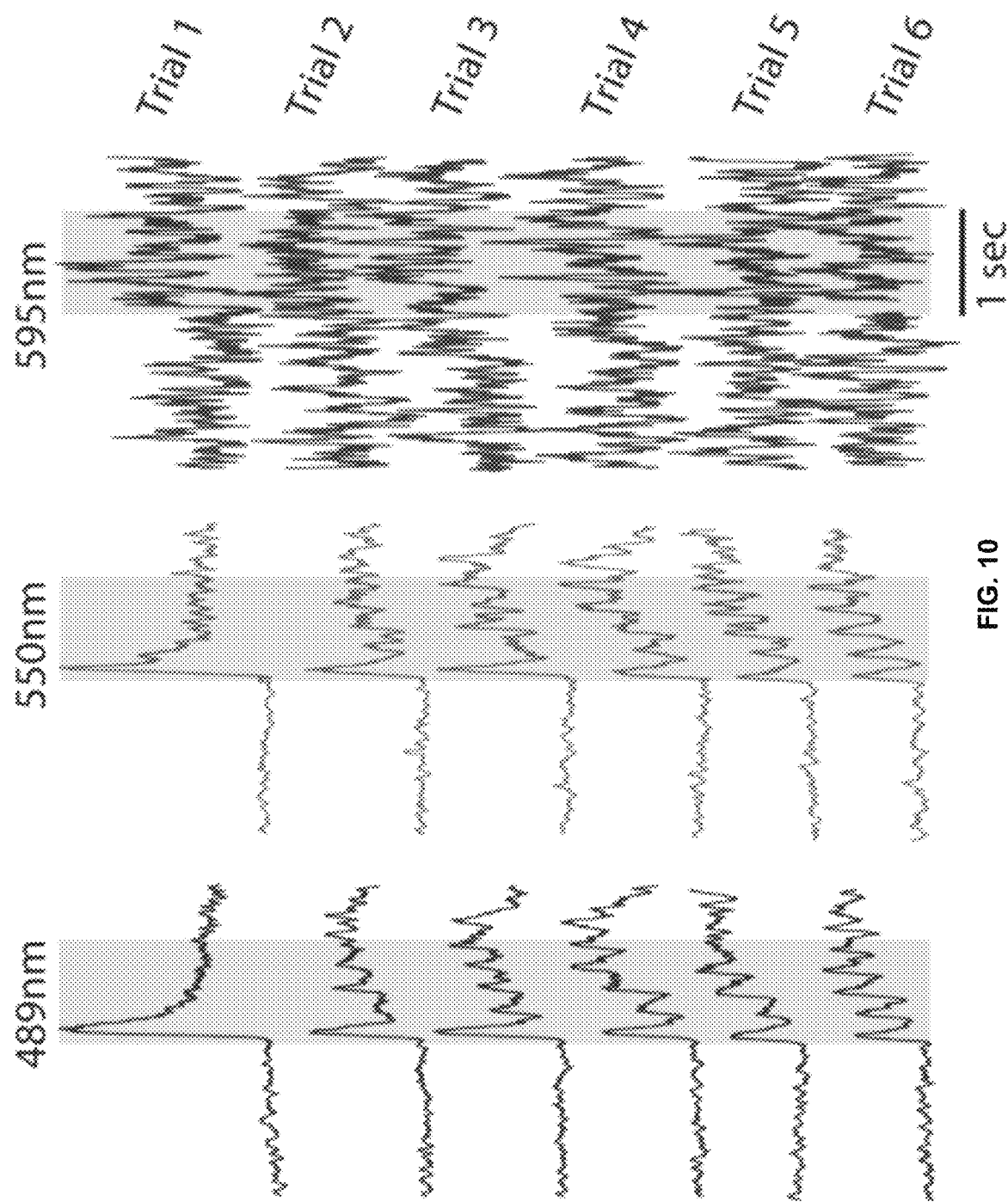
FIG. 10 shows stimulus-triggered neural activity in mouse barrel cortex neurons following transfection with AAV vectors driving expression of three different bioluminescent proteins.

Somatosensory Stimulation-Evoked Neural Activity Reported by Multicolor Bioluminescence In another anesthetized mouse, a stimulation of the whisker pad produced light emissions at multiple wavelengths. Approximately three weeks after the virus injection, an acute craniotomy was performed on the mouse to reveal the surface of the barrel cortex, where three AAV vectors driving expression of different bioluminescent protein had been injected. A 2-PEF microscopy image of neurons in the mouse cortex expressing different color bioluminescent proteins is shown in FIG. 9. Coelenterazine was injected and allowed to reconstitute within the brain at which point an electric stimulator was attached to the mouse whisker pad. Stimulating the whisker pad at 10 Hz resulted in neural activity in the barrel cortex, as indicated by bioluminescent signals collected. Across a number of trials, the same stimulation of the whisker pad resulted in emissions of light with similar temporal and spectral shapes (FIG. 10).

Figure 11:
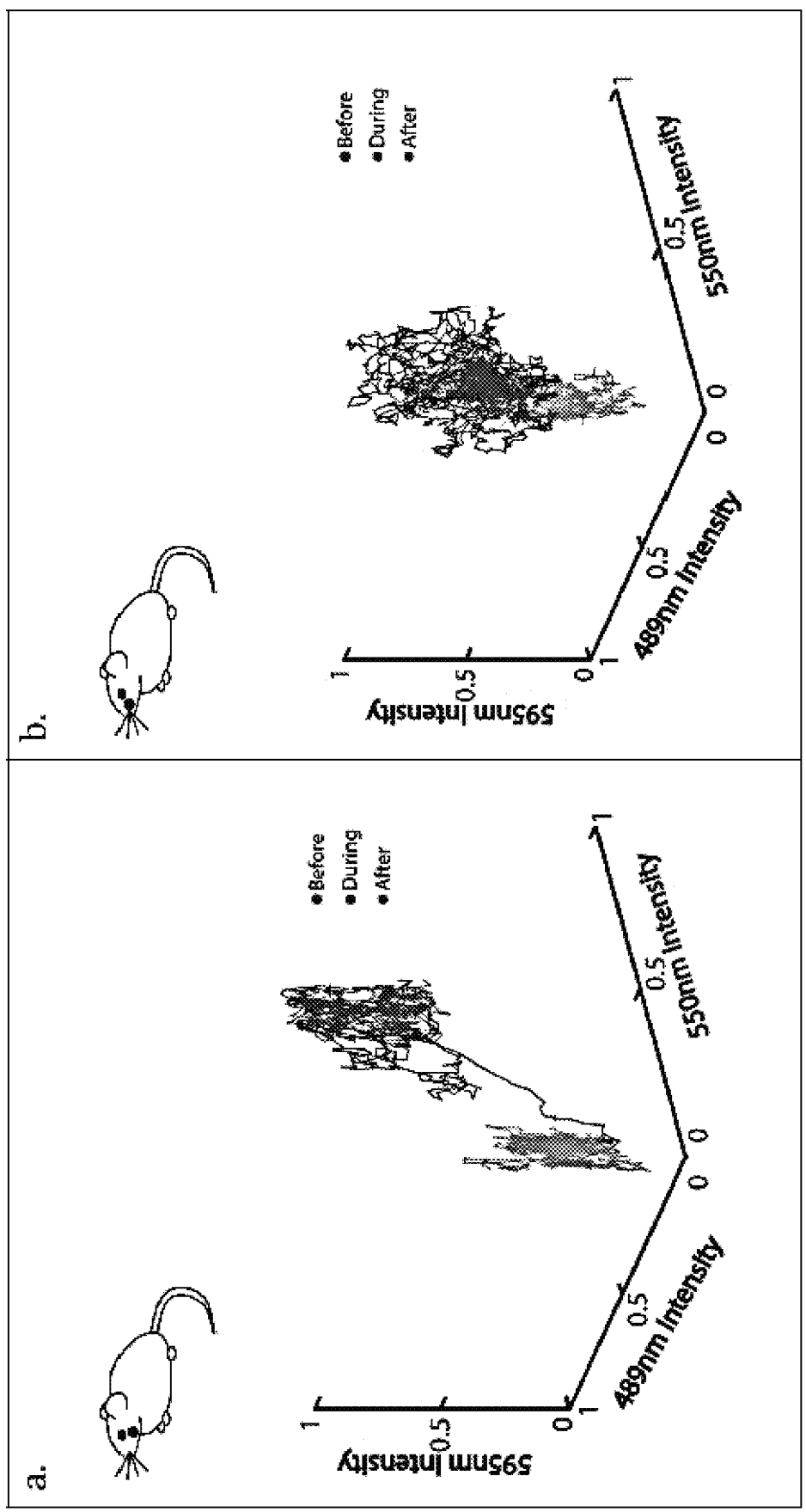
FIG. 11 shows light emission of three different colors in 1-second epochs before, during, and after shock to the whisker pad with electrodes in two different locations (a and b) in mouse barrel cortex following injection with AAV vectors driving expression of three different bioluminescent proteins.

Relocating the Location of Stimulus on the Whisker Pad Resulted in Different Patterns of Neural Activity that was Repeatable For measuring stimulation-evoked activity, stimulus electrodes were initially placed on one area of the whisker pad. The stimulus electrodes were then moved to a slightly different position on the whisker pad and the same shock stimulus was applied again. In both instances, when the intensity of each emission channel is plotted on a separate axis, the emission from one second epochs before, after, and during the stimulus resulted in clearly different color combinations. As expected, moving the area of stimulation on the whisker pad resulted in different spectral and temporal light emissions. Shown in FIG. 11 is light emission in 1-second epochs before, during, and after shock to the whisker pad with electrodes in two different locations (a and b). Each trace is a stimulus triggered average of 5 trials where the intensity in the three different emission channels is plotted as a single point and sequential points are connected. Moving the area of stimulus (a) to another area of stimulus (b) affected the patterns of neural activity in the barrel cortex.

Methods

Surgical Procedure for Burr Hole Injections

A drill is mounted into a micromanipulator over the field. A micropipette loaded with a viral vector for driving expression of bioluminescent polypeptide is loaded into a micromanipulator. Mice are anesthetized under 5% isoflurane at the site of the drill and maintained at 1.5-2% isoflurane in 100% oxygen for the duration of the surgery. Mice are injected with ketoprofen (2 mg/mL at 2.5 uL/g of mouse) and dextamethasone (0.1 mg/mL at 2 uL/g of mouse) subcutaneously. Then mice are injected with atropine sulfate (0.15 mg/mL at 3.3 uL/g of mouse) intramuscularly. Mice are then mounted on a stereotax for intracranial injection. Bupivacaine (0.125%) may be injected subcutaneously over the incision site.

Holes are drilled in the exposed skull at the pre-determined stereotaxic coordinates to expose barrel cortex. Viral vectors are then applied to the exposed cortical tissue via micropipette, at a depth of, for example, ~500 um deep. Mice are then sutured and recovered from anesthesia. Transduction is allowed to occur for the next 14-21 days before imaging.

Imaging and recording of bioluminescence is performed 21 days after injections to allow for expression of the bioluminescent protein. Skin over the injection site is removed and skull exposed. An approximately 4 mm diameter circle is drilled around the injection site and the skull flap removed. Gel foam is wet with coelenterazine and placed over surface of the brain to reconstitute for at least an hour, prior to imaging. Electric stimulus is then attached to the whisker pad region of the mouse and bioluminescence detected by PMT apparatus in response to various trains of stimulation.

Histology

Mice were perfused transcardially immediately following imaging session with 1×PBS and 4% Paraformaldehyde (PFA). Brains were removed and stored in 4% PFA for an additional 24 hours. Brains were transferred into 30% sucrose for at least 24 hours, or until the brain is saturated with the 30% sucrose, then repeated with 30% sucrose. Slices at 70 um thickness were taken and stored on Superfrost cover glass and imaged underneath 1-photo microscope and images captured with a fluorescent camera.

Non-Human Primate Transfections

The ability to discern multiple independent fluorescent signature emitted by cortical neurons in a field transfected with a plurality of vectors driving expression of fluorescent proteins was determined. The visual cortex of a macaque was injected with a combination vectors for driving expression of bioluminescent markers as disclosed herein. Rather than calcium-induced fluorescence, which requires coelenterazine infusion, the fluorescent protein portion of transfected constructs was detected using two-photon microscopy. Results confirmed that simultaneous transfection with a combination of markers permits detection of a large number of discernable signatures.

Injection Methods

Convection enhanced delivery (CED) was used to keep indfusate within the cortex rather than to allow the fluid to return back up the outside surface of the of the injection pipette's track. The AAVs contained multi-color fluorescent proteins, randomly mixed, and each injection site was precisely positioned, within ~0.5 mm of the target region, to optimize cortical filling with just 4-9 injections within a 3.14 cm2 region. The bolus was delivered at a rate of 1-5 µL/min to maintain high-dispersal while preventing pressure-induced tissue damage. A canula was positioned above the cortex, which targeted the positioning of each CED tube injection, 2 mm below the surface of the cortex.

Viral Solution Content

In the macaque whose data from primary visual cortex (VI) is show in FIGS. 12-15, the figure on monkey primary visual cortex (V1), we made four 40-504, injections of a mixed solution containing five multi-color fluorescent proteins were made.

Imaging Methods

Figure 12:
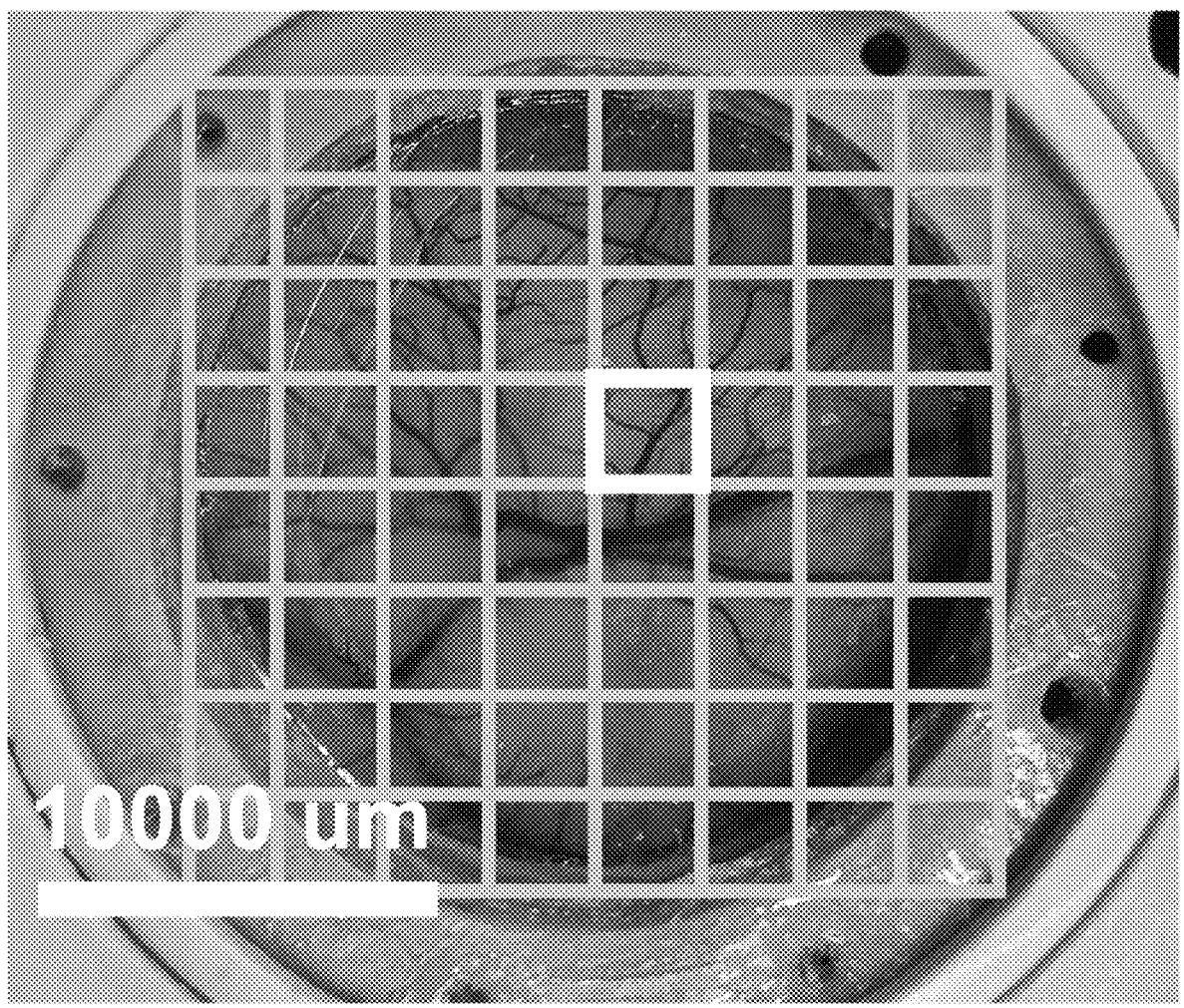
FIG. 12 shows a recording field of cortex of a non-human primate during visualization of fluorescence emitted by a combination of fluorescent proteins.
Figure 13:
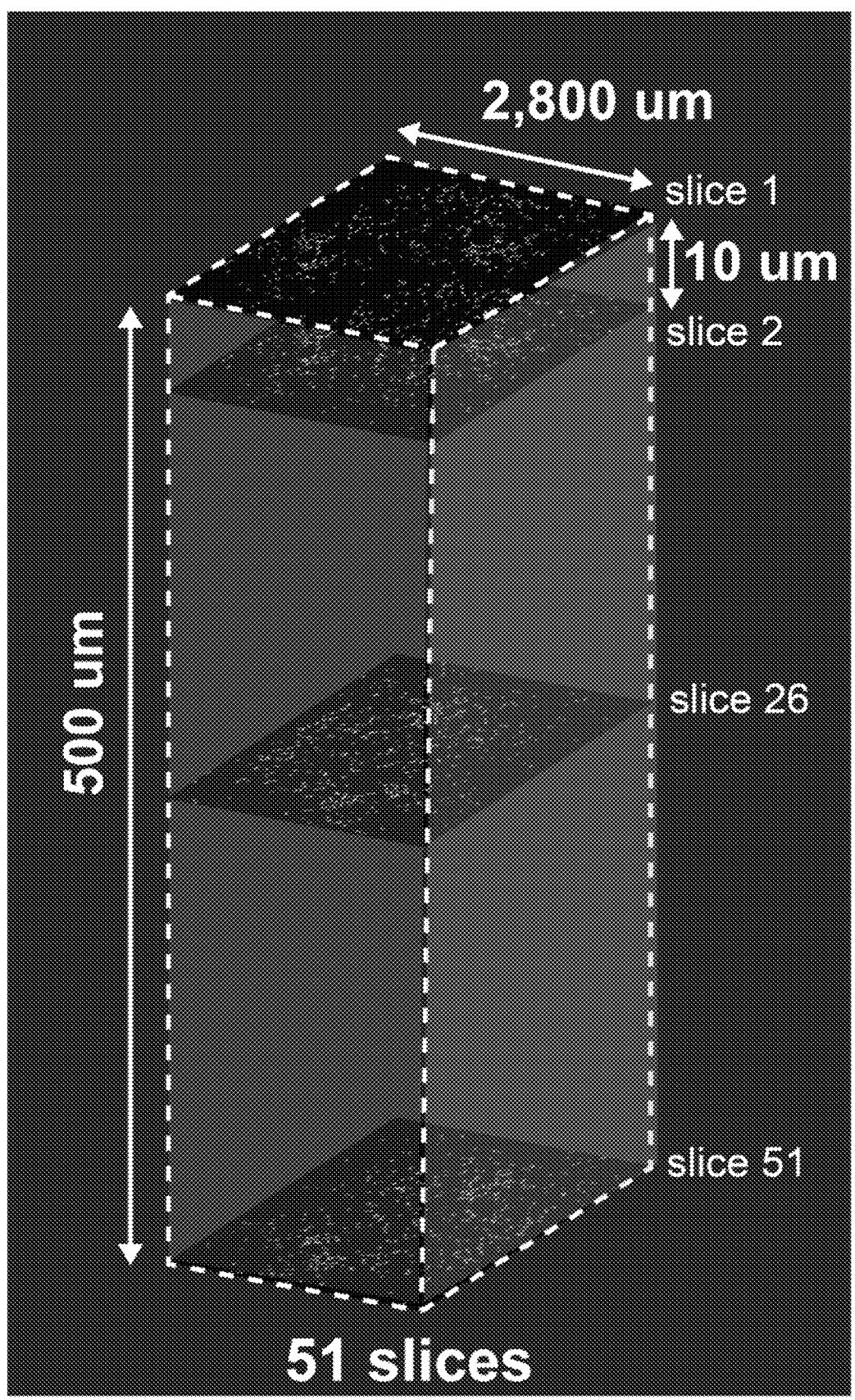
FIG. 13 is a representation of fields of recording at depths of up to 500 um below cortical surface during observation of neural activity.
Figure 14A:
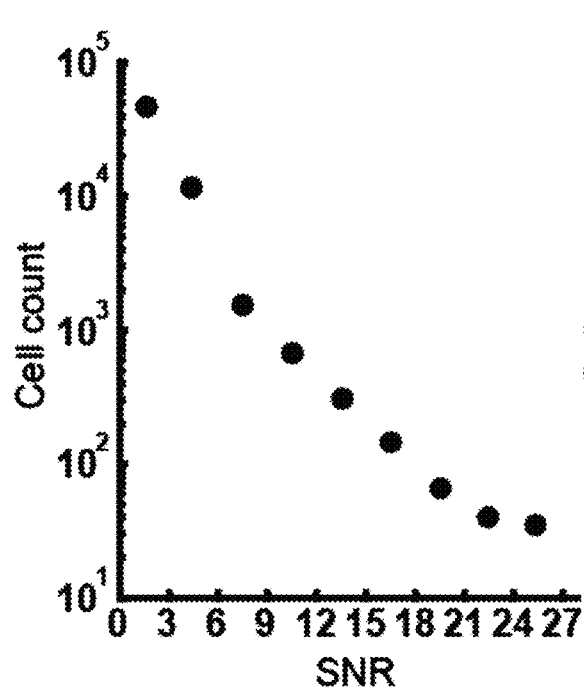
FIGS. 14A (red), 14B (yellow), 14C (green), and 14D (blue) show number of neurons exhibiting different signal-to-noise ratios of fluorescence at different wavelengths.
Figure 14B:
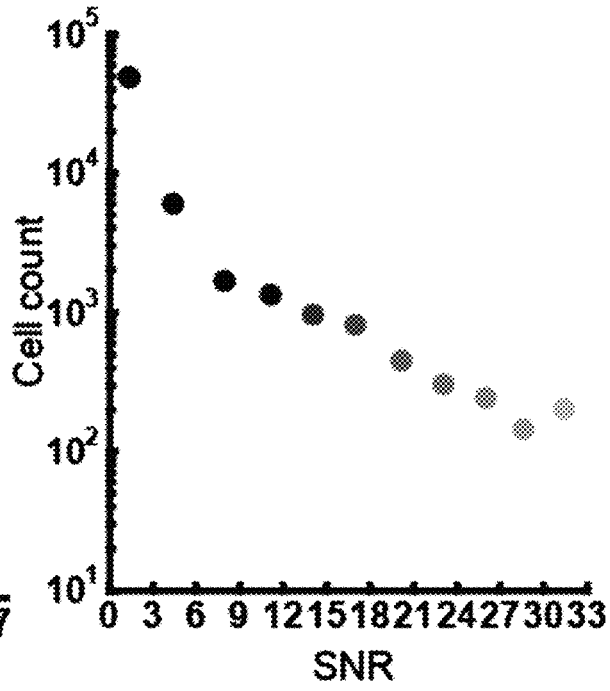
Figure 14C:
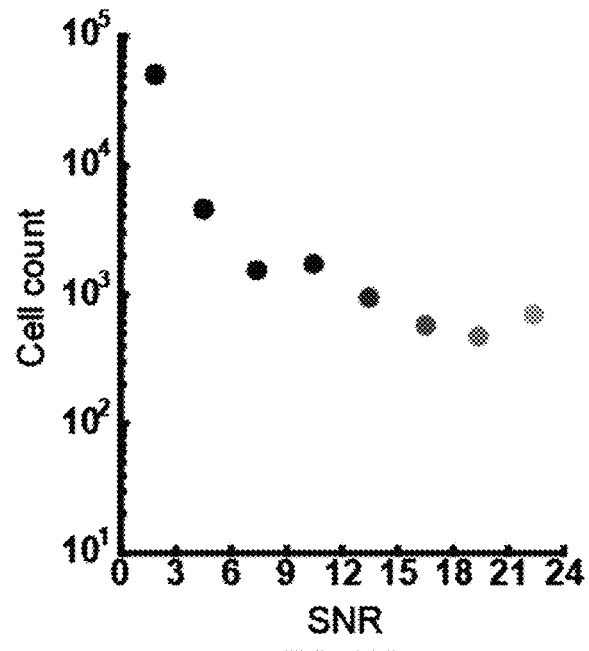
Figure 14D:
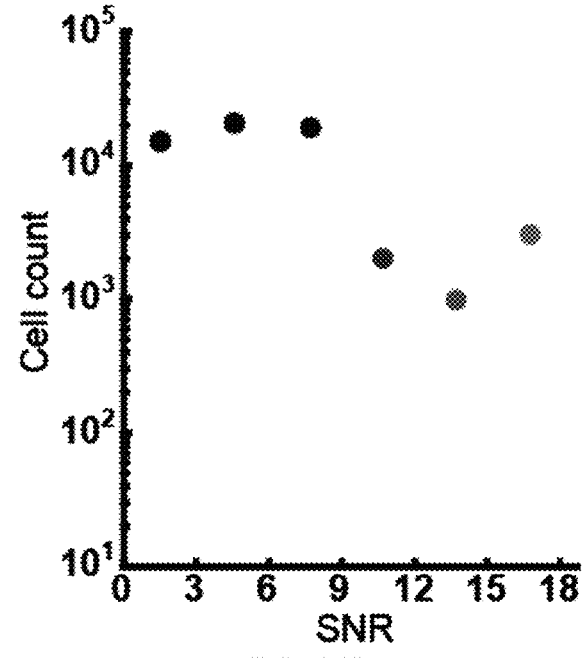
Figure 15:
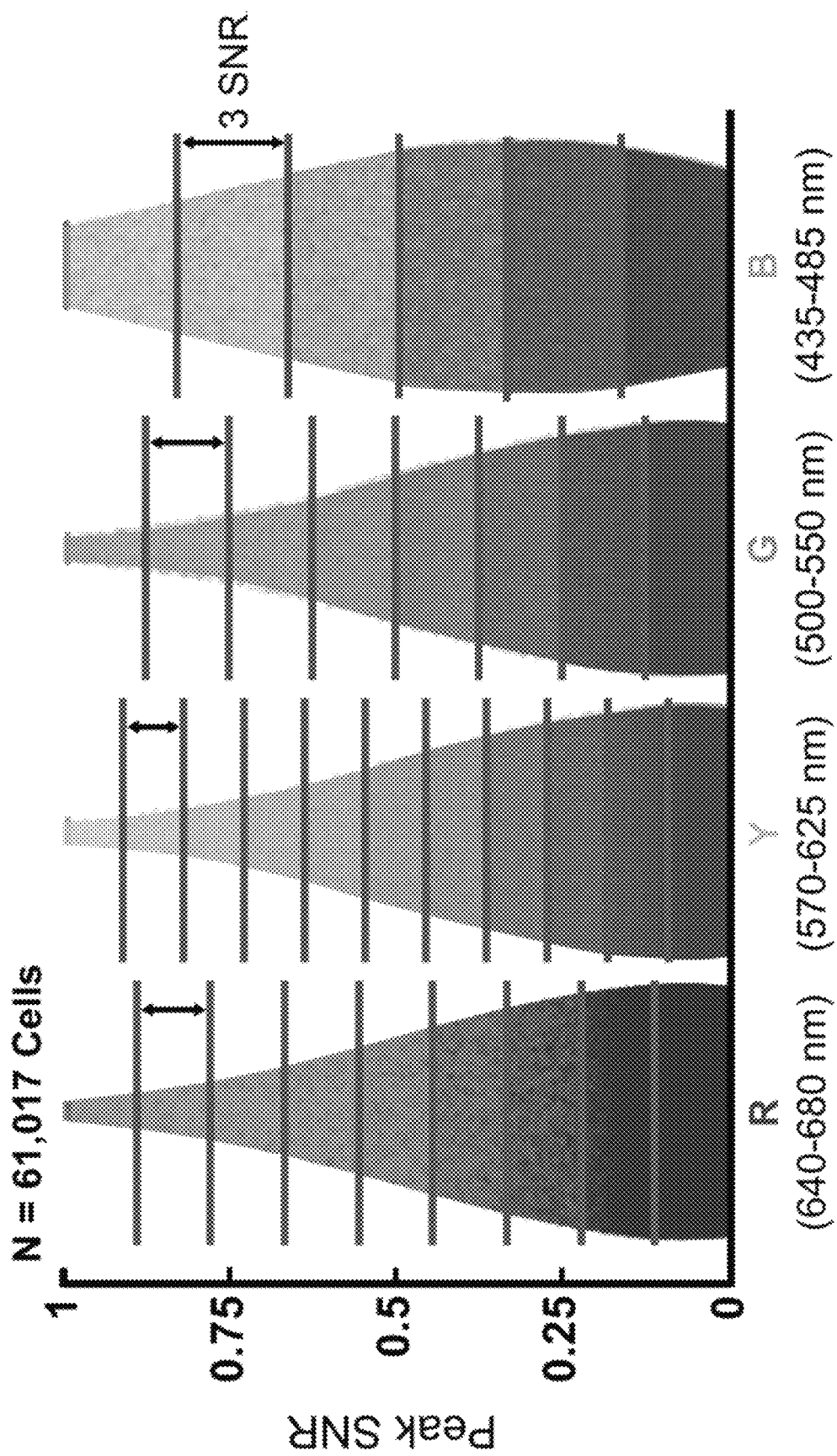
FIG. 15 shows violin plots of emission detected within given filtered spectra, with ratio of SNR of a cell to the highest SNR measured within given filtered spectrum, where width indicates relative number of cells.

Cells were imaged with a Bruker Ultima IV two-photon imaging microscope driven by a MaiTai HP DeepSee Ti:Saph laser at a wavelength of 830 nm. We captured an entire 2-cm diameter imaging window (3.14 cm2 area) was captured by tiling the window with 49 (7×7) grid of 500 µm deep z-stack scans (each stack 2.8 mm on a side), as shown in FIGS. 12 and 13. The z-stacks were computationally stitched into a single volume to visualize the ultra-large imaging window. 61,017 cells were imaged.

Analysis Methods

Cellular analyses were performed using Imaris software. Using the Spot Detection feature identified potential cell bodies were identified by the size of the image intensity regions. Background was calculated as an average of the mean intensity of pixels between spots. Each pixel was imaged with four photo-multiplier tubes simultaneously, each with a different color filter (Red, Yellow, Green, Blue), to determine a differential colorimetric measurement of each cell's emission spectra. Signal-to-noise ratio (SNR) was calculated as the quotient of the difference between the mean intensity of each candidate cell and the background mean intensity divided by the standard deviation of the background. SNR was calculated independently in each of the four acquisition channels. Cells were identified from the candidates that achieved an SNR of one of more in at least one channel.

Each cell had an array of the four colors and the profile was established of differentiable colors in each cell in bins of 3 SNRs, to ensure clear differentiability. Binning with 3 SNR resolution is a commonly used and arbitrary technique to distinguish levels of signal in a transmission channel in the field of engineering. By utilizing 3 SNR resolution here, at least 4,752 different colors of cells with our labelling methods (i.e., 9 red 3 SNR bins times 11 yellow 3 SNR bins times 8 green 3 SNR bins times 6 blue 3 SNR bins), as shown in FIGS. 14A-14D and 15. Other ways of differentiating the colorimetry may result in higher spectral content (cluster analysis, etc). The unit "Peak SNR" represents is the SNR of a brightest pixel in each identified cell (in a given channel) divided by the maximum SNR for that channel.

Although preferred embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

What is claimed is:

1. A method of detecting neural activity, comprising
inducing neurons of a subject to express at least one of two or more polypeptides each comprising an amino acid sequence represented by SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or a sequence having at least 90% sequence homology with any one of the foregoing, wherein inducing comprises stimulating interneuronally different relative levels of expression of the two or more polypeptides;
applying coelenterazine to the subject;
applying a first stimulation of neural activity to the subject;
detecting a first spatiotemporal and spectral pattern of electromagnetic radiation emitted by neurons of the subject in response to the first stimulation;
recording the first spatiotemporal and spectral pattern of electromagnetic radiation in a computer memory;
applying a second stimulation of neural activity to the subject;
detecting a second spatiotemporal and spectral pattern of electromagnetic radiation emitted by neurons of the subject in response to the second stimulation;
analyzing, using one or more microprocessors, the second spatiotemporal and spectral pattern of electromagnetic radiation to the first spatiotemporal and spectral pattern of electromagnetic radiation, wherein the one or more microprocessors are configured to determine differences and similarities between the second spatiotemporal and spectral pattern of electromagnetic radiation and the first spatiotemporal and spectral pattern of electromagnetic radiation, differences indicate differences in neural activity caused by the first stimulation and the second stimulation, and similarities indicate similarities in neural activity caused by the first stimulation and the second stimulation.

2. The method of claim 1, wherein the two or more polypeptides each comprise a sequence having at least 95% sequence homology with SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

3. The method of claim 1, wherein the two or more polypeptides each comprise a sequence having at least 90% sequence homology with SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

4. The method of claim 1, wherein the two or more polypeptides comprise two or more of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

5. The method of claim 1 wherein inducing comprises transfecting neurons with at least one of two or more polynucleotides wherein each of the two or more polynucleotides encodes for one of the polypeptides.

6. The method of claim 5 wherein a polynucleotide comprises a viral vector.

7. The method of claim 5 wherein a polynucleotide comprises a plasmid.

8. The method of claim 1 wherein the first stimulation, the second stimulation, or both, are sensory stimulation.

9. The method of claim 1 wherein the first stimulation, the second stimulation, or both, are visual stimulation, olfactory stimulation, auditory stimulation, gustatory stimulation, tactile stimulation, proprioceptive stimulation, pain stimulation, or electrical stimulation.

10. The method of claim 1 wherein the first stimulation, the second stimulation, or both, are pharmacological stimulation.

11. The method of claim 1 wherein the first stimulation, the second stimulation, or both, are electrical neural stimulation.

12. The method of claim 1 wherein the subject is a mouse, a rat, a human, or a non-human primate.

13. A method of detecting neural activity, comprising inducing neurons of a subject to express at least one of two or more polypeptides each comprising a fluorescent protein connected to an aequorin by a linker, wherein the amino acid sequence of each of the fluorescent proteins is independently represented by amino acids 1 through 239 of SEQ ID NO:13, amino acids 1 through 239 of SEQ ID NO:14, amino acids 1 through 237 of SEQ ID NO:15, or amino acids 1 through 237 of SEQ ID NO:16, the amino acid sequence of each of the linkers is independently represented by amino acids 240 through 256 of SEQ ID NO:13, and the amino acid sequence of each of the aequorins is independently represented by amino acids 257 through 448 of SEQ ID NO:13, amino acids 257 through 450 of SEQ ID NO:17, or amino acids 257 through 450 of SEQ ID NO:21; and applying coelenterazine to the subject;

applying a first stimulation of neural activity to the subject;

detecting a first spatiotemporal and spectral pattern of electromagnetic radiation emitted by neurons of the subject in response to the first stimulation;

recording the first spatiotemporal and spectral pattern of electromagnetic radiation in a computer memory;

applying a second stimulation of neural activity to the subject;

detecting a second spatiotemporal and spectral pattern of electromagnetic radiation emitted by neurons of the subject in response to the second stimulation;

analyzing, using one or more microprocessors, the second spatiotemporal and spectral pattern of electromagnetic radiation to the first spatiotemporal and spectral pattern of electromagnetic radiation, wherein the one or more microprocessors are configured to determine differences and similarities between the second spatiotemporal and spectral pattern of electromagnetic radiation and the first spatiotemporal and spectral pattern of electromagnetic radiation, differences indicate differences in neural activity caused by the first stimulation and the second stimulation, and similarities indicate similarities in neural activity caused by the first stimulation and the second stimulation.

14. The method of claim 13, wherein inducing comprises transfecting neurons with at least one of two or more polynucleotides wherein each of the two or more polynucleotides encodes for one of the polypeptides.

15. The method of claim 14 wherein a polynucleotide comprises a viral vector.

16. The method of claim 14 wherein a polynucleotide comprises a plasmid.

17. The method of claim 13 wherein the first stimulation, the second stimulation, or both, are sensory stimulation.

18. The method of claim 13 wherein the first stimulation, the second stimulation, or both, are visual stimulation, olfactory stimulation, auditory stimulation, gustatory stimulation, tactile stimulation, proprioceptive stimulation, pain stimulation, or electrical stimulation.

19. The method of claim 13 wherein the first stimulation, the second stimulation, or both, are pharmacological stimulation.

20. The method of claim 13 wherein the first stimulation, the second stimulation, or both, are electrical neural stimulation.

21. The method of claim 13 wherein the subject is a mouse, a rat, a human, or a non-human primate.

22. The method of claim 1, further comprising recording the second spatiotemporal and spectral pattern of electromagnetic radiation in a computer memory, wherein analyzing comprises comparing the first spatiotemporal and spectral pattern of electromagnetic radiation stored in the computer memory to the second spatiotemporal and spectral pattern of electromagnetic radiation stored in the computer memory.

23. The method of claim 13, further comprising recording the second spatiotemporal and spectral pattern of electromagnetic radiation in a computer memory, wherein analyzing comprises comparing the first spatiotemporal and spectral pattern of electromagnetic radiation stored in the computer memory to the second spatiotemporal and spectral pattern of electromagnetic radiation stored in the computer memory.

* * * * *

SEQUENCE LISTING

<160> NUMBER OF SEQ ID NOS: 28

<210> SEQ ID NO 1

```
<211> LENGTH: 1347
<212> TYPE: DNA
<213> ORGANISM: Artificial Sequence
<220> FEATURE:
<223> OTHER INFORMATION: synthetic construct

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcgccc gctacccga ccacatgaag      240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaacgccat cagcgacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaagggt     720
accgagctgt acaagtccgg cgggagcgga tccggcggcc agtccggact cagatctgtc     780
aaacttacat cagacttcga acccaagat ggattggac gacacaagca tatgttcaat       840
ttccttgatg tcaaccacaa tggaaaaatc tctcttgacg agatggtcta caaggcatct     900
gatattgtca tcaataacct tggagcaaca cctgagcaag ccaaacgaca caagatgct      960
gtggaagcct cttcggagg agctggaatg aaatatggtg tggaaactga ttggcctgca     1020
tatattgaag gatggaaaaa attggctact gatgaattgg agaaatacgc caaaaacgaa    1080
ccaaccctca tccgcatctg gggtgatgct ttgtttgata tcgttgacaa agatcaaaat    1140
ggagctatta cactggatga atggaaagca tacaccaaag ctgctggtat catccaatca    1200
tcagaagatt gcgaggaaac attcagagtg tgcgatattg atgaaagtgg acaactcgat    1260
gttgatgaga tgacaagaca gcatctggga ttttggtaca ccatggatcc tgcttgcgaa    1320
aagctctacg gtgagctgt cccctaa                                         1347

<210> SEQ ID NO 2
<211> LENGTH: 1347
<212> TYPE: DNA
<213> ORGANISM: Artificial Sequence
<220> FEATURE:
<223> OTHER INFORMATION: synthetic construct

<400> SEQUENCE: 2
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctacccga ccacatgaag      240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
```

| | |
|---|---|
| ggcatcaagg ccaacttcaa gatccgccac aacatcgagg acggcagcgt gcagctcgcc | 540 |
| gaccactacc agcagaacac ccccatcggc gacggcccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagggt | 720 |
| accgagctgt acaagtccgg cgggagcgga tccggcggcc agtccggact cagatctgtc | 780 |
| aaacttacat cagacttcga caacccaaga tggattggac gacacaagca tatgttcaat | 840 |
| ttccttgatg tcaaccacaa tggaaaaatc tctcttgacg agatggtcta caaggcatct | 900 |
| gatattgtca tcaataacct ggagcaaca cctgagcaag ccaaacgaca caagatgct | 960 |
| gtggaagcct tcttcggagg agctggaatg aaatatggtg tggaaactga ttggcctgca | 1020 |
| tatattgaag gatggaaaaa attggctact gatgaattgg agaaatacgc caaaaacgaa | 1080 |
| ccaaccctca tccgcatctg gggtgatgct ttgtttgata tcgttgacaa agatcaaaat | 1140 |
| ggagctatta cactgatga atggaaagca taccaaaag ctgctggtat catccaatca | 1200 |
| tcagaagatt gcgaggaaac attcagagtg tgcgatattg atgaaagtgg acaactcgat | 1260 |
| gttgatgaga tgacaagaca gcatctggga ttttggtaca ccatggatcc tgcttgcgaa | 1320 |
| aagctctacg gtggagctgt cccctaa | 1347 |

<210> SEQ ID NO 3
<211> LENGTH: 1341
<212> TYPE: DNA
<213> ORGANISM: Artificial Sequence
<220> FEATURE:
<223> OTHER INFORMATION: synthetic construct

<400> SEQUENCE: 3

| | |
|---|---|
| atggtgtcta agggcgaaga gctgattaag gagaacatgc acatgaagct gtacatggag | 60 |
| ggcaccgtgg acaaccatca cttcaagtgc acatccgagg gcgaaggcaa gccctacgag | 120 |
| ggcacccaga ccatgagaat caaggtggtc gagggcggcc ctctcccctt cgccttcgac | 180 |
| atcctggcta ctagcttcct ctacggcagc aagaccttca tcaaccacac ccagggcatc | 240 |
| cccgacttct tcaagcagtc cttccctgag ggcttcacat gggagagagt caccacatac | 300 |
| gaagacgggg gcgtgctgac cgctacccag gacaccagcc tccaggacgg ctgcctcatc | 360 |
| tacaacgtca gatcagagg ggtgaacttc acatccaacg ccctgtgat gcagaagaaa | 420 |
| acactcggct gggaggcctt caccgagacg ctgtaccccg ctgacggcgg cctggaaggc | 480 |
| agaaacgaca tggccctgaa gctcgtgggc gggagccatc tgatcgcaaa cgccaagacc | 540 |
| acatatagat ccaagaaacc cgctaagaac ctcaagatgc ctggcgtcta ctatgtggac | 600 |
| tacagactga aagaatcaa ggaggccaac aacgagacct acgtcgagca gcacgaggtg | 660 |
| gcagtggcca gatactgcga cctccctagc aaactggggc acaagcttaa tggtaccgag | 720 |
| ctgtacaagt ccggcgggag cggatccggc ggccagtccg gactcagatc tgtcaaactt | 780 |
| acatcagact tcgacaaccc aagatggatt ggacgacaca gcatatgtt caatttcctt | 840 |
| gatgtcaacc acaatggaaa aatctctctt gacgagatgg tctacaaggc atctgatatt | 900 |
| gtcatcaata accttggagc aacacctgag caagccaaac gacacaaaga tgctgtggaa | 960 |
| gccttcttcg gaggagctgg aatgaaatat ggtgtggaaa ctgattggcc tgcatatatt | 1020 |
| gaaggatgga aaaattggc tactgatgaa ttggagaaat acgccaaaaa cgaaccaacc | 1080 |
| ctcatccgca tctggggtga tgctttgttt gatatcgttg acaaagatca aaatggagct | 1140 |

| | |
|---|---:|
| attacactgg atgaatggaa agcatacacc aaagctgctg gtatcatcca atcatcagaa | 1200 |
| gattgcgagg aaacattcag agtgtgcgat attgatgaaa gtggacaact cgatgttgat | 1260 |
| gagatgacaa gacagcatct gggatttggg tacaccatgg atcctgcttg cgaaaagctc | 1320 |
| tacggtggag ctgtcccctaa | 1341 |

```
<210> SEQ ID NO 4
<211> LENGTH: 1338
<212> TYPE: DNA
<213> ORGANISM: Artificial Sequence
<220> FEATURE:
<223> OTHER INFORMATION: synthetic construct

<400> SEQUENCE: 4
```

| | |
|---|---:|
| atggtgagca agggcgagga gaccacaatg ggcgtaatca gcccgacat gaagatcaag | 60 |
| ctgaagatgg agggcaacgt gaatggccac gccttcgtga tcgagggcga gggcgagggc | 120 |
| aagccctacg acggcaccaa caccatcaac ctggaggtga aggagggagc ccccctgccc | 180 |
| ttctcctacg acattctgac caccgcgttc gcctacggca cagggccttt caccaagtac | 240 |
| cccgacgaca tccccaacta cttcaagcag tccttccccg agggctactc ttgggagcgc | 300 |
| accatgacct tcgaggacaa gggcatcgtg aaggtgaagt ccgacatctc catggaggag | 360 |
| gactccttca tctacgagat acacctcaag ggcgagaact cccccccaa cggccccgtg | 420 |
| atgcagaaga gaccaccgg ctgggacgcc tccaccgaga ggatgtacgt gcgcgacggc | 480 |
| gtgctgaagg gcgacgtcaa gcacaagctg ctgctggagg gcggcggcca ccaccgcgtt | 540 |
| gacttcaaga ccatctacag ggccaagaag gcggtgaagt gccccgacta tcactttgtg | 600 |
| gaccaccgca tcgagatcct gaaccacgac aaggactaca acaaggtgac cgtttacgag | 660 |
| agcgccgtgg cccgcaactc caccgacggc atggacgagc tgtacaaggg taccgagctg | 720 |
| tacaagtccg gcgggagcgg atccggcggc cagtccggac tcagatctgt caaacttaca | 780 |
| tcagacttcg acaacccaag atggattgga cgacacaagc atatgttcaa tttccttgat | 840 |
| gtcaaccaca atggaaaaat ctctcttgac gagatggtct acaaggcatc tgatattgtc | 900 |
| atcaataacc ttggagcaac acctgagcaa gccaaacgac acaaagatgc tgtggaagcc | 960 |
| ttcttcggag gagctggaat gaaatatggt gtggaaactg attggcctgc atatattgaa | 1020 |
| ggatggaaaa aattggctac tgatgaattg gagaaatacg ccaaaaacga accaaccctc | 1080 |
| atccgcatct ggggtgatgc tttgtttgat atcgttgaca agatcaaaa tggagctatt | 1140 |
| acactggatg aatggaaagc atacaccaaa gctgctggta tcatccaatc atcagaagat | 1200 |
| tgcgaggaaa cattcagagt gtgcgatatt gatgaaagtg gacaactcga tgttgatgag | 1260 |
| atgacaagac agcatctggg attttggtac accatggatc ctgcttgcga aaagctctac | 1320 |
| ggtggagctg tcccctaa | 1338 |

```
<210> SEQ ID NO 5
<211> LENGTH: 1353
<212> TYPE: DNA
<213> ORGANISM: Artificial Sequence
<220> FEATURE:
<223> OTHER INFORMATION: synthetic construct

<400> SEQUENCE: 5
```

| | |
|---|---:|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |

```
ctcgtgacca ccctgacctg gggcgtgcag tgcttcagcc gctaccccga ccacatgaag        240
cagcacgact tcttcaagtc cgccatgccc gaaggctacg tccaggagcg caccatcttc        300
ttcaaggacg acggcaacta caagacccgc gccgaggtga agttcgaggg cgacaccctg        360
gtgaaccgca tcgagctgaa gggcatcgac ttcaaggagg acggcaacat cctggggcac        420
aagctggagt acaactacat cagccacaac gtctatatca ccgccgacaa gcagaagaac        480
ggcatcaagg ccaacttcaa gatccgccac aacatcgagg acggcagcgt gcagctcgcc        540
gaccactacc agcagaacac ccccatcggc gacggccccg tgctgctgcc cgacaaccac        600
tacctgagca cccagtccgc cctgagcaaa gaccccaacg agaagcgcga tcacatggtc        660
ctgctggagt tcgtgaccgc cgccgggatc actctcggca tggacgagct gtacaagggt        720
accgagctgt acaagtccgg cgggagcgga tccggcggcc agtccggatc ttcaaaatac        780
gcagttaaac tcaagactga ctttgataat ccacgatgga tcaaaagaca caagcacatg        840
tttgatttcc tcgacatcaa tggaaatgga aaaatcaccc tcgatgaaat tgtgtccaag        900
gcatctgatg acatatgtgc caagctcgaa gccacaccag aacaaacaaa acgccatcaa        960
gtttgtgttg aagcttttctt tagaggatgt ggaatggaat atggtaaaga aattgccttc       1020
ccacaattcc tcgatggatg gaaacaattg gcgacttcag aactcaagaa atgggcaaga       1080
aacgaaccta ctctcattcg tgaatgggga gatgctgtct ttgatatttt cgacaaagat       1140
ggaagtggta caatcacttt ggacgaatgg aaagcttatg gaaaaatctc tggtatctct       1200
ccatcacaag aagattgtga agcgacattt cgacattgcg atttggacaa cagtggtgac       1260
cttgatgttg acgagatgac aagacaacat cttggattct ggtacacttt ggacccagaa       1320
gctgatggtc tctatggcaa cggagttccc taa                                    1353
```

<210> SEQ ID NO 6
<211> LENGTH: 1353
<212> TYPE: DNA
<213> ORGANISM: Artificial Sequence
<220> FEATURE:
<223> OTHER INFORMATION: synthetic construct

<400> SEQUENCE: 6

```
atggtgagca agggcgagga gctgttcacc ggggtggtgc ccatcctggt cgagctggac         60
ggcgacgtaa acggccacaa gttcagcgtg tccggcgagg gcgagggcga tgccacctac        120
ggcaagctga ccctgaagtt catctgcacc accggcaagc tgcccgtgcc ctggcccacc        180
ctcgtgacca ccctgacctg gggcgtgcag tgcttcgccc gctaccccga ccacatgaag        240
cagcacgact tcttcaagtc cgccatgccc gaaggctacg tccaggagcg caccatcttc        300
ttcaaggacg acggcaacta caagacccgc gccgaggtga agttcgaggg cgacaccctg        360
gtgaaccgca tcgagctgaa gggcatcgac ttcaaggagg acggcaacat cctggggcac        420
aagctggagt acaacgccat cagcgacaac gtctatatca ccgccgacaa gcagaagaac        480
ggcatcaagg ccaacttcaa gatccgccac aacatcgagg acggcagcgt gcagctcgcc        540
gaccactacc agcagaacac ccccatcggc gacggccccg tgctgctgcc cgacaaccac        600
tacctgagca cccagtccaa gctgagcaaa gaccccaacg agaagcgcga tcacatggtc        660
ctgctggagt tcgtgaccgc cgccgggatc actctcggca tggacgagct gtacaagggt        720
accgagctgt acaagtccgg cgggagcgga tccggcggcc agtccggatc ttcaaaatac        780
gcagttaaac tcaagactga ctttgataat ccacgatgga tcaaaagaca caagcacatg        840
```

| | |
|---|---|
| tttgatttcc tcgacatcaa tggaaatgga aaaatcaccc tcgatgaaat tgtgtccaag | 900 |
| gcatctgatg acatatgtgc caagctcgaa gccacaccag aacaaacaaa acgccatcaa | 960 |
| gtttgtgttg aagctttctt tagaggatgt ggaatggaat atggtaaaga aattgccttc | 1020 |
| ccacaattcc tcgatggatg gaaacaattg gcgacttcag aactcaagaa atgggcaaga | 1080 |
| aacgaaccta ctctcattcg tgaatgggga gatgctgtct ttgatatttt cgacaaagat | 1140 |
| ggaagtggta caatcacttt ggacgaatgg aaagcttatg gaaaaatctc tggtatctct | 1200 |
| ccatcacaag aagattgtga agcgacattt cgacattgcg atttggacaa cagtggtgac | 1260 |
| cttgatgttg acgagatgac aagacaacat cttggattct ggtacacttt ggacccagaa | 1320 |
| gctgatggtc tctatggcaa cggagttccc taa | 1353 |

<210> SEQ ID NO 7
<211> LENGTH: 1347
<212> TYPE: DNA
<213> ORGANISM: Artificial Sequence
<220> FEATURE:
<223> OTHER INFORMATION: synthetic construct

<400> SEQUENCE: 7

| | |
|---|---|
| atggtgtcta agggcgaaga gctgattaag gagaacatgc acatgaagct gtacatggag | 60 |
| ggcaccgtgg acaaccatca cttcaagtgc acatccgagg gcgaaggcaa gccctacgag | 120 |
| ggcacccaga ccatgagaat caaggtggtc gagggcggcc ctctcccctt cgccttcgac | 180 |
| atcctggcta ctagcttcct ctacggcagc aagaccttca tcaaccacac ccagggcatc | 240 |
| cccgacttct tcaagcagtc cttccctgag ggcttcacat gggagagagt caccacatac | 300 |
| gaagacgggg gcgtgctgac cgctacccag acaccagcc tccaggacgg ctgcctcatc | 360 |
| tacaacgtca agatcagagg ggtgaacttc acatccaacg ccctgtgat gcagaagaaa | 420 |
| acactcggct gggaggcctt caccgagacg ctgtaccccg ctgacggcgg cctggaaggc | 480 |
| agaaacgaca tggcccctgaa gctcgtgggc gggagccatc tgatcgcaaa cgccaagacc | 540 |
| acatatagat ccaagaaacc cgctaagaac ctcaagatgc ctggcgtcta ctatgtggac | 600 |
| tacagactgg aaagaatcaa ggaggccaac aacgagacct acgtcgagca gcacgaggtg | 660 |
| gcagtggcca gatactgcga cctccctagc aaactggggc acaagcttaa tggtaccgag | 720 |
| ctgtacaagt ccggcgggag cggatccggc ggccagtccg gatcttcaaa atacgcagtt | 780 |
| aaactcaaga ctgactttga taatccacga tggatcaaaa gacacaagca catgtttgat | 840 |
| ttcctcgaca tcaatggaaa tggaaaaatc accctcgatg aaattgtgtc caaggcatct | 900 |
| gatgacatat gtgccaagct cgaagccaca ccagaacaaa caaaacgcca tcaagtttgt | 960 |
| gttgaagctt tctttagagg atgtggaatg gaatatggta agaaattgc cttcccacaa | 1020 |
| ttcctcgatg gatggaaaca attggcgact tcagaactca gaaatgggc aagaaacgaa | 1080 |
| cctactctca ttcgtgaatg gggagatgct gtctttgata ttttcgacaa agatggaagt | 1140 |
| ggtacaatca ctttggacga atggaaagct tatggaaaaa tctctggtat ctctccatca | 1200 |
| caagaagatt gtgaagcgac atttcgacat tgcgatttgg acaacagtgg tgaccttgat | 1260 |
| gttgacgaga tgacaagaca acatcttgga ttctggtaca ctttggaccc agaagctgat | 1320 |
| ggtctctatg gcaacggagt tccctaa | 1347 |

<210> SEQ ID NO 8
<211> LENGTH: 1344
<212> TYPE: DNA
<213> ORGANISM: Artificial Sequence

```
<220> FEATURE:
<223> OTHER INFORMATION: synthetic construct

<400> SEQUENCE: 8
atggtgagca agggcgagga gaccacaatg ggcgtaatca agcccgacat gaagatcaag      60
ctgaagatgg agggcaacgt gaatggccac gccttcgtga tcgagggcga gggcgagggc     120
aagccctacg acggcaccaa caccatcaac ctggaggtga aggagggagc cccctgccc     180
ttctcctacg acattctgac caccgcgttc gcctacggca cagggcctt caccaagtac     240
cccgacgaca tccccaacta cttcaagcag tccttccccg agggctactc ttgggagcgc     300
accatgacct tcgaggacaa gggcatcgtg aaggtgaagt ccgacatctc catggaggag     360
gactccttca tctacgagat acacctcaag ggcgagaact tccccccaa cggccccgtg     420
atgcagaaga gaccaccgg ctgggacgcc tccaccgaga ggatgtacgt gcgcgacggc     480
gtgctgaagg gcgacgtcaa gcacaagctg ctgctggagg cggcggcca ccaccgcgtt     540
gacttcaaga ccatctacag ggccaagaag gcggtgaagc tgcccgacta tcactttgtg     600
gaccaccgca tcgagatcct gaaccacgac aaggactaca caaggtgac cgtttacgag     660
agcgccgtgg cccgcaactc caccgacggc atggacgagc tgtacaaggg taccgagctg     720
tacaagtccg gcgggagcgg atccggcggc cagtccggat cttcaaaata cgcagttaaa     780
ctcaagactg actttgataa tccacgatgg atcaaaagac acaagcacat gtttgatttc     840
ctcgacatca atggaaatgg aaaaatcacc ctcgatgaaa ttgtgtccaa ggcatctgat     900
gacatatgtg ccaagctcga agccacacca gaacaaacaa aacgccatca agtttgtgtt     960
gaagctttct ttagaggatg tggaatggaa tatggtaaag aaattgcctt cccacaattc    1020
ctcgatggat ggaaacaatt ggcgacttca gaactcaaga aatgggcaag aaacgaacct    1080
actctcattc gtgaatgggg agatgctgtc tttgatatt tcgacaaaga tggaagtggt    1140
acaatcactt tggacgaatg gaaagcttat ggaaaaatct ctggtatctc tccatcacaa    1200
gaagattgtg aagcgacatt tcgacattgc gatttggaca cagtggtga ccttgatgtt    1260
gacgagatga caagacaaca tcttggattc tggtacactt tggacccaga agctgatggt    1320
ctctatggca acggagttcc ctaa                                          1344

<210> SEQ ID NO 9
<211> LENGTH: 1353
<212> TYPE: DNA
<213> ORGANISM: Artificial Sequence
<220> FEATURE:
<223> OTHER INFORMATION: synthetic construct

<400> SEQUENCE: 9
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca cccctgacctg gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagggt    720
accgagctgt acaagtccgg cgggagcgga tccggcggcc agtccggaac cagcaaatac    780
gccgtcaaac ttgagccaga cttttgagaac ccaaaatggg ttggtcgaca caagcatatg    840
ttcaaattcc ttgatgtcaa tcaaaatgga aagatctctc ttgacgagat ggtctacaag    900
gcgtccgaca ttgtcatcaa caatcttggg gcgacacccg aacaagctaa acgacacaag    960
gacgccgtag aggctttctt cggaggcgcc ggaatgaaat acggcgtgga aactgaatgg   1020
cctgaataca tcgaaggatg gaagaatttg gcgagaacgg aattagacag atttgcaaag   1080
aatcaaataa cgctcattcg cttgtggggc gatgcgttgt ttgacatcat tgacaaagat   1140
caaaatggtg ctatcacctt ggacgaatgg aagaaataca cactgtcagc tggcatcatt   1200
cagtcagcag aagattgcga gataacgttc aaggtatgtg atttggacga cagtggaaga   1260
cttgatgccg acgaaatgac acgacaacac atcggatttt ggtacaccat ggatccggcg   1320
tgcgaaaagc tctacggagg agctgtcccc taa                                1353
```

<210> SEQ ID NO 10  
<211> LENGTH: 1353  
<212> TYPE: DNA  
<213> ORGANISM: Artificial Sequence  
<220> FEATURE:  
<223> OTHER INFORMATION: synthetic sequence

<400> SEQUENCE: 10

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca cccctgacctg gggcgtgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaacgccat cagcgacaac gtctatatca ccgccgacaa gcagaagaac    480
ggcatcaagg ccaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccaa gctgagcaaa gaccccaacg agaagcgcga tcacatggtc    660
ctgctggagt tcgtgaccgc cgccgggatc actctcggca tggacgagct gtacaagggt    720
accgagctgt acaagtccgg cgggagcgga tccggcggcc agtccggaac cagcaaatac    780
gccgtcaaac ttgagccaga cttttgagaac ccaaaatggg ttggtcgaca caagcatatg    840
ttcaaattcc ttgatgtcaa tcaaaatgga aagatctctc ttgacgagat ggtctacaag    900
gcgtccgaca ttgtcatcaa caatcttggg gcgacacccg aacaagctaa acgacacaag    960
gacgccgtag aggctttctt cggaggcgcc ggaatgaaat acggcgtgga aactgaatgg   1020
cctgaataca tcgaaggatg gaagaatttg gcgagaacgg aattagacag atttgcaaag   1080
aatcaaataa cgctcattcg cttgtggggc gatgcgttgt ttgacatcat tgacaaagat   1140
caaaatggtg ctatcacctt ggacgaatgg aagaaataca cactgtcagc tggcatcatt   1200
cagtcagcag aagattgcga gataacgttc aaggtatgtg atttggacga cagtggaaga   1260
```

```
cttgatgccg acgaaatgac acgacaacac atcggatttt ggtacaccat ggatccggcg    1320
tgcgaaaagc tctacggagg agctgtcccc taa                                1353

<210> SEQ ID NO 11
<211> LENGTH: 1347
<212> TYPE: DNA
<213> ORGANISM: Artificial Sequence
<220> FEATURE:
<223> OTHER INFORMATION: synthetic sequence

<400> SEQUENCE: 11
atggtgtcta agggcgaaga gctgattaag gagaacatgc acatgaagct gtacatggag      60
ggcaccgtgg acaaccatca cttcaagtgc acatccgagg gcgaaggcaa gccctacgag     120
ggcacccaga ccatgagaat caaggtggtc gagggcggcc ctctcccctt cgccttcgac     180
atcctggcta ctagcttcct ctacggcagc aagaccttca tcaaccacac ccagggcatc     240
cccgacttct tcaagcagtc cttccctgag ggcttcacat gggagagagt caccacatac     300
gaagacgggg gcgtgctgac cgctacccag gacaccagcc tccaggacgg ctgcctcatc     360
tacaacgtca agatcagagg ggtgaacttc acatccaacg ccctgtgat gcagaagaaa      420 acactcggct gggaggcctt caccgagacg ctgtaccccg ctgacggcgg cctggaaggc     480
agaaacgaca tggccctgaa gctcgtgggc gggagccatc tgatcgcaaa cgccaagacc     540
acatatagat ccaagaaacc cgctaagaac ctcaagatgc ctggcgtcta ctatgtggac     600
tacagactgg aaagaatcaa ggaggccaac aacgagacct acgtcgagca gcacgaggtg     660
gcagtggcca gatactgcga cctccctagc aaactggggc acaagcttaa tggtaccgag     720
ctgtacaagt ccggcgggag cggatccggc ggccagtccg gaaccagcaa atacgccgtc     780
aaacttgagc cagactttga gaacccaaaa tgggttggtc gacacaagca tatgttcaaa     840
ttccttgatg tcaatcaaaa tggaaagatc tctcttgacg agatggtcta caaggcgtcc     900
gacattgtca tcaacaatct tggggcgaca cccgaacaag ctaaacgaca caaggacgcc     960
gtagaggctt tcttcggagg cgccggaatg aaatacggcg tggaaactga atggcctgaa    1020
tacatcgaag gatggaagaa tttggcgaga acggaattag acagatttgc aaagaatcaa    1080
ataacgctca ttcgcttgtg gggcgatgcg ttgtttgaca tcattgacaa agatcaaaat    1140
ggtgctatca ccttggacga atggaagaaa tacacactgt cagctggcat cattcagtca    1200
gcagaagatt gcgagataac gttcaaggta tgtgatttgg acgacagtgg aagacttgat    1260
gccgacgaaa tgcacacgac acacatcgga ttttggtaca ccatggatcc ggcgtgcgaa    1320
aagctctacg gaggagctgt cccctaa                                       1347

<210> SEQ ID NO 12
<211> LENGTH: 1344
<212> TYPE: DNA
<213> ORGANISM: Artificial Sequence
<220> FEATURE:
<223> OTHER INFORMATION: synthetic construct

<400> SEQUENCE: 12
atggtgagca agggcgagga gaccacaatg ggcgtaatca gcccgacat gaagatcaag       60 ctgaagatgg agggcaacgt gaatggccac gccttcgtga tcgagggcga gggcgagggc    120
aagccctacg acggcaccaa caccatcaac ctggaggtga aggagggagc cccctgccc     180 ttctcctacg acattctgac caccgcgttc gcctacggca cagggccttt caccaagtac    240
```

```
cccgacgaca tccccaacta cttcaagcag tccttcccg agggctactc ttgggagcgc      300
accatgacct tcgaggacaa gggcatcgtg aaggtgaagt ccgacatctc catggaggag     360
gactccttca tctacgagat acacctcaag ggcgagaact tccccccaa cggccccgtg     420
atgcagaaga agaccaccgg ctgggacgcc tccaccgaga ggatgtacgt gcgcgacggc    480
gtgctgaagg gcgacgtcaa gcacaagctg ctgctggagg gcggcggcca ccaccgcgtt    540
gacttcaaga ccatctacag ggccaagaag gcggtgaagc tgcccgacta tcactttgtg    600
gaccaccgca tcgagatcct gaaccacgac aaggactaca caaggtgac cgtttacgag      660
agcgccgtgg cccgcaactc caccgacggc atggacgagc tgtacaaggg taccgagctg    720
tacaagtccg gcgggagcgg atccggcggc cagtccggaa ccagcaaata cgccgtcaaa    780
cttgagccag actttgagaa cccaaaatgg gttggtcgac acaagcatat gttcaaattc    840
cttgatgtca atcaaaatgg aaagatctct cttgacgaga tggtctacaa ggcgtccgac    900
attgtcatca acaatcttgg ggcgacaccc gaacaagcta aacgacacaa ggacgccgta    960
gaggctttct tcggaggcgc cggaatgaaa tacggcgtgg aaactgaatg gcctgaatac   1020
atcgaaggat ggaagaattt ggcgagaacg gaattagaca gatttgcaaa gaatcaaata   1080
acgctcattc gcttgtgggg cgatgcgttg tttgacatca ttgacaaaga tcaaaatggt   1140
gctatcacct tggacgaatg gaagaaatac acactgtcag ctggcatcat tcagtcagca   1200
gaagattgcg agataacgtt caaggtatgt gatttggacg acagtggaag acttgatgcc   1260
gacgaaatga cacgacaaca catcggattt tggtacacca tggatccggc gtgcgaaaag   1320
ctctacggag gagctgtccc ctaa                                           1344
```

<210> SEQ ID NO 13
<211> LENGTH: 448
<212> TYPE: PRT
<213> ORGANISM: Artificial Sequence
<220> FEATURE:
<223> OTHER INFORMATION: synthetic construct

<400> SEQUENCE: 13

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Ala Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser

```
                165                 170                 175
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Thr Glu Leu Tyr Lys Ser Gly Gly Ser Gly Gly Gln Ser Gly
                245                 250                 255

Leu Arg Ser Val Lys Leu Thr Ser Asp Phe Asp Asn Pro Arg Trp Ile
            260                 265                 270

Gly Arg His Lys His Met Phe Asn Phe Leu Asp Val Asn His Asn Gly
        275                 280                 285

Lys Ile Ser Leu Asp Glu Met Val Tyr Lys Ala Ser Asp Ile Val Ile
    290                 295                 300

Asn Asn Leu Gly Ala Thr Pro Glu Gln Ala Lys Arg His Lys Asp Ala
305                 310                 315                 320

Val Glu Ala Phe Phe Gly Gly Ala Gly Met Lys Tyr Gly Val Glu Thr
                325                 330                 335

Asp Trp Pro Ala Tyr Ile Glu Gly Trp Lys Lys Leu Ala Thr Asp Glu
            340                 345                 350

Leu Glu Lys Tyr Ala Lys Asn Glu Pro Thr Leu Ile Arg Ile Trp Gly
        355                 360                 365

Asp Ala Leu Phe Asp Ile Val Asp Lys Asp Gln Asn Gly Ala Ile Thr
    370                 375                 380

Leu Asp Glu Trp Lys Ala Tyr Thr Lys Ala Ala Gly Ile Ile Gln Ser
385                 390                 395                 400

Ser Glu Asp Cys Glu Glu Thr Phe Arg Val Cys Asp Ile Asp Glu Ser
                405                 410                 415

Gly Gln Leu Asp Val Asp Glu Met Thr Arg Gln His Leu Gly Phe Trp
            420                 425                 430

Tyr Thr Met Asp Pro Ala Cys Glu Lys Leu Tyr Gly Gly Ala Val Pro
        435                 440                 445

<210> SEQ ID NO 14
<211> LENGTH: 448
<212> TYPE: PRT
<213> ORGANISM: Artificial Sequence
<220> FEATURE:
<223> OTHER INFORMATION: synthetic construct

<400> SEQUENCE: 14

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
```

```
                    85                  90                  95
Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys Gly
225                 230                 235                 240

Thr Glu Leu Tyr Lys Ser Gly Gly Ser Gly Gly Gln Ser Gly
                245                 250                 255

Leu Arg Ser Val Lys Leu Thr Ser Asp Phe Asp Asn Pro Arg Trp Ile
            260                 265                 270

Gly Arg His Lys His Met Phe Asn Phe Leu Asp Val Asn His Asn Gly
                275                 280                 285

Lys Ile Ser Leu Asp Glu Met Val Tyr Lys Ala Ser Asp Ile Val Ile
            290                 295                 300

Asn Asn Leu Gly Ala Thr Pro Glu Gln Ala Lys Arg His Lys Asp Ala
305                 310                 315                 320

Val Glu Ala Phe Phe Gly Gly Ala Gly Met Lys Tyr Gly Val Glu Thr
                325                 330                 335

Asp Trp Pro Ala Tyr Ile Glu Gly Trp Lys Lys Leu Ala Thr Asp Glu
            340                 345                 350

Leu Glu Lys Tyr Ala Lys Asn Glu Pro Thr Leu Ile Arg Ile Trp Gly
            355                 360                 365

Asp Ala Leu Phe Asp Ile Val Asp Lys Asp Gln Asn Gly Ala Ile Thr
            370                 375                 380

Leu Asp Glu Trp Lys Ala Tyr Thr Lys Ala Ala Gly Ile Ile Gln Ser
385                 390                 395                 400

Ser Glu Asp Cys Glu Glu Thr Phe Arg Val Cys Asp Ile Asp Glu Ser
                405                 410                 415

Gly Gln Leu Asp Val Asp Glu Met Thr Arg Gln His Leu Gly Phe Trp
            420                 425                 430

Tyr Thr Met Asp Pro Ala Cys Glu Lys Leu Tyr Gly Gly Ala Val Pro
            435                 440                 445
```

<210> SEQ ID NO 15
<211> LENGTH: 446
<212> TYPE: PRT
<213> ORGANISM: Artificial Sequence
<220> FEATURE:
<223> OTHER INFORMATION: synthetic construct

<400> SEQUENCE: 15

Met Val Ser Lys Gly Glu Glu Leu Ile Lys Glu Asn Met His Met Lys

-continued

```
1               5                   10                  15
Leu Tyr Met Glu Gly Thr Val Asp Asn His His Phe Lys Cys Thr Ser
            20                  25                  30
Glu Gly Glu Gly Lys Pro Tyr Glu Gly Thr Gln Thr Met Arg Ile Lys
            35                  40                  45
Val Val Glu Gly Gly Pro Leu Pro Phe Ala Phe Asp Ile Leu Ala Thr
50                  55                  60
Ser Phe Leu Tyr Gly Ser Lys Thr Phe Ile Asn His Thr Gln Gly Ile
65                  70                  75                  80
Pro Asp Phe Phe Lys Gln Ser Phe Pro Glu Gly Phe Thr Trp Glu Arg
                85                  90                  95
Val Thr Thr Tyr Glu Asp Gly Gly Val Leu Thr Ala Thr Gln Asp Thr
                100                 105                 110
Ser Leu Gln Asp Gly Cys Leu Ile Tyr Asn Val Lys Ile Arg Gly Val
                115                 120                 125
Asn Phe Thr Ser Asn Gly Pro Val Met Gln Lys Lys Thr Leu Gly Trp
            130                 135                 140
Glu Ala Phe Thr Glu Thr Leu Tyr Pro Ala Asp Gly Gly Leu Glu Gly
145                 150                 155                 160
Arg Asn Asp Met Ala Leu Lys Leu Val Gly Gly Ser His Leu Ile Ala
                165                 170                 175
Asn Ala Lys Thr Thr Tyr Arg Ser Lys Lys Pro Ala Lys Asn Leu Lys
            180                 185                 190
Met Pro Gly Val Tyr Tyr Val Asp Tyr Arg Leu Glu Arg Ile Lys Glu
            195                 200                 205
Ala Asn Asn Glu Thr Tyr Val Glu Gln His Glu Val Ala Val Ala Arg
210                 215                 220
Tyr Cys Asp Leu Pro Ser Lys Leu Gly His Lys Leu Asn Gly Thr Glu
225                 230                 235                 240
Leu Tyr Lys Ser Gly Gly Ser Gly Ser Gly Gln Ser Gly Leu Arg
                245                 250                 255
Ser Val Lys Leu Thr Ser Asp Phe Asp Asn Pro Arg Trp Ile Gly Arg
            260                 265                 270
His Lys His Met Phe Asn Phe Leu Asp Val Asn His Asn Gly Lys Ile
        275                 280                 285
Ser Leu Asp Glu Met Val Tyr Lys Ala Ser Asp Ile Val Ile Asn Asn
        290                 295                 300
Leu Gly Ala Thr Pro Glu Gln Ala Lys Arg His Lys Asp Ala Val Glu
305                 310                 315                 320
Ala Phe Phe Gly Gly Ala Gly Met Lys Tyr Gly Val Glu Thr Asp Trp
                325                 330                 335
Pro Ala Tyr Ile Glu Gly Trp Lys Lys Leu Ala Thr Asp Glu Leu Glu
            340                 345                 350
Lys Tyr Ala Lys Asn Glu Pro Thr Leu Ile Arg Ile Trp Gly Asp Ala
            355                 360                 365
Leu Phe Asp Ile Val Asp Lys Asp Gln Asn Gly Ala Ile Thr Leu Asp
            370                 375                 380
Glu Trp Lys Ala Tyr Thr Lys Ala Ala Gly Ile Ile Gln Ser Ser Glu
385                 390                 395                 400
Asp Cys Glu Glu Thr Phe Arg Val Cys Asp Ile Asp Glu Ser Gly Gln
                405                 410                 415
Leu Asp Val Asp Glu Met Thr Arg Gln His Leu Gly Phe Trp Tyr Thr
            420                 425                 430
```

```
Met Asp Pro Ala Cys Glu Lys Leu Tyr Gly Gly Ala Val Pro
        435                 440                 445

<210> SEQ ID NO 16
<211> LENGTH: 446
<212> TYPE: PRT
<213> ORGANISM: Artificial Sequence
<220> FEATURE:
<223> OTHER INFORMATION: synthetic construct

<400> SEQUENCE: 16

Met Val Ser Lys Gly Glu Glu Leu Ile Lys Glu Asn Met His Met Lys
1               5                   10                  15

Leu Tyr Met Glu Gly Thr Val Asp Asn His Phe Lys Cys Thr Ser
            20                  25                  30      Ser

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Leu Tyr Gly Ser Lys Thr Phe Ile Asn His Thr Gln Gly Ile
65              70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Thr Ser Asn Gly Pro Val Met Gln Lys Lys Thr Leu Gly Trp
    130                 135                 140

Glu Ala Phe Thr Glu Thr Leu Tyr Pro Ala Asp Gly Gly Leu Glu Gly
145                 150                 155                 160

Arg Asn Asp Met Ala Leu Lys Leu Val Gly Gly Ser His Leu Ile Ala
                165                 170                 175

Asn Ala Lys Thr Thr Tyr Arg Ser Lys Lys Pro Ala Lys Asn Leu Lys
            180                 185                 190

Met Pro Gly Val Tyr Tyr Val Asp Tyr Arg Leu Glu Arg Ile Lys Glu
        195                 200                 205

Ala Asn Asn Glu Thr Tyr Val Glu Gln His Glu Val Ala Val Ala Arg
    210                 215                 220

Tyr Cys Asp Leu Pro Ser Lys Leu Gly His Lys Leu Asn Gly Thr Glu
225                 230                 235                 240

Leu Tyr Lys Ser Gly Gly Ser Gly Gly Gln Ser Gly Leu Arg
                245                 250                 255

Ser Val Lys Leu Thr Ser Asp Phe Asp Asn Pro Arg Trp Ile Gly Arg
            260                 265                 270

His Lys His Met Phe Asn Phe Leu Asp Val Asn His Asn Gly Lys Ile
        275                 280                 285

Ser Leu Asp Glu Met Val Tyr Lys Ala Ser Asp Ile Val Ile Asn Asn
    290                 295                 300

Leu Gly Ala Thr Pro Glu Gln Ala Lys Arg His Lys Asp Ala Val Glu
305                 310                 315                 320

Ala Phe Phe Gly Gly Ala Gly Met Lys Tyr Gly Val Glu Thr Asp Trp
                325                 330                 335

Pro Ala Tyr Ile Glu Gly Trp Lys Lys Leu Ala Thr Asp Glu Leu Glu
            340                 345                 350
```

```
Lys Tyr Ala Lys Asn Glu Pro Thr Leu Ile Arg Ile Trp Gly Asp Ala
            355                 360                 365

Leu Phe Asp Ile Val Asp Lys Asp Gln Asn Gly Ala Ile Thr Leu Asp
    370                 375                 380

Glu Trp Lys Ala Tyr Thr Lys Ala Ala Gly Ile Ile Gln Ser Ser Glu
385                 390                 395                 400

Asp Cys Glu Glu Thr Phe Arg Val Cys Asp Ile Asp Glu Ser Gly Gln
                405                 410                 415

Leu Asp Val Asp Glu Met Thr Arg Gln His Leu Gly Phe Trp Tyr Thr
            420                 425                 430

Met Asp Pro Ala Cys Glu Lys Leu Tyr Gly Gly Ala Val Pro
            435                 440                 445

<210> SEQ ID NO 17
<211> LENGTH: 450
<212> TYPE: PRT
<213> ORGANISM: Artificial Sequence
<220> FEATURE:
<223> OTHER INFORMATION: synthetic construct

<400> SEQUENCE: 17

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Thr Glu Leu Tyr Lys Ser Gly Ser Gly Ser Gly Gly Gln Ser Gly
                245                 250                 255

Ser Ser Lys Tyr Ala Val Lys Leu Lys Thr Asp Phe Asp Asn Pro Arg
                260                 265                 270
```

```
Trp Ile Lys Arg His Lys His Met Phe Asp Phe Leu Asp Ile Asn Gly
            275                 280                 285

Asn Gly Lys Ile Thr Leu Asp Glu Ile Val Ser Lys Ala Ser Asp Asp
        290                 295                 300

Ile Cys Ala Lys Leu Glu Ala Thr Pro Glu Gln Thr Lys Arg His Gln
305                 310                 315                 320

Val Cys Val Glu Ala Phe Phe Arg Gly Cys Gly Met Glu Tyr Gly Lys
                325                 330                 335

Glu Ile Ala Phe Pro Gln Phe Leu Asp Gly Trp Lys Gln Leu Ala Thr
            340                 345                 350

Ser Glu Leu Lys Lys Trp Ala Arg Asn Glu Pro Thr Leu Ile Arg Glu
        355                 360                 365

Trp Gly Asp Ala Val Phe Asp Ile Phe Asp Lys Asp Gly Ser Gly Thr
370                 375                 380

Ile Thr Leu Asp Glu Trp Lys Ala Tyr Gly Lys Ile Ser Gly Ile Ser
385                 390                 395                 400

Pro Ser Gln Glu Asp Cys Glu Ala Thr Phe Arg His Cys Asp Leu Asp
                405                 410                 415

Asn Ser Gly Asp Leu Asp Val Asp Glu Met Thr Arg Gln His Leu Gly
            420                 425                 430

Phe Trp Tyr Thr Leu Asp Pro Glu Ala Asp Gly Leu Tyr Gly Asn Gly
        435                 440                 445

Val Pro
    450

<210> SEQ ID NO 18
<211> LENGTH: 450
<212> TYPE: PRT
<213> ORGANISM: Artificial Sequence
<220> FEATURE:
<223> OTHER INFORMATION: synthetic construct

<400> SEQUENCE: 18

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Ala Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175
```

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Thr Glu Leu Tyr Lys Ser Gly Gly Ser Gly Gly Gln Ser Gly
                245                 250                 255

Ser Ser Lys Tyr Ala Val Lys Leu Lys Thr Phe Asp Asn Pro Arg
            260                 265                 270

Trp Ile Lys Arg His Lys His Met Phe Asp Phe Leu Asp Ile Asn Gly
        275                 280                 285

Asn Gly Lys Ile Thr Leu Asp Glu Ile Val Ser Lys Ala Ser Asp Asp
    290                 295                 300

Ile Cys Ala Lys Leu Glu Ala Thr Pro Glu Gln Thr Lys Arg His Gln
305                 310                 315                 320

Val Cys Val Glu Ala Phe Phe Arg Gly Cys Gly Met Glu Tyr Gly Lys
                325                 330                 335

Glu Ile Ala Phe Pro Gln Phe Leu Asp Gly Trp Lys Gln Leu Ala Thr
            340                 345                 350

Ser Glu Leu Lys Lys Trp Ala Arg Asn Glu Pro Thr Leu Ile Arg Glu
        355                 360                 365

Trp Gly Asp Ala Val Phe Asp Ile Phe Asp Lys Asp Gly Ser Gly Thr
    370                 375                 380

Ile Thr Leu Asp Glu Trp Lys Ala Tyr Gly Lys Ile Ser Gly Ile Ser
385                 390                 395                 400

Pro Ser Gln Glu Asp Cys Glu Ala Thr Phe Arg His Cys Asp Leu Asp
                405                 410                 415

Asn Ser Gly Asp Leu Asp Val Asp Glu Met Thr Arg Gln His Leu Gly
            420                 425                 430

Phe Trp Tyr Thr Leu Asp Pro Glu Ala Asp Gly Leu Tyr Gly Asn Gly
        435                 440                 445

Val Pro
    450

<210> SEQ ID NO 19
<211> LENGTH: 448
<212> TYPE: PRT
<213> ORGANISM: Artificial Sequence
<220> FEATURE:
<223> OTHER INFORMATION: synthetic construct

<400> SEQUENCE: 19

Met Val Ser Lys Gly Glu Glu Leu Ile Lys Glu Asn Met His Met Lys
1               5                   10                  15

Leu Tyr Met Glu Gly Thr Val Asp Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Leu Tyr Gly Ser Lys Thr Phe Ile Asn His Thr Gln Gly Ile
65                  70                  75                  80

```
Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Thr Ser Asn Gly Pro Val Met Gln Lys Lys Thr Leu Gly Trp
    130                 135                 140

Glu Ala Phe Thr Glu Thr Leu Tyr Pro Ala Asp Gly Gly Leu Glu Gly
145                 150                 155                 160

Arg Asn Asp Met Ala Leu Lys Leu Val Gly Gly Ser His Leu Ile Ala
                165                 170                 175

Asn Ala Lys Thr Thr Tyr Arg Ser Lys Lys Pro Ala Lys Asn Leu Lys
            180                 185                 190

Met Pro Gly Val Tyr Tyr Val Asp Tyr Arg Leu Glu Arg Ile Lys Glu
        195                 200                 205

Ala Asn Asn Glu Thr Tyr Val Glu Gln His Glu Val Ala Val Ala Arg
    210                 215                 220

Tyr Cys Asp Leu Pro Ser Lys Leu Gly His Lys Leu Asn Gly Thr Glu
225                 230                 235                 240

Leu Tyr Lys Ser Gly Gly Ser Gly Gly Gln Ser Gly Ser Ser
                245                 250                 255

Lys Tyr Ala Val Lys Leu Lys Thr Asp Phe Asp Asn Pro Arg Trp Ile
                260                 265                 270

Lys Arg His Lys His Met Phe Asp Phe Leu Asp Ile Asn Gly Asn Gly
                275                 280                 285

Lys Ile Thr Leu Asp Glu Ile Val Ser Lys Ala Ser Asp Asp Ile Cys
            290                 295                 300

Ala Lys Leu Glu Ala Thr Pro Glu Gln Thr Lys Arg His Gln Val Cys
305                 310                 315                 320

Val Glu Ala Phe Phe Arg Gly Cys Gly Met Glu Tyr Gly Lys Glu Ile
                325                 330                 335

Ala Phe Pro Gln Phe Leu Asp Gly Trp Lys Gln Leu Ala Thr Ser Glu
                340                 345                 350

Leu Lys Lys Trp Ala Arg Asn Glu Pro Thr Leu Ile Arg Glu Trp Gly
            355                 360                 365

Asp Ala Val Phe Asp Ile Phe Asp Lys Asp Gly Ser Gly Thr Ile Thr
370                 375                 380

Leu Asp Glu Trp Lys Ala Tyr Gly Lys Ile Ser Gly Ile Ser Pro Ser
385                 390                 395                 400

Gln Glu Asp Cys Glu Ala Thr Phe Arg His Cys Asp Leu Asp Asn Ser
                405                 410                 415

Gly Asp Leu Asp Val Asp Glu Met Thr Arg Gln His Leu Gly Phe Trp
                420                 425                 430

Tyr Thr Leu Asp Pro Glu Ala Asp Gly Leu Tyr Gly Asn Gly Val Pro
            435                 440                 445

<210> SEQ ID NO 20
<211> LENGTH: 447
<212> TYPE: PRT
<213> ORGANISM: Artificial Sequence
<220> FEATURE:
<223> OTHER INFORMATION: synthetic construct

<400> SEQUENCE: 20
```

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
            115                 120                 125

Leu Lys Gly Glu Asn Phe Pro Pro Asn Gly Pro Val Met Gln Lys Lys
130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
            195                 200                 205

His Asp Lys Asp Tyr Asn Lys Val Thr Val Tyr Glu Ser Ala Val Ala
210                 215                 220

Arg Asn Ser Thr Asp Gly Met Asp Glu Leu Tyr Lys Gly Thr Glu Leu
225                 230                 235                 240

Tyr Lys Ser Gly Gly Ser Gly Gly Gln Ser Gly Ser Ser Lys
                245                 250                 255

Tyr Ala Val Lys Leu Lys Thr Asp Phe Asp Asn Pro Arg Trp Ile Lys
            260                 265                 270

Arg His Lys His Met Phe Asp Phe Leu Asp Ile Asn Gly Asn Gly Lys
            275                 280                 285

Ile Thr Leu Asp Glu Ile Val Ser Lys Ala Ser Asp Asp Ile Cys Ala
            290                 295                 300

Lys Leu Glu Ala Thr Pro Glu Gln Thr Lys Arg His Gln Val Cys Val
305                 310                 315                 320

Glu Ala Phe Phe Arg Gly Cys Gly Met Glu Tyr Gly Lys Glu Ile Ala
                325                 330                 335

Phe Pro Gln Phe Leu Asp Gly Trp Lys Gln Leu Ala Thr Ser Glu Leu
            340                 345                 350

Lys Lys Trp Ala Arg Asn Glu Pro Thr Leu Ile Arg Glu Trp Gly Asp
            355                 360                 365

Ala Val Phe Asp Ile Phe Asp Lys Asp Gly Ser Gly Thr Ile Thr Leu
370                 375                 380

Asp Glu Trp Lys Ala Tyr Gly Lys Ile Ser Gly Ile Ser Pro Ser Gln
385                 390                 395                 400

Glu Asp Cys Glu Ala Thr Phe Arg His Cys Asp Leu Asp Asn Ser Gly
                405                 410                 415
```

```
Asp Leu Asp Val Asp Glu Met Thr Arg Gln His Leu Gly Phe Trp Tyr
            420                 425                 430

Thr Leu Asp Pro Glu Ala Asp Gly Leu Tyr Gly Asn Gly Val Pro
            435                 440                 445

<210> SEQ ID NO 21
<211> LENGTH: 450
<212> TYPE: PRT
<213> ORGANISM: Artificial Sequence
<220> FEATURE:
<223> OTHER INFORMATION: synthetic construct

<400> SEQUENCE: 21

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Thr Glu Leu Tyr Lys Ser Gly Gly Ser Gly Gly Gln Ser Gly
                245                 250                 255

Thr Ser Lys Tyr Ala Val Lys Leu Glu Pro Asp Phe Glu Asn Pro Lys
            260                 265                 270

Trp Val Gly Arg His Lys His Met Phe Lys Phe Leu Asp Val Asn Gln
        275                 280                 285

Asn Gly Lys Ile Ser Leu Asp Glu Met Val Tyr Lys Ala Ser Asp Ile
    290                 295                 300

Val Ile Asn Asn Leu Gly Ala Thr Pro Glu Gln Ala Lys Arg His Lys
305                 310                 315                 320

Asp Ala Val Glu Ala Phe Phe Gly Gly Ala Gly Met Lys Tyr Gly Val
                325                 330                 335
```

-continued

```
Glu Thr Glu Trp Pro Glu Tyr Ile Glu Gly Trp Lys Asn Leu Ala Arg
                340                 345                 350

Thr Glu Leu Asp Arg Phe Ala Lys Asn Gln Ile Thr Leu Ile Arg Leu
            355                 360                 365

Trp Gly Asp Ala Leu Phe Asp Ile Ile Asp Lys Asp Gln Asn Gly Ala
        370                 375                 380

Ile Thr Leu Asp Glu Trp Lys Lys Tyr Thr Leu Ser Ala Gly Ile Ile
385                 390                 395                 400

Gln Ser Ala Glu Asp Cys Glu Ile Thr Phe Lys Val Cys Asp Leu Asp
                405                 410                 415

Asp Ser Gly Arg Leu Asp Ala Asp Glu Met Thr Arg Gln His Ile Gly
            420                 425                 430

Phe Trp Tyr Thr Met Asp Pro Ala Cys Glu Lys Leu Tyr Gly Gly Ala
        435                 440                 445

Val Pro
450

<210> SEQ ID NO 22
<211> LENGTH: 450
<212> TYPE: PRT
<213> ORGANISM: Artificial Sequence
<220> FEATURE:
<223> OTHER INFORMATION: synthetic construct

<400> SEQUENCE: 22

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Ala Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240
```

```
Thr Glu Leu Tyr Lys Ser Gly Gly Ser Gly Gly Gln Ser Gly
            245                 250                 255

Thr Ser Lys Tyr Ala Val Lys Leu Glu Pro Asp Phe Glu Asn Pro Lys
        260                 265                 270

Trp Val Gly Arg His Lys His Met Phe Lys Phe Leu Asp Val Asn Gln
        275                 280                 285

Asn Gly Lys Ile Ser Leu Asp Glu Met Val Tyr Lys Ala Ser Asp Ile
        290                 295                 300

Val Ile Asn Asn Leu Gly Ala Thr Pro Glu Gln Ala Lys Arg His Lys
305                 310                 315                 320

Asp Ala Val Glu Ala Phe Phe Gly Gly Ala Gly Met Lys Tyr Gly Val
                325                 330                 335

Glu Thr Glu Trp Pro Glu Tyr Ile Glu Gly Trp Lys Asn Leu Ala Arg
            340                 345                 350

Thr Glu Leu Asp Arg Phe Ala Lys Asn Gln Ile Thr Leu Ile Arg Leu
        355                 360                 365

Trp Gly Asp Ala Leu Phe Asp Ile Ile Asp Lys Asp Gln Asn Gly Ala
    370                 375                 380

Ile Thr Leu Asp Glu Trp Lys Lys Tyr Thr Leu Ser Ala Gly Ile Ile
385                 390                 395                 400

Gln Ser Ala Glu Asp Cys Glu Ile Thr Phe Lys Val Cys Asp Leu Asp
                405                 410                 415

Asp Ser Gly Arg Leu Asp Ala Asp Glu Met Thr Arg Gln His Ile Gly
            420                 425                 430

Phe Trp Tyr Thr Met Asp Pro Ala Cys Glu Lys Leu Tyr Gly Gly Ala
        435                 440                 445

Val Pro
    450

<210> SEQ ID NO 23
<211> LENGTH: 448
<212> TYPE: PRT
<213> ORGANISM: Artificial Sequence
<220> FEATURE:
<223> OTHER INFORMATION: synthetic construct

<400> SEQUENCE: 23

Met Val Ser Lys Gly Glu Glu Leu Ile Lys Glu Asn Met His Met Lys
1               5                   10                  15

Leu Tyr Met Glu Gly Thr Val Asp Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Leu Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Thr Ser Asn Gly Pro Val Met Gln Lys Lys Thr Leu Gly Trp
    130                 135                 140
```

```
Glu Ala Phe Thr Glu Thr Leu Tyr Pro Ala Asp Gly Gly Leu Glu Gly
145                 150                 155                 160

Arg Asn Asp Met Ala Leu Lys Leu Val Gly Gly Ser His Leu Ile Ala
            165                 170                 175

Asn Ala Lys Thr Thr Tyr Arg Ser Lys Lys Pro Ala Lys Asn Leu Lys
            180                 185                 190

Met Pro Gly Val Tyr Tyr Val Asp Tyr Arg Leu Glu Arg Ile Lys Glu
            195                 200                 205

Ala Asn Asn Glu Thr Tyr Val Glu Gln His Glu Val Ala Val Ala Arg
        210                 215                 220

Tyr Cys Asp Leu Pro Ser Lys Leu Gly His Lys Leu Asn Gly Thr Glu
225                 230                 235                 240

Leu Tyr Lys Ser Gly Ser Gly Ser Gly Gln Ser Gly Thr Ser
                245                 250                 255

Lys Tyr Ala Val Lys Leu Glu Pro Asp Phe Glu Asn Pro Lys Trp Val
                260                 265                 270

Gly Arg His Lys His Met Phe Lys Phe Leu Asp Val Asn Gln Asn Gly
            275                 280                 285

Lys Ile Ser Leu Asp Glu Met Val Tyr Lys Ala Ser Asp Ile Val Ile
            290                 295                 300

Asn Asn Leu Gly Ala Thr Pro Glu Gln Ala Lys Arg His Lys Asp Ala
305                 310                 315                 320

Val Glu Ala Phe Phe Gly Gly Ala Gly Met Lys Tyr Gly Val Glu Thr
                325                 330                 335

Glu Trp Pro Glu Tyr Ile Glu Gly Trp Lys Asn Leu Ala Arg Thr Glu
                340                 345                 350

Leu Asp Arg Phe Ala Lys Asn Gln Ile Thr Leu Ile Arg Leu Trp Gly
            355                 360                 365

Asp Ala Leu Phe Asp Ile Ile Asp Lys Asp Gln Asn Gly Ala Ile Thr
        370                 375                 380

Leu Asp Glu Trp Lys Lys Tyr Thr Leu Ser Ala Gly Ile Ile Gln Ser
385                 390                 395                 400

Ala Glu Asp Cys Glu Ile Thr Phe Lys Val Cys Asp Leu Asp Asp Ser
                405                 410                 415

Gly Arg Leu Asp Ala Asp Glu Met Thr Arg Gln His Ile Gly Phe Trp
            420                 425                 430

Tyr Thr Met Asp Pro Ala Cys Glu Lys Leu Tyr Gly Gly Ala Val Pro
        435                 440                 445

<210> SEQ ID NO 24
<211> LENGTH: 447
<212> TYPE: PRT
<213> ORGANISM: Artificial Sequence
<220> FEATURE:
<223> OTHER INFORMATION: synthetic construct

<400> SEQUENCE: 24

Met Val Ser Lys Gly Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60
```

Ile Leu Thr Thr Ala Phe Ala Tyr Gly Asn Arg Ala Phe Thr Lys Tyr
 65                  70                  75                  80

Pro Asp Asp Ile Pro Asn Tyr Phe Lys Gln Ser Phe Pro Glu Gly Tyr
                 85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Lys
130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
210                 215                 220

Arg Asn Ser Thr Asp Gly Met Asp Glu Leu Tyr Lys Gly Thr Glu Leu
225                 230                 235                 240

Tyr Lys Ser Gly Gly Ser Gly Gly Gly Gln Ser Gly Thr Ser Lys
                245                 250                 255

Tyr Ala Val Lys Leu Glu Pro Asp Phe Glu Asn Pro Lys Trp Val Gly
            260                 265                 270

Arg His Lys His Met Phe Lys Phe Leu Asp Val Asn Gln Asn Gly Lys
        275                 280                 285

Ile Ser Leu Asp Glu Met Val Tyr Lys Ala Ser Asp Ile Val Ile Asn
    290                 295                 300

Asn Leu Gly Ala Thr Pro Glu Gln Ala Lys Arg His Lys Asp Ala Val
305                 310                 315                 320

Glu Ala Phe Phe Gly Gly Ala Gly Met Lys Tyr Gly Val Glu Thr Glu
                325                 330                 335

Trp Pro Glu Tyr Ile Glu Gly Trp Lys Asn Leu Ala Arg Thr Glu Leu
            340                 345                 350

Asp Arg Phe Ala Lys Asn Gln Ile Thr Leu Ile Arg Leu Trp Gly Asp
        355                 360                 365

Ala Leu Phe Asp Ile Ile Asp Lys Asp Gln Asn Gly Ala Ile Thr Leu
370                 375                 380

Asp Glu Trp Lys Lys Tyr Thr Leu Ser Ala Gly Ile Ile Gln Ser Ala
385                 390                 395                 400

Glu Asp Cys Glu Ile Thr Phe Lys Val Cys Asp Leu Asp Asp Ser Gly
                405                 410                 415

Arg Leu Asp Ala Asp Glu Met Thr Arg Gln His Ile Gly Phe Trp Tyr
            420                 425                 430

Thr Met Asp Pro Ala Cys Glu Lys Leu Tyr Gly Gly Ala Val Pro
        435                 440                 445

<210> SEQ ID NO 25
<211> LENGTH: 1467
<212> TYPE: DNA
<213> ORGANISM: Artificial Sequence
<220> FEATURE:
<223> OTHER INFORMATION: synthetic construct

<400> SEQUENCE: 25

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acgactacaa cagccacaac gtctatatca tggccgacaa gcagaagaac     480
ggcatcaagg cgaacttcaa gacccgccac aacatcgagg acggcggcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagctc     720
gagtccggcg ggagcggctc cggcggccag tccggcggga gcggatccgg cggccagtcc     780
gggggatctg gcagcggagg acagtccggg ggatctggca gcggcggcca gagcggcgga     840
tctggcagcg gcgccagag cggcgagctc ctgtacgacg tgcccgacta cgccagcctg     900
aagctgacca gcgacttcga caacccccgc tggatcggcc gccacaagca catgttcaac     960
ttcctggacg tgaaccacaa cggcaagatc agcctggacg agatggtgta caaggccagc    1020
gacatcgtga tcaacaacct gggcgccacc cccgagcagg ccaagcgcca aaggacgcc     1080
gtggaggcct tcttcggcgg cgccggcatg aagtacggcg tggagaccga ctggcccgcc    1140
tacatcgagg gctggaagaa gctggccacc gacgagctgg agaagtacgc caagaacgag    1200
cccaccctga tccgcatctg gggcgacgcc ctgttcgaca tcgtggacaa ggaccagaac    1260
ggcgccatca ccctggacga gtggaaggcc tacaccaagg ccgccggcat catccagagc    1320
agcgaggact gcgaggagac cttccgcgtg tgcgacatcg acgagagcgg ccagctggac    1380
gtggacgaga tgacccgcca gcacctgggc ttctggtaca ccatggaccc cgcctgcgag    1440
aagctgtacg cggcgccgt gccctga                                         1467
```

<210> SEQ ID NO 26
<211> LENGTH: 486
<212> TYPE: PRT
<213> ORGANISM: Artificial Sequence
<220> FEATURE:
<223> OTHER INFORMATION: synthetic construct

<400> SEQUENCE: 26

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
```

```
                    85                  90                  95
Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Asp
        130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys Leu Glu
225                 230                 235                 240

Ser Gly Gly Ser Gly Gly Gly Gln Ser Gly Gly Ser Gly Ser Ser Gly
                245                 250                 255

Gly Gln Ser Gly Gly Ser Gly Ser Gly Gly Gln Ser Gly Gly Ser Gly
            260                 265                 270

Ser Gly Gly Gln Ser Gly Gly Ser Gly Ser Gly Gly Gln Ser Gly Glu
        275                 280                 285

Leu Leu Tyr Asp Val Pro Asp Tyr Ala Ser Leu Lys Leu Thr Ser Asp
290                 295                 300

Phe Asp Asn Pro Arg Trp Ile Gly Arg His Lys His Met Phe Asn Phe
305                 310                 315                 320

Leu Asp Val Asn His Asn Gly Lys Ile Ser Leu Asp Glu Met Val Tyr
                325                 330                 335

Lys Ala Ser Asp Ile Val Ile Asn Asn Leu Gly Ala Thr Pro Glu Gln
            340                 345                 350

Ala Lys Arg His Asp Ala Val Glu Ala Phe Phe Gly Gly Ala Gly Met
        355                 360                 365

Lys Tyr Gly Val Glu Thr Asp Trp Pro Ala Tyr Ile Glu Gly Trp Lys
370                 375                 380

Lys Leu Ala Thr Asp Glu Leu Glu Lys Tyr Ala Lys Asn Glu Pro Thr
385                 390                 395                 400

Leu Ile Arg Ile Trp Gly Asp Ala Leu Phe Asp Ile Val Asp Lys Asp
                405                 410                 415

Gln Asn Gly Ala Ile Thr Leu Asp Glu Trp Lys Ala Tyr Thr Lys Ala
            420                 425                 430

Ala Gly Ile Ile Gln Ser Ser Glu Asp Cys Glu Glu Thr Phe Arg Val
        435                 440                 445

Cys Asp Ile Asp Glu Ser Gly Gln Leu Asp Val Asp Glu Met Thr Arg
450                 455                 460

Gln His Leu Gly Phe Trp Tyr Thr Met Asp Pro Ala Cys Glu Lys Leu
465                 470                 475                 480

Tyr Gly Gly Ala Val Pro
                485

<210> SEQ ID NO 27
```

<211> LENGTH: 2058
<212> TYPE: DNA
<213> ORGANISM: Artificial Sequence
<220> FEATURE:
<223> OTHER INFORMATION: synthetic construct

<400> SEQUENCE: 27

| | | | | | |
|---|---|---|---|---|---|
| atggtgagca | agggcgagga | ggtcatcaaa | gagttcatgc | gcttcaaggt | gcgcatggag | 60 |
| ggctccatga | acggccacga | gttcgagatc | gagggcgagg | gcgagggccg | ccctacgag | 120 |
| ggcacccaga | ccgccaagct | gaaggtgacc | aagggcggcc | ccctgccctt | cgcctgggac | 180 |
| atcctgtccc | cccagttcat | gtacggctcc | aaggcgtacg | tgaagcaccc | cgccgacatc | 240 |
| cccgattaca | agaagctgtc | cttccccgag | ggcttcaagt | gggagcgcgt | gatgaacttc | 300 |
| gaggacggcg | gtctggtgac | cgtgacccag | gactcctccc | tgcaggacgg | cacgctgatc | 360 |
| tacaaggtga | agatgcgcgg | caccaacttc | cccccgacg | gccccgtaat | gcagaagaag | 420 |
| accatgggct | gggaggcctc | caccgagcgc | ctgtaccccc | gcgacggcgt | gctgaagggc | 480 |
| gagatccacc | aggccctgaa | gctgaaggac | ggcggccact | acctggtgga | gttcaagacc | 540 |
| atctacatgg | ccaagaagcc | cgtgcaactg | cccggctact | actacgtgga | caccaagctg | 600 |
| gacatcacct | cccacaacga | ggactacacc | atcgtggaac | agtacgagcg | ctccgagggc | 660 |
| cgccaccacc | tgttcctggg | gcatggcacc | ggcagcaccg | gcagcggcag | ctccggcacc | 720 |
| gcctcctccg | aggacaacaa | catggccgtc | atcaaagagt | tcatgcgctt | caaggtgcgc | 780 |
| atggagggct | ccatgaacgg | ccacgagttc | gagatcgagg | gcgagggcga | gggccgcccc | 840 |
| tacgagggca | cccagaccgc | caagctgaag | gtgaccaagg | gcggcccct | gcccttcgcc | 900 |
| tgggacatcc | tgtccccca | gttcatgtac | ggctccaagg | cgtacgtgaa | gcaccccgcc | 960 |
| gacatcccg | attacaagaa | gctgtccttc | cccgagggct | tcaagtggga | gcgcgtgatg | 1020 |
| aacttcgagg | acggcggtct | ggtgaccgtg | acccaggact | cctccctgca | ggacggcacg | 1080 |
| ctgatctaca | aggtgaagat | gcgcggcacc | aacttccccc | cgacggccc | cgtaatgcag | 1140 |
| aagaagacca | tgggctggga | ggcctccacc | gagcgcctgt | accccgcga | cggcgtgctg | 1200 |
| aagggcgaga | tccaccaggc | cctgaagctg | aaggacggcg | gccactacct | ggtggagttc | 1260 |
| aagaccatct | acatggccaa | gaagcccgtg | caactgcccg | gctactacta | cgtggacacc | 1320 |
| aagctggaca | tcacctccca | caacgaggac | tacaccatcg | tggaacagta | cgagcgctcc | 1380 |
| gagggccgcc | accacctgtt | cctgtacggc | atggacgagc | tgtacaaggg | taccgagctg | 1440 |
| tacaagtccg | gcgggagcgg | atccggcggc | cagtccggac | tcagatctgt | caaacttaca | 1500 |
| tcagacttcg | acaacccaag | atggattgga | cgacacaagc | atatgttcaa | tttccttgat | 1560 |
| gtcaaccaca | atggaaaaat | ctctcttgac | gagatggtct | acaaggcatc | tgatattgtc | 1620 |
| atcaataacc | ttggagcaac | acctgagcaa | gccaaacgac | acaaagatgc | tgtggaagcc | 1680 |
| ttcttcggag | gagctggaat | gaaatatggt | gtggaaactg | attggcctgc | atatattgaa | 1740 |
| ggatggaaaa | aattggctac | tgatgaattg | gagaaatacg | ccaaaaacga | accaaccctc | 1800 |
| atccgcatct | ggggtgatgc | tttgtttgat | atcgttgaca | agatcaaaa | tggagctatt | 1860 |
| acactggatg | aatggaaagc | ataccaccaa | gctgctggta | tcatccaatc | atcagaagat | 1920 |
| tgcgaggaaa | cattcagagt | gtgcgatatt | gatgaaagtg | gacaactcga | tgttgatgag | 1980 |
| atgacaagac | agcatctggg | atttttggtac | accatggatc | tgcttgcga | aaagctctac | 2040 |
| ggtggagctg | tccctaa | | | | | 2058 |

<210> SEQ ID NO 28
<211> LENGTH: 682
<212> TYPE: PRT
<213> ORGANISM: Artificial Sequence
<220> FEATURE:
<223> OTHER INFORMATION: synthetic construct

<400> SEQUENCE: 28

```
Met Val Ser Lys Gly Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Ile Leu Ser Pro Gln
50                  55                  60

Phe Met Tyr Gly Ser Lys Ala Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Leu Val Thr Val Thr Gln Asp Ser Ser
            100                 105                 110

Leu Gln Asp Gly Thr Leu Ile Tyr Lys Val Lys Met Arg Gly Thr Asn
        115                 120                 125

Phe Pro Pro Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Gln Ala Leu Lys Leu Lys Asp Gly Gly His Tyr Leu Val Glu
                165                 170                 175

Phe Lys Thr Ile Tyr Met Ala Lys Lys Pro Val Gln Leu Pro Gly Tyr
            180                 185                 190

Tyr Tyr Val Asp Thr Lys Leu Asp Thr Ser His Asn Glu Asp Tyr Thr
        195                 200                 205

Ile Val Glu Gln Tyr Glu Arg Ser Glu Gly Arg His His Leu Phe Leu
210                 215                 220

Gly His Gly Thr Gly Ser Thr Gly Ser Gly Ser Ser Gly Thr Ala Ser
225                 230                 235                 240

Ser Glu Asp Asn Asn Met Ala Val Ile Lys Glu Phe Met Arg Phe Lys
                245                 250                 255

Val Arg Met Glu Gly Ser Met Asn Gly His Glu Phe Glu Ile Glu Gly
            260                 265                 270

Glu Gly Glu Gly Arg Pro Tyr Glu Gly Thr Gln Thr Ala Lys Leu Lys
        275                 280                 285

Val Thr Lys Gly Gly Pro Leu Pro Phe Ala Trp Asp Ile Leu Ser Pro
290                 295                 300

Gln Phe Met Tyr Gly Ser Lys Ala Tyr Val Lys His Pro Ala Asp Ile
305                 310                 315                 320

Pro Asp Tyr Lys Lys Leu Ser Phe Pro Glu Gly Phe Lys Trp Glu Arg
                325                 330                 335

Val Met Asn Phe Glu Asp Gly Gly Leu Val Thr Val Thr Gln Asp Ser
            340                 345                 350

Ser Leu Gln Asp Gly Thr Leu Ile Tyr Lys Val Lys Met Arg Gly Thr
        355                 360                 365

Asn Phe Pro Pro Asp Gly Pro Val Met Gln Lys Lys Thr Met Gly Trp
```

```
              370                 375                 380
Glu Ala Ser Thr Glu Arg Leu Tyr Pro Arg Asp Gly Val Leu Lys Gly
385                 390                 395                 400

Glu Ile His Gln Ala Leu Lys Leu Lys Asp Gly Gly His Tyr Leu Val
                405                 410                 415

Glu Phe Lys Thr Ile Tyr Met Ala Lys Lys Pro Val Gln Leu Pro Gly
                420                 425                 430

Tyr Tyr Tyr Val Asp Thr Lys Leu Asp Ile Thr Ser His Asn Glu Asp
                435                 440                 445

Tyr Thr Ile Val Glu Gln Tyr Glu Arg Ser Glu Gly Arg His His Leu
            450                 455                 460

Phe Leu Tyr Gly Met Asp Glu Leu Tyr Lys Gly Thr Glu Leu Tyr Lys
465                 470                 475                 480

Ser Gly Gly Ser Gly Gly Gly Gln Ser Gly Leu Arg Ser Val Lys Leu
                485                 490                 495

Thr Ser Asp Phe Asp Asn Pro Arg Trp Ile Gly Arg His Lys His Met
                500                 505                 510

Phe Asn Phe Leu Asp Val Asn His Asn Gly Lys Ile Ser Leu Asp Glu
            515                 520                 525

Met Val Tyr Lys Ala Ser Asp Ile Val Ile Asn Asn Leu Gly Ala Thr
        530                 535                 540

Pro Glu Gln Ala Lys Arg His Lys Asp Ala Val Glu Ala Phe Phe Gly
545                 550                 555                 560

Gly Ala Gly Met Lys Tyr Gly Val Glu Thr Asp Trp Pro Ala Tyr Ile
                565                 570                 575

Glu Gly Trp Lys Lys Leu Ala Thr Asp Glu Leu Glu Lys Tyr Ala Lys
                580                 585                 590

Asn Glu Pro Thr Leu Ile Arg Ile Trp Gly Asp Ala Leu Phe Asp Ile
            595                 600                 605

Val Asp Lys Asp Gln Asn Gly Ala Ile Thr Leu Asp Glu Trp Lys Ala
        610                 615                 620

Tyr Thr Lys Ala Ala Gly Ile Ile Gln Ser Ser Glu Asp Cys Glu Glu
625                 630                 635                 640

Thr Phe Arg Val Cys Asp Ile Asp Glu Ser Gly Gln Leu Asp Val Asp
                645                 650                 655

Glu Met Thr Arg Gln His Leu Gly Phe Trp Tyr Thr Met Asp Pro Ala
                660                 665                 670

Cys Glu Lys Leu Tyr Gly Gly Ala Val Pro
            675                 680
```